US011896131B2

United States Patent
Lee et al.

(10) Patent No.: US 11,896,131 B2
(45) Date of Patent: Feb. 13, 2024

(54) BED

(71) Applicant: LG ELECTRONICS INC., Seoul (KR)

(72) Inventors: Deukwon Lee, Seoul (KR); Minkyu Oh, Seoul (KR); Yongnam Kim, Seoul (KR); Daewoong Kim, Seoul (KR); Seongwoo An, Seoul (KR); Yanghwan No, Seoul (KR); Keunho Ju, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 434 days.

(21) Appl. No.: 17/096,648

(22) Filed: Nov. 12, 2020

(65) Prior Publication Data

US 2021/0307530 A1    Oct. 7, 2021

(30) Foreign Application Priority Data

Apr. 7, 2020 (KR) .................. 10-2020-0042008
Apr. 7, 2020 (KR) .................. 10-2020-0042009
(Continued)

(51) Int. Cl.
*A61G 7/002* (2006.01)
*A61G 7/015* (2006.01)
(Continued)

(52) U.S. Cl.
CPC .......... *A47C 21/044* (2013.01); *A47C 20/041* (2013.01); *A47C 23/002* (2013.01);
(Continued)

(58) Field of Classification Search
CPC ........ A61G 7/002; A61G 7/015; A61G 7/018; A61G 7/0573; A47C 23/067; A47C 23/0435; A47C 27/061; A47C 21/044
See application file for complete search history.

(56) References Cited

U.S. PATENT DOCUMENTS 2,595,072 A * 4/1952 Gottschalk ......... A47C 23/0435
    5/256
2,630,585 A * 3/1953 Reese ................ A47C 23/0435
    5/248
(Continued)

FOREIGN PATENT DOCUMENTS

CN    202043916    11/2011
CN    104257160    1/2015
(Continued)

OTHER PUBLICATIONS

European Search Report dated Oct. 6, 2021 issued in EP Application No. 20206440.8.
(Continued)

*Primary Examiner* — David R Hare
*Assistant Examiner* — Ifeolu A Adeboyejo
(74) *Attorney, Agent, or Firm* — KED & ASSOCIATES, LLP

(57) ABSTRACT

A bed according to an embodiment may include a topper, at least one firmness adjuster provided under the topper, and a bedframe configured to have an adjustable position and to support the firmness adjuster. There may be a plurality of firmness adjusters corresponding to a plurality of areas of the bed, and each firmness adjuster may include a plurality of cushions provided in a cushion case and a drive to adjust the firmness of the plurality of cushions. The drive may change a position of a first spring relative to a second spring in each of the cushions to change a perceived firmness by a user lying on top of the topper and the firmness adjusters. A dryer may be provided under the bedframe to keep the cushions and topper dry.

23 Claims, 44 Drawing Sheets

(30) Foreign Application Priority Data

| | | |
|---|---|---|
| Apr. 7, 2020 | (KR) | 10-2020-0042010 |
| Apr. 7, 2020 | (KR) | 10-2020-0042012 |
| Apr. 7, 2020 | (KR) | 10-2020-0042015 |
| Apr. 7, 2020 | (KR) | 10-2020-0042018 |
| Apr. 7, 2020 | (KR) | 10-2020-0042019 |
| Apr. 7, 2020 | (KR) | 10-2020-0042020 |
| Apr. 7, 2020 | (KR) | 10-2020-0042021 |

(51) Int. Cl.
*A47C 21/04* (2006.01)
*A47C 20/04* (2006.01)
*A47C 27/06* (2006.01)
*A47C 23/00* (2006.01)
*D06F 60/00* (2009.01)
*A47C 31/00* (2006.01)
*A47C 23/34* (2006.01)
*A47C 27/05* (2006.01)
*A47C 31/12* (2006.01)
*A61G 7/018* (2006.01)
*F24F 8/108* (2021.01)
*A47C 27/10* (2006.01)
*A47C 27/14* (2006.01)
*A47C 23/043* (2006.01)

(52) U.S. Cl.
CPC .......... *A47C 23/34* (2013.01); *A47C 27/053* (2013.01); *A47C 27/064* (2013.01); *A47C 27/065* (2013.01); *A47C 31/008* (2013.01); *A47C 31/12* (2013.01); *D06F 60/00* (2013.01); *A47C 21/048* (2013.01); *A47C 23/043* (2013.01); *A47C 27/05* (2013.01); *A47C 27/10* (2013.01); *A47C 27/14* (2013.01); *A47C 31/123* (2013.01); *A61B 2562/0247* (2013.01); *A61G 7/018* (2013.01); *A61G 2203/12* (2013.01); *A61G 2203/34* (2013.01); *F24F 8/108* (2021.01)

(56) References Cited

U.S. PATENT DOCUMENTS

| | | | | |
|---|---|---|---|---|
| 5,953,778 | A | * | 9/1999 | Hiatt .................... A47C 27/001 5/722 |
| 7,293,309 | B1 | * | 11/2007 | Shih ..................... A47C 20/041 5/618 |
| 7,908,693 | B2 | | 3/2011 | DeMoss |
| 7,934,277 | B1 | * | 5/2011 | Shu ..................... A47C 23/0435 5/936 |
| 8,256,043 | B2 | | 9/2012 | Fromme-Ruthmann |
| 8,402,579 | B2 | | 3/2013 | Marquette et al. |
| 9,119,478 | B2 | | 9/2015 | DeFranks et al. |
| 9,125,497 | B2 | * | 9/2015 | Brykalski ............ A47C 21/048 |
| 9,138,064 | B2 | * | 9/2015 | Tursi, Jr. .............. A47C 21/044 |
| 2012/0042454 | A1 | | 2/2012 | Viberg |
| 2013/0000049 | A1 | | 1/2013 | Hsu |
| 2013/0081205 | A1 | * | 4/2013 | Frondorf ................ A61G 7/015 5/613 |
| 2016/0015183 | A1 | | 1/2016 | Stjerna |
| 2017/0258239 | A1 | * | 9/2017 | Xie ...................... A47C 27/002 |
| 2018/0192781 | A1 | | 7/2018 | Hyltenfeldt et al. |
| 2018/0199728 | A1 | * | 7/2018 | Leng .................... A47C 23/002 |
| 2019/0298074 | A1 | * | 10/2019 | Dan-On .................. A61G 7/018 |
| 2020/0000242 | A1 | * | 1/2020 | Ermalovich ......... A47C 21/048 |
| 2020/0187672 | A1 | * | 6/2020 | Duncan .................... A61H 1/00 |

FOREIGN PATENT DOCUMENTS

| | | |
|---|---|---|
| CN | 108041891 | 5/2018 |
| CN | 108887996 | 11/2018 |
| CN | 208973041 | 6/2019 |
| CN | 209360146 | 9/2019 |
| CN | 110652136 | 1/2020 |
| JP | 2001-104112 | 4/2001 |
| WO | WO 2010/124964 | 11/2010 |
| WO | WO 2014/095552 | 6/2014 |
| WO | WO 2017/005486 | 1/2017 |
| WO | WO 2017/206961 | 12/2017 |

OTHER PUBLICATIONS

Chinese Office Action dated Aug. 23, 2022 issued in CN Application No. 202011097849.7.

Chinese Office Action issued in Application No. 202011097849.7 dated Mar. 1, 2023.

\* cited by examiner

FIG. 16
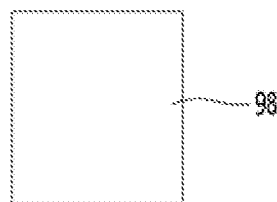 98
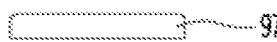 97
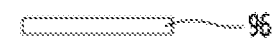 96
 95
 94
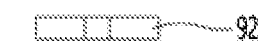 92
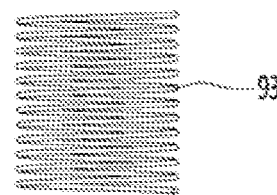 93
 91
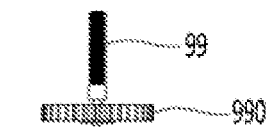 99
990

BED

CROSS-REFERENCE TO RELATED APPLICATIONS

This application claims priority under 35 U.S.C. § 119 to Korean Application 10-2020-0042008, 10-2020-0042009, 10-2020-0042010, 10-2020-0042012, 10-2020-0042015, 10-2020-0042018, 10-2020-0042019, 10-2020-0042020, and 10-2020-0042021, all filed on Apr. 7, 2020, whose entire disclosures are hereby incorporated by reference.

TECHNICAL FIELD

The present invention relates to a bed.

TECHNICAL BACKGROUND OF THE INVENTION

Mattresses provide cushioning for a bed and may be a spring mattress, a sponge mattress, a memory foam mattress, or include some other elastic material. Traditionally, most modern mattresses are spring mattresses, though memory foam mattresses or toppers are increasing in popularity. Mattresses may also use a combination of elastic materials, such as a hybrid coil spring and memory foam mattress.

In a spring mattress, coil springs may be complicatedly entangled to form a single cushion member. However, such complicated coil spring mattresses have a disadvantage in that vibrations from an elastic force of one spring are easily transmitted to another spring such that, when one person lies down on a side of the mattress, vibration or movement may be felt by another person sitting or lying on another side of the mattress, causing discomfort. Some coil spring mattresses may have a plurality of springs in pockets to reduce an amount of vibrations or movement propagating from one side of the mattress to another.

However, such spring mattresses, including the pocket type mattress, is not readily adjustable in firmness or cushion strength. A desired firmness of the mattress may vary according to a user's gender, age, and physical condition. When two or more users use the same mattress, the users may have to compromise on a firmness, as different sides or portions of the spring mattress cannot be easily adjusted or customized.

Various studies and efforts have been made to implement a bed in which firmness may be set differently according to a position of where the user lies down or based on where a user's body touches the mattress.

U.S. Pat. No. 7,908,693 (granted Mar. 22, 2011) discloses a coil-in-coil spring for a mattress. The coil-in-coil spring has an inner spring having a weak elastic strength and an outer spring having a large elastic strength. The outer spring is longer than the inner spring, and the inner and outer springs are provided in a pocket.

Since a length and elasticity of the inner spring and the outer spring are set differently, firmness differs depending on a magnitude of a load acting on an upper surface of the coil-in-coil. When the user lies on the mattress, an amount of contraction or compression of the spring varies for each body part where the load acts differently. However, the firmness is the same or similar for every user or load at a certain weight. The user may not adjust the firmness of the mattress according to his particular desire; rather his weight is what determines the firmness.

U.S. Pat. No. 9,119,478 (granted Sep. 1, 2015) discloses a plunger matrix mattress having a plurality of dual-spring plungers, which have inner and outer tension springs. The firmness of the mattress may be freely set at different predetermined "zones" or positions according to the user's selection. However, from the contents disclosed in FIGS. 3A to 6 of U.S. Pat. No. 9,119,478, a number of zones is limited, and a variable range of the elastic strength is narrow. In addition, since the firmness is adjusted by hand, the firmness at multiple positions or zones cannot be simultaneously adjusted.

U.S. Pat. No. 8,256,043 (granted Sep. 4, 2012) discloses a base plate and a support plate rotatably coupled to the base plate. An elastic strength of a support element is adjusted by a rotation of the support plate. A firmness may be set within a range by a user in rotating, by hand, the support plate.

In the case of the disclosed coil-in-coil mattress, plunger matrix mattress, and base plate and support plate mattress, sweat or other bodily fluids may permeate a surface of the mattress touching the skin, and in summer, when the humidity is high, not only the mattress but also the sheets may be wet or moist, causing discomfort. If the mattress is kept wet for a long time, the mattress is very likely to be contaminated with mold or mites.

In order to improve this problem, U.S. Pat. No. 8,402,579 (granted Mar. 26, 2013) discloses a climate controlled bed having a thermoelectric device and air distribution device to supply hot or cold air to the mattress. However, there is a disadvantage in that hot or cold air is not smoothly or evenly supplied to the mattress.

The above references are incorporated by reference herein where appropriate for appropriate teachings of additional or alternative details, features and/or technical background.

BRIEF DESCRIPTION OF THE DRAWINGS

Embodiments will be described in detail with reference to the following drawings in which like reference numerals refer to like elements, and wherein:

FIG. 16 is an exploded perspective view of the cushion;

DETAILED DESCRIPTION OF THE INVENTION

Figure 1:
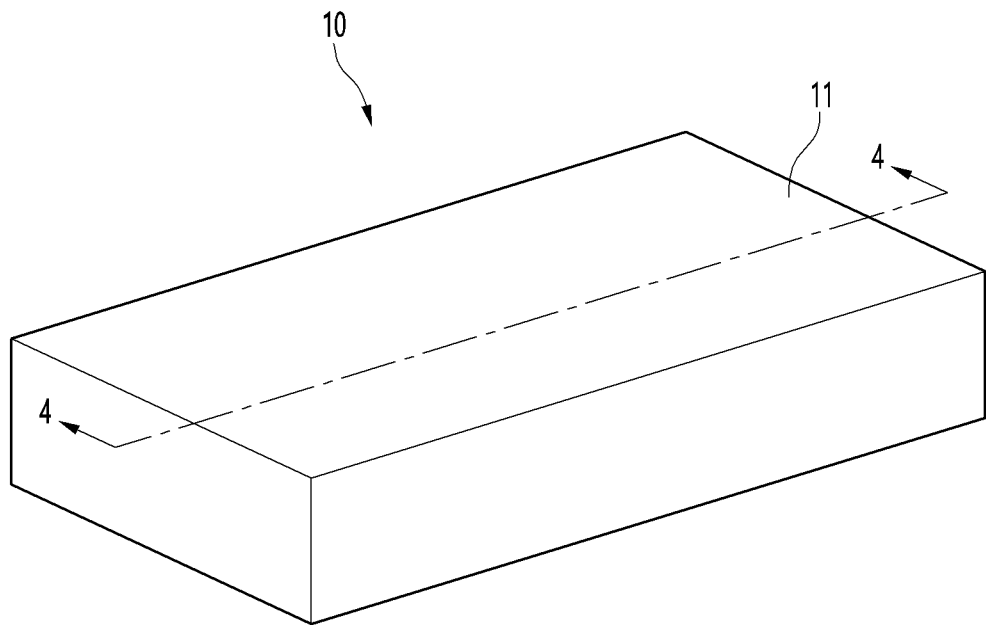
FIG. 1 is a perspective view of a bed according to an embodiment.
Figure 2:
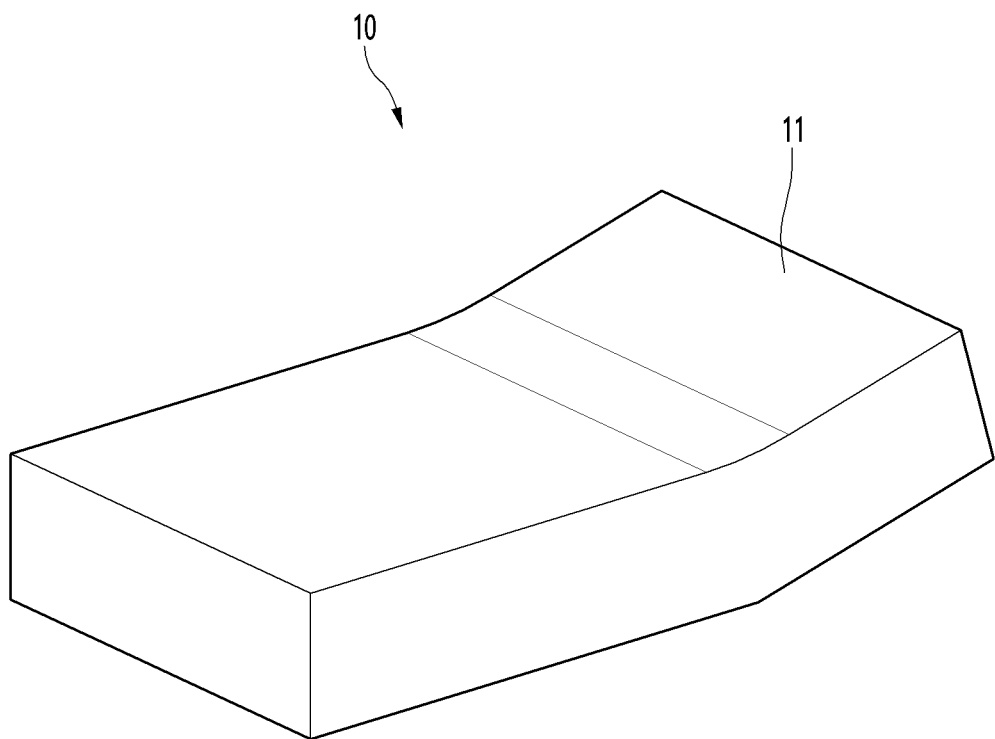
FIG. 2 is a perspective view of the bed of FIG. 1 showing a state in which an upper portion of the bed is raised or tiled by an angle.
Figure 3:
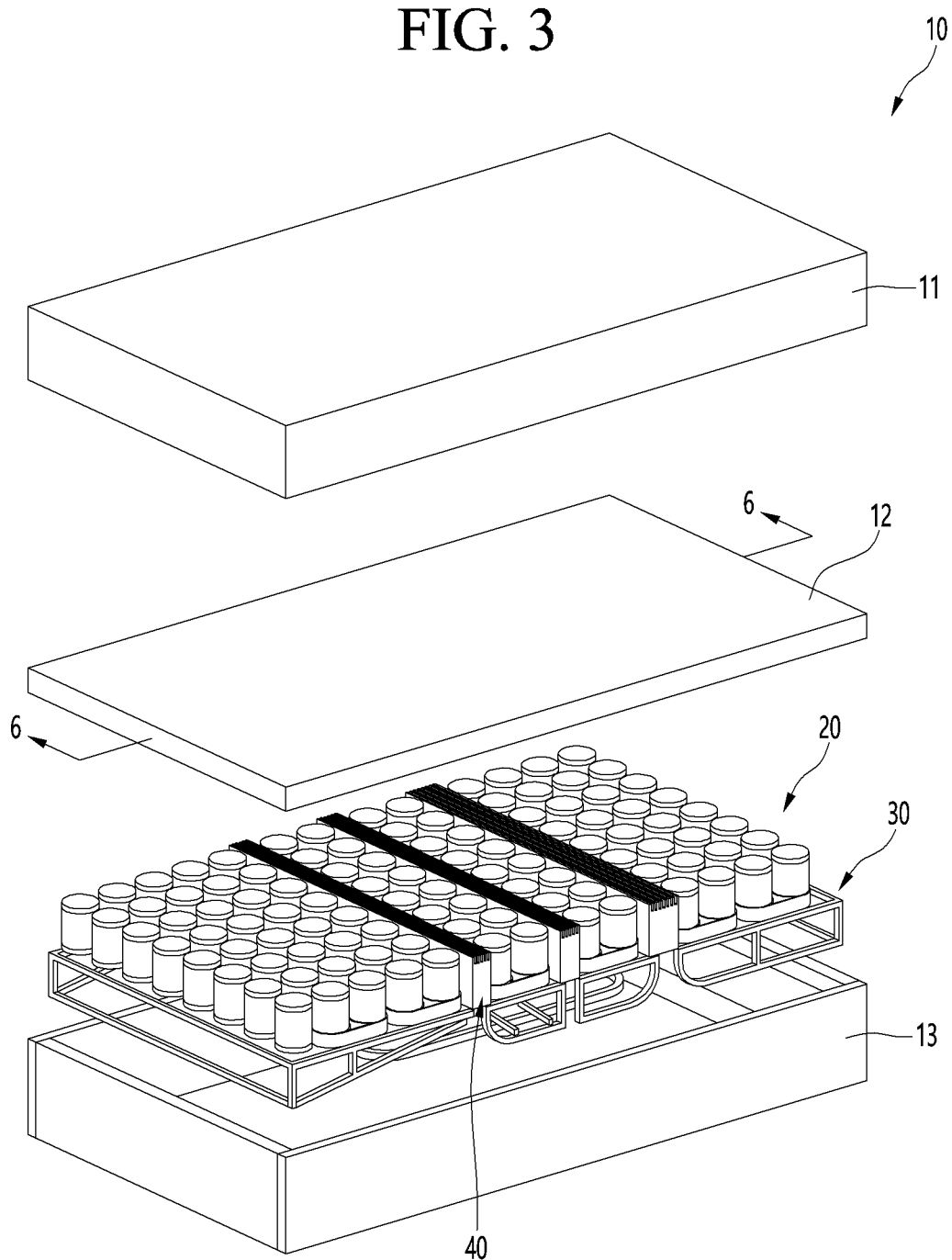
FIG. 3 is an exploded perspective view of the bed of FIG. 1.
Figure 4:
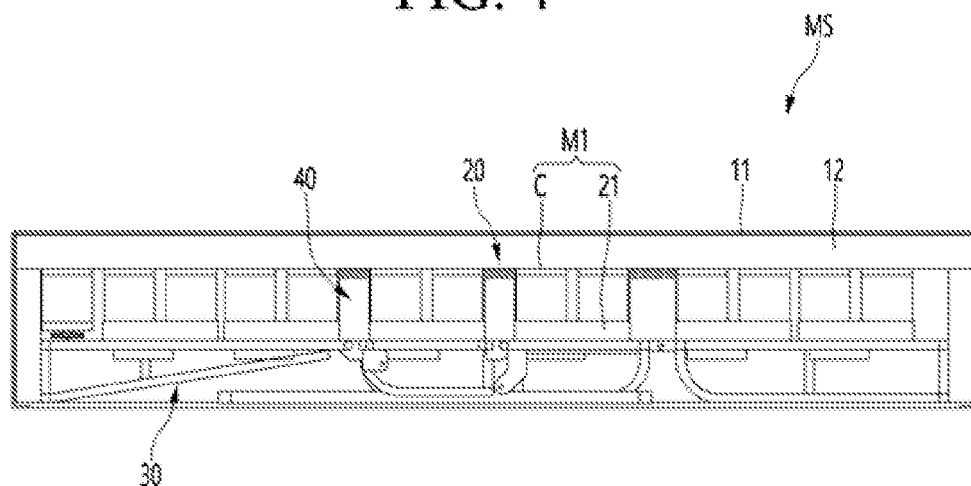
FIG. 4 is a longitudinal sectional view of the bed cut along 4-4 of FIG. 1.

Referring to FIGS. 1 to 4, a bed 10 according to an embodiment may include a bed cover 11 and a topper 12 on which a user's body is placed. A cushion module or assembly 20 may be provided under the topper 12. The cushion module 20 may alternative be referred to as a main body or mattress body, and the cushion module 20 and topper 12 may form a mattress or mattress set. The cushion module 20 may include a plurality of cushions C arranged in sections separated by at least one longer cushion or partition 40. The sections of the cushions C may correspond to individual firmness adjusters M1 described later. A plurality of firmness adjusters M1 may correspond to various areas of the bed that may be independently adjusted in firmness, while all of the cushions C in a particular firmness adjuster M1 may be adjusted uniformly or by one drive described later.

An adjustable bedframe 30 may be placed under the cushion module 20 to support the cushion module 20, and may alternatively be referred to as a mattress support or a motion controller. Portions of the bedframe 30 may be moveable so as to customize an overall shape or orientation of the bedframe 30. A safe guard or cover 13 may surround an edge of the bedframe 30 and cushion module 20 to protect the bedframe 30 and cushion module 20 from collisions. The safe guard 13 may be or include a box frame.

Hereinafter, "strength," "cushion strength," or "firmness" may be understood to mean a degree of softness or hardness of the bed. The firmness of the bed that a user prefers may vary depending on a user's age, physical condition, or simply taste or preference. For this reason, the bed 10 according to embodiments disclosed herein is characterized in that a user may adjust the firmness of the bed through manipulation of the cushion module 20.

The bed cover 11 may cover the topper 12 and surround the topper 12 and the safe guard 13. The bed cover 11 may alternatively be referred to as a cover sheet and may be optional. The bed cover 11 may have a size that completely surrounds upper and side surfaces of the safe guard 13 to define upper and side surfaces of the bed 10. Alternatively or in addition thereto, the bed cover 11 may be formed to cover a bottom of the bed 10.

In addition, the bed cover 11 may be made of or include an elastic material (e.g., a fitted sheet) so as to always maintain a taut or tensioned state. When the bed 10 is inclined or bent according to an operation of the bedframe 30, the bed cover 11 may be stretched. When the bedframe 30 returns to a flat state, the bed cover 11 may be contracted back to its original or initial state.

The user's body may lie on the bed cover 11 and/or the topper 12. The topper 12 may include an elastic foam (e.g., latex foam or memory foam) mattress or layer that is depressed by the user's weight and returns to its original or initial state when the load is removed.

The cushion module 20 may be an assembly or array of cushions C arranged in a grid form from a head of the bed 10 to a foot of the bed 10. The cushions C may extend vertically from a bottom of the bed 10 toward a top of the bed 10. The cushions C may have a cylindrical shape, but embodiments disclosed herein are not limited. Each cushion C may be provided in a cushion case 21. As an optional alternative, there may be some cushions C not provided in a cushion case 21 and coupled to the bedframe 30 (e.g., at a head or foot of the bedframe 30). In such an embodiment, a tension of the cushions C may be independently adjustable by hand, or each individual cushion C may have its own drive or motor. Embodiments disclosed herein are not limited.

The partition 40 may be interposed between adjacent cushion cases 21 at hinge points of the bedframe 30. A distance between adjacent cushions C and cushion cases 21 on opposite sides of a hinge point may be larger than a distance between adjacent cushions C and cushion cases 21 elsewhere. Such an arrangement may minimize interference between cushions C at the hinge point during an operation of the bedframe 30. When a user's body part lies at or near the hinge point, the partition 40 may provide support and/or cushioning the body part so that the user may feel more comfortable while lying down.

The safe guard 13 may prevent a user's leg or knee from colliding with the cushion module 20 or bedframe 30, which may cause pain or injury. The safe guard 13 may be formed of a soft or elastic material such as a sponge, latex foam, or memory foam. Alternatively, the safe guard 13 may be a box frame including a soft or elastic material provided at an outer side.

Figure 5:
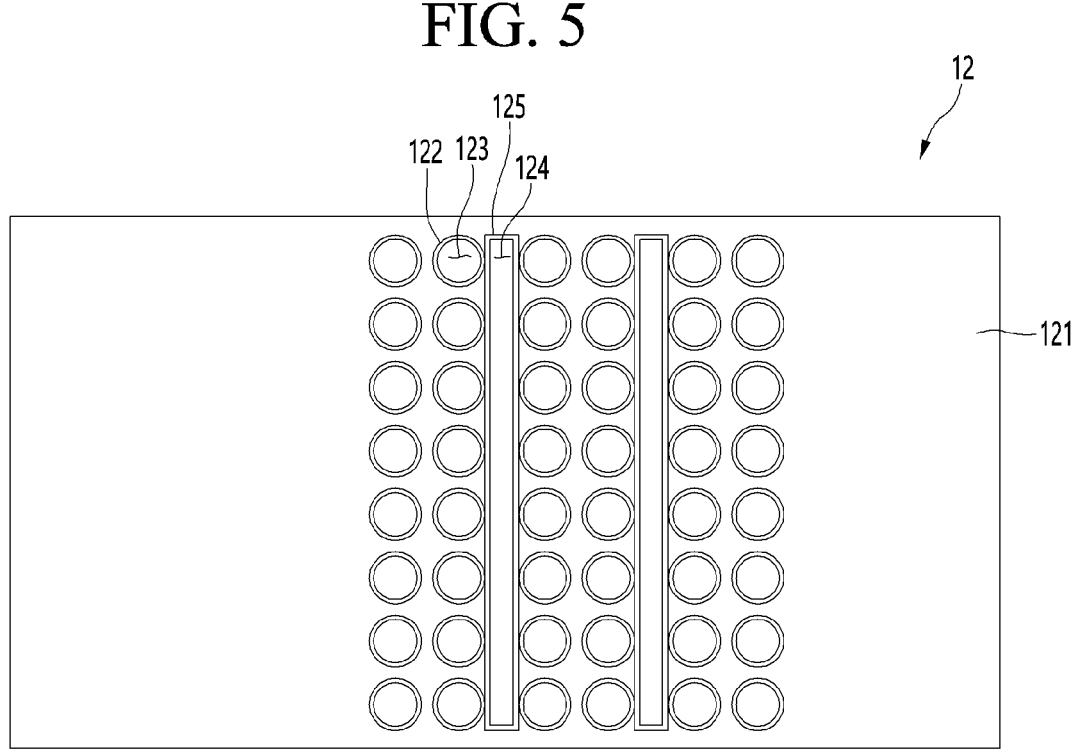
FIG. 5 is a bottom view of a topper of the bed of FIG. 1.
Figure 6:
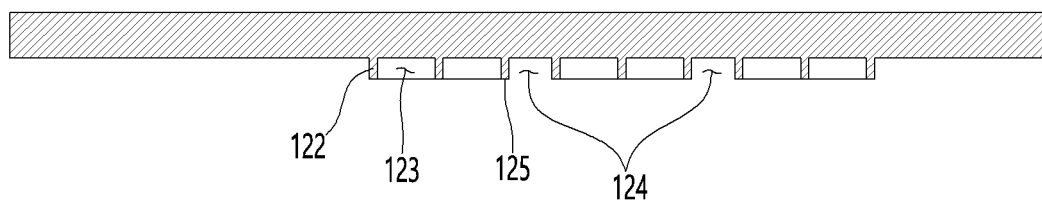
FIG. 6 is a longitudinal sectional view of the topper cut along 6-6 of FIG. 3.

Referring to FIGS. 5 and 6, a bottom surface of the topper 12 may contact an upper surface of the cushion C. The topper 12 may include a topper body 121 having a hexahedral shape or a shape that corresponds to a shape of the bedframe 13 (e.g., an elliptical or stadium shape for a cradle or daybed). The topper body 121 may have a predetermined thickness.

A cushion support sleeve 122 may extend from (or alternatively be formed within) a bottom surface of the topper body 121 to support sides of the cushion C. A cushion groove or recess may be formed by the cushion support sleeve 122, and an upper end of the cushion C may be inserted into the cushion groove 123. A partition support sleeve 125 may extend from (or alternatively be formed within) the bottom surface of the topper body 121 to support sides of the partition 40. A partition groove 124 may be formed by the partition support sleeve 124, and an upper end of the partition 40 may be inserted into the partition groove 124.

The cushion support sleeve 122 may have a hollow cylindrical shape or a shape corresponding to the cushion C such that an inner contour of the cushion support sleeve 122 corresponds to an outer contour of the cushion C. The partition support sleeve 125 may have a rectangular cross-sectional shape or a cross-sectional shape corresponding to a cross-sectional shape of the partition 40 such that an inner contour of the partition support sleeve 125 corresponds to an outer contour of the partition 40. The cushion and partition support sleeves 122 and 125 may secure the topper 12 to the cushion module 20 so as to prevent or reduce a movement or sliding of the topper 12 when the user gets on or off the bed during sleep, or during an operation of the bedframe 30. For example, the cushion and partition support sleeves 122 and 125 may be made of a rubber material configured to grip the cushion C and the partition 40, but embodiments disclosed herein are not limited.

Figure 7:
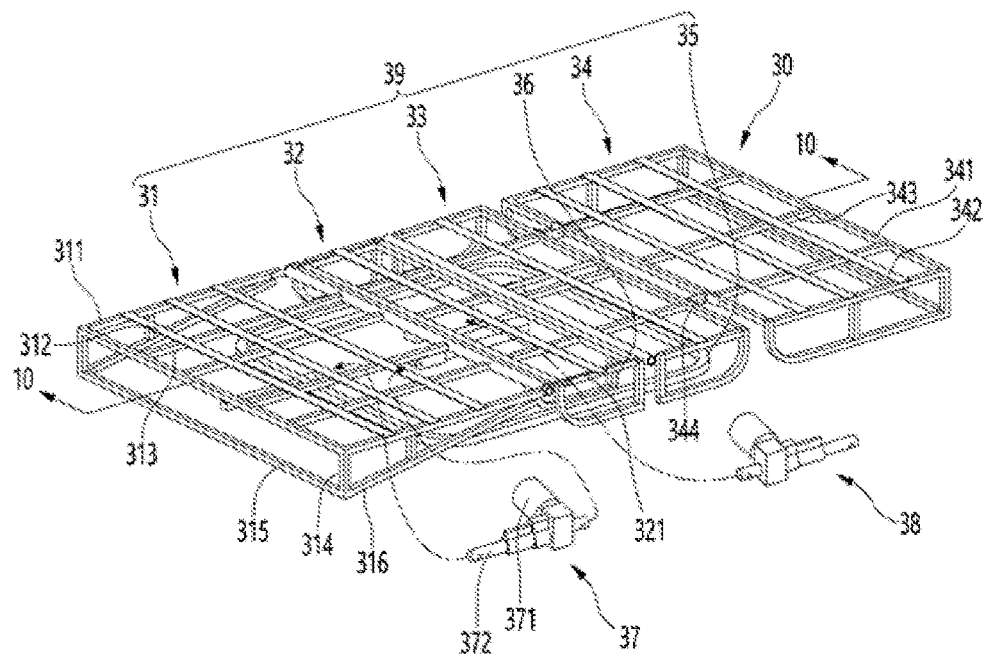
FIG. 7 is a perspective view from above of a bedframe constituting the bed of FIG. 1.
Figure 8:
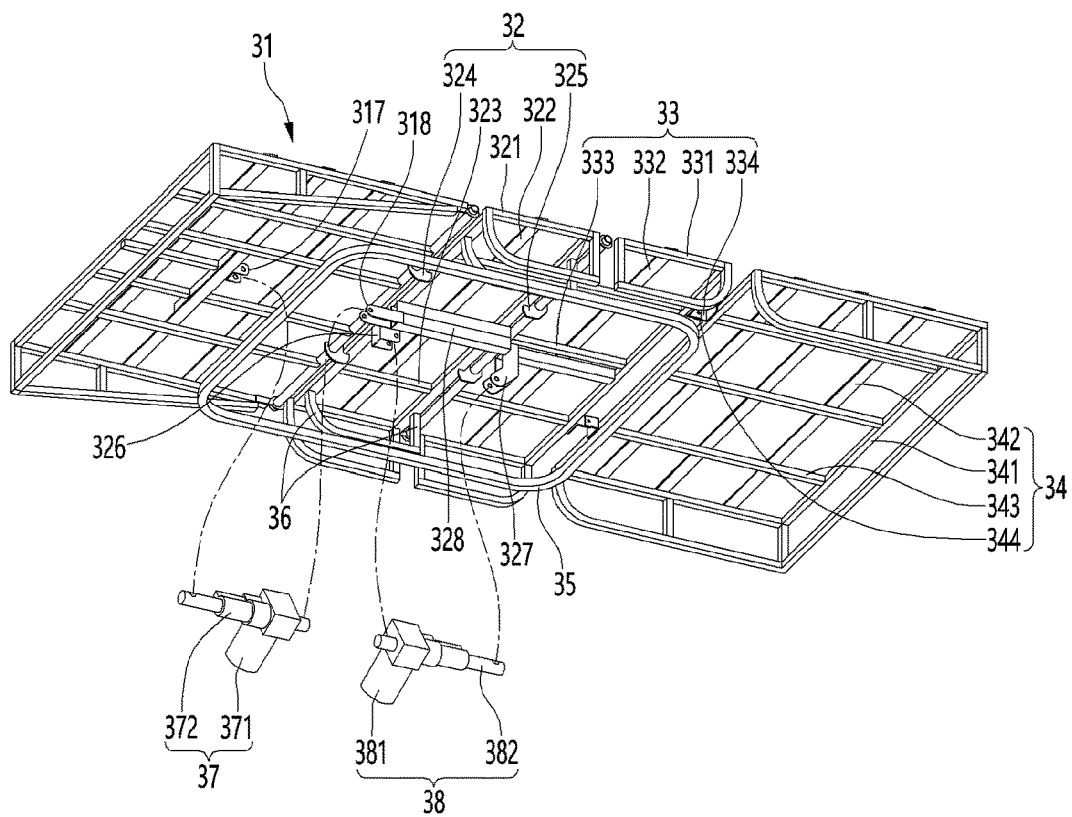
FIG. 8 is a perspective view of the bedframe as viewed from below.

Referring to FIGS. 7 and 8, the bedframe 30 may include a base or bottom frame 35 placed on an installation surface (e.g., a floor, a box spring, or bed platform, or a bigger bedframe). Alternatively, the base frame 35 may be a plate. A seating or upper frame 37 configured to move or change orientation may be provided above the bottom frame 35. The seating frame 39 may define an upper surface of the bedframe 30 on which the cushion module 20 is placed. A support frame or connection bar 36 may connect the base frame 35 and the seating frame 37.

Figure 10:
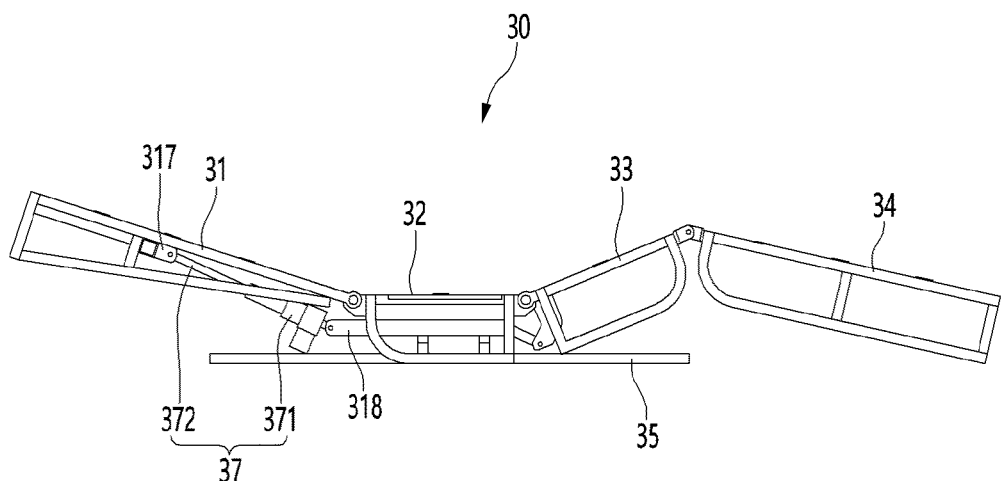
FIG. 10 is a side view of the bedframe in a state in which an upper body frame and a thigh frame are tilted upward.

The seating frame 39 may include a plurality of frames or supports configured to move, pivot, and/or incline relative to each other (see FIG. 10). The plurality of frames may be hinged to each other, but embodiments disclosed herein are not limited. For example, the seating frame 39 may include an upper body or main frame 31 configured to support a user's upper body or torso, a hip or bottom frame 32 configured to support a user's hip area, a thigh or upper leg frame 33 configured to support a user's thigh or upper leg, and a calf or lower leg frame 34 configured to support a user's calf or lower leg. The upper body, hip, thigh, and calf frames 31, 32, 33, and 34 may alternatively be referred to as upper body, hip, thigh, and calf supports. The upper body frame 31 may alternatively be referred to as a torso frame.

The seating frame 39 is not limited to upper body, hip, thigh, and calf frames 31, 32, 33, and 24. For example, there may be an optional headrest or neck and shoulder support configured to support a user's head, neck, and/or shoulders. Such an optional headrest may move, pivot, or incline with respect to the upper body frame 31. As another optional addition, there may be a lumber or lower torso support configured to support a user's lumbar and which may move, pivot, or incline relative to the upper body frame 31 (which may be a shoulder frame) and the hip frame 32.

A front or upper end of the upper body frame 31 (at a head of the bed 10) may be defined as a head of the bedframe 30, and a rear or lower end of the calf frame 34 (at a foot of the bed 10) may be defined as a foot of the bedframe 30. Here, a front-rear direction may be a direction extending between the head and foot of the bed 10. A rear end of the upper body frame 31 may be tiltably or rotatably connected (e.g., hinged) to a front end of the hip frame 32, and a front end of the thigh frame 33 may be tilted or rotatably connected (e.g., hinged) to a rear end of the hip frame 32. A rear end of the thigh frame 33 and a front end of the calf frame 34 may be connected to be relatively rotatable (e.g., via a shaft, pin, or hinge structure).

The upper body frame 31 may include an outer frame 311, a plurality of first plates or bars 312, and a plurality of second plates or bars 313. The first bars 312 may alternatively be referred to as left-right bars, upper bars, or cushion seating plates. The second bars 313 may alternatively be referred to as front-rear bars, lower bars, or connection bars.

The outer frame 311 may have a rectangular shape, a stadium, or a curved rectangular shape, and may define a front end (or head), a rear end, and both side ends (i.e., left and right ends corresponding to left and right sides of a lying human body) of the upper body frame 31. The plurality of second bars 313 may connect the front end and the rear end of the outer frame 311 and may be spaced apart from each other in the left-right direction of the outer frame 311. The plurality of first bars 312 may connect the left end and the right end of the outer frame 311 and may be spaced apart from each other in the front-rear direction of the outer frame 311. Accordingly, the plurality of second bars 313 and the plurality of first bars 312 may be arranged to be perpendicular to each other in a grid or lattice structure.

At the left and right corners of the front end of the outer frame 311, a pair of vertical bars 314 may extend in the vertical direction, and the pair of vertical bars 314 may be attached to the horizontal bar 315. An inclined bar 316 may extend from the lower end of each of the pair of vertical bars 314 to the rear end of the outer frame 311.

The pair of vertical bars 314 may transmit a vertical load applied to the outer frame 311 to the installation surface, thereby preventing the outer frame 311 from bending due to the vertical load. The vertical load may be understood as a combined load of a user's upper body, the cushion module 20, and a partial load of the topper 12.

The horizontal bar 315 may prevent the lower ends of the pair of vertical bars 314 from being bent in a direction away from each other or in a direction closer to each other due to the vertical load. The inclined bar 316 may prevent the pair of vertical bars 314 from bending forward or backward of the bedframe 30 due to the vertical load.

A frame portion or bar may function as a hinge axis or rotation center of the outer frame 311. A rotation center of the upper body frame 31 may be defined as an upper hinge axis. The upper hinge axis may be defined by a bar at a rear end of the outer frame 311 of the upper body frame 31.

An upper actuator 37 may be mounted on a bottom surface of the outer frame 311 to rotate the upper body frame 31 around the upper hinge axis. The upper actuator 37 may include a drive 371 and a plunger 372 that is extended or contracted by the drive 371. When the plunger 372 extends forward toward a front end of the upper body frame 31, the upper body frame 31 may rotate upward, and when the plunger 372 is retracted backward toward the rear end of the upper body frame 31, the upper body frame 31 may rotate downward.

A fastening flange may fix the upper actuator 37 to a bottom of the seating frame 39. The fastening flange may include a plunger fastening flange 317 to which a front end of the plunger 372 may be rotatably connected, and a drive fastening flange 318 to which a rear end of the drive 371 is rotatably connected.

In addition, the plunger fastening flange 317 may be formed on the bottom surface of the upper body frame 31, and the drive fastening flange 318 may be formed on the bottom surface of the hip frame 32. The plunger fastening flange 317 may be formed at a higher position than the drive fastening flange 318. A horizontal line (or horizontal plane) passing through the plunger fastening flange 317 and a horizontal line (or horizontal plane) passing through the drive fastening flange 318 may be spaced apart by a predetermined distance in the vertical direction.

With this structure, the plunger 372 may be provided to be inclined while the seating frame 39 may extend horizontally. When the plunger 372 is extended, the upper body frame 31 may rotate upward so as to bend with respect to the hip frame 32. If the plunger 372 is retracted in a horizontal state, the upper body frame 31 may not rotate smoothly upward.

The hip frame 32, like the upper body frame 31, may include an outer frame 321, at least one first bar or cushion seating plates 322, and a plurality of second bars or connection bars 323. The outer frame 321 may have a rectangular shape by four bars. A plurality of upper hinge shaft brackets 324 may be spaced apart from each other in the left-right direction on a bottom surface of a front end of the outer frame 321. A rear end of the upper body frame 31 may be installed through the plurality of upper hinge shaft brackets 324 so that the rear end of the upper body frame 31 may be rotatably connected to the front end of the hip frame 32.

The hip frame 32 may further include a load support bar 328 connecting a bottom of the front end and a bottom of the rear end of the outer frame 321. The drive fastening flange 318 may be connected to the front end of the load support bar 328. When the upper body frame 31 is tilted upward, the load support bar 328 may transmit a vertical load to the upper actuator 37 to prevent the drive fastening flange 318 from being pushed backward.

A lower actuator 38 may be mounted on the lower side of the hip frame 32 so that the rear end of the thigh frame 33 may be tilted in the vertical direction. Like the upper actuator 37, the lower actuator 38 may include a drive 381 and a plunger 382. A drive fastening flange 326 to which the drive 381 of the lower actuator 38 is rotatably connected may be provided at a bottom surface of the front end of the hip frame 32. A plunger fastening flange 327 to which an end of the plunger 382 of the lower actuator 38 is rotatably connected may be provided at the bottom surface of the front end portion of the thigh frame 33.

In addition, the drive fastening flange 326 may be positioned higher than the plunger fastening flange 327. The upper actuator 37 may be mounted on the bottom of the seating frame 29 such that the plunger 372 is inclined upward, and the lower actuator 38 may be mounted on the bottom of the seating frame 39 such that the plunger 382 is inclined downward.

The support frame 36 may extend to the bottom of the hip frame 32, and the lower end of the support frame 36 may be connected to the base frame 35. The base frame 35 may have a substantially rectangular shape and may have rounded corners, but a shape of the base frame 35 is not limited.

The support frame 36 may include a pair of frames extending downwards at left and right sides (or alternatively front and rear sides) of the hip frame 32. The pair of frames of the support frame 36 may be referred to as a left support frame and a right support frame. The lower end of the left support frame may be connected to the left side of the base frame 35, and the lower end of the right support frame may be connected to the right side of the base frame 35. The support frame 36 and the base frame 35 may be formed integrally as one body, but embodiments disclosed herein are not limited.

The bottom surface of the support frame 36 may pass through a same horizontal surface as the bottom surface of the base frame 35. When the bedframe 30 is placed on the installation surface, the support frame 36 and base frame 35 may prevent the bedframe 30 from shaking in the left-right direction. The support frame 36 may be further provided on the bottom of the hip frame 32 corresponding to the inner space of the base frame 35.

An optional frame or bar having a same shape as the support frame 36 may be provided on the left edge and the right edge of the hip frame 32, respectively. When a support frame having the same shape as the support frame 36 is further provided at the left and right edges of the hip frame 32, a vertical load acting from the topper 12 and the cushion module 20 may be transmitted to the installation surface, and bending or sagging of the left and right ends of the hip frame 32 may be reduced or prevented.

Figure 9:
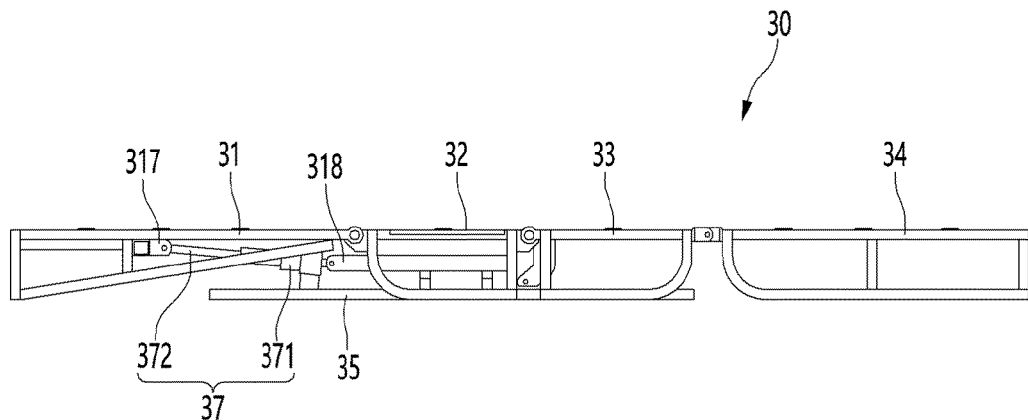
FIG. 9 is a side view of the bedframe in a horizontal state.

An optional support frame or bar having a same or similar shape as the support frame 36 may be formed at the left and right side ends of the thigh frame 33 and the left and right side ends of the calf frame 34, respectively, as shown. The optional support frame provided at the calf frame 34 is indicated in FIG. 9 as 34B.

A support structure defined by the vertical bar 314 and the horizontal bar 315 formed at the front end of the upper body frame 31 may be formed in the same manner at the rear end of the calf frame 34. A plurality of lower hinge shaft brackets 325 may be formed on the bottom surface of the front end of the hip frame 32. Like the plurality of upper hinge shaft brackets 324, the plurality of lower hinge shaft brackets 325 may be spaced apart from each other in the left and right direction of the hip frame 32.

A frame or bar defining a front end of the thigh frame 33 may pass through the lower hinge shaft bracket 325 so that the front end of the thigh frame 33 is at or adjacent to the rear end of the hip frame 32. The bar of the front end of the thigh frame 33 may be a rotation center of the thigh frame 33 and define as a lower hinge axis.

The thigh frame 33 may have a shape substantially symmetrical with the hip frame 32, but a shape of the thigh frame 33 is not limited. Front-rear lengths of the hip frame 32 and thigh frame 33 may be configured based on lengths of a human thigh and hip. For example, the thigh frame 33 may be longer than the hip frame 32 in the front-rear direction.

The thigh frame 33, like the hip frame 32, may have a rectangular outer frame 331, at least one first bar or cushion seating plate 332 extending across left and right ends of the outer frame, and a plurality of second or connection bars 333 connecting the front end and the rear end of the outer frame 331.

The plunger fastening flange 327 may be provided on the bottom of the front end of the thigh frame 33, and the plunger fastening flange 327 may be provided at an end of the plunger 382 of the lower actuator 38. A plurality of connection flanges 334 may extend at the rear end of the thigh frame 33. The plurality of connection flanges 334 may be formed on the left and the right sides of the rear end of the thigh frame 33.

Like the upper body frame 31, the calf frame 34 may include an outer frame 341, at least one first bar or cushion seating plate 342, and at least one second or connection bar 343. The outer frame 341 may have a substantially rectangular shape, and one or more cushion member seating plates 342 may be provided.

A plurality of first bars 342 may be provided on upper surfaces of left and right ends of the outer frame 341, and may be spaced apart in the front and rear direction of the calf frame 34. A plurality of second bars 343 may connect a front end and a rear end of the outer frame 341 and may be spaced apart in the left right direction of the calf frame 34.

A connection flange 344 having the same shape as the connection flange 334 formed on the rear end of the thigh frame 33 may be formed at the front end of the calf frame 34. The connection flange 334 of the thigh frame 33 and the connection flange 344 of the calf frame 34 may be rotatably connected.

Figure 11:
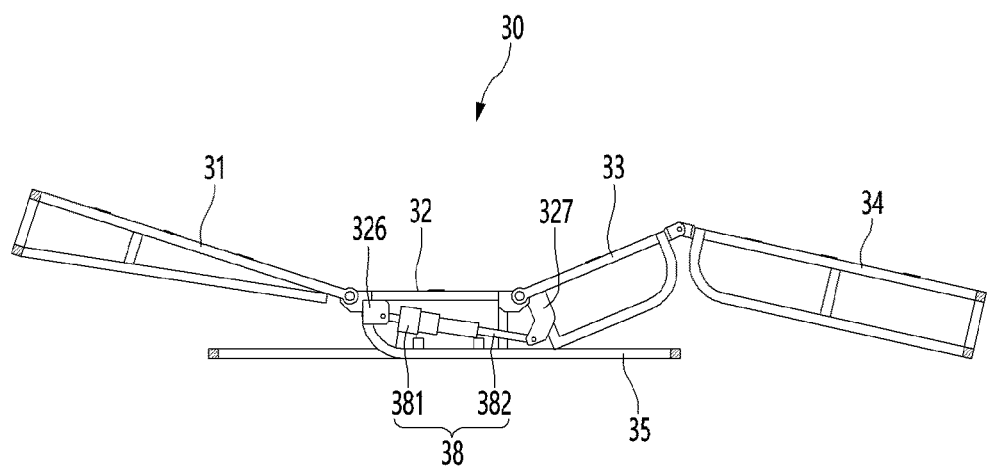
FIG. 11 is a side cross-sectional view of the motion controller cut along 11-11 of FIG. 7 in the state of FIG. 10.

Referring to FIGS. 9-11, when the upper body frame 31, the hip frame 32, the thigh frame 33, and the calf frame 34 lie in a same horizontal plane, the seating frame 39 and or bedframe 30 may be in a first or default state. The upper body frame 31 and/or the thigh frame 33 may be tilted a predetermined angle by an operation of the upper actuator 37 and/or the lower actuator 38 respectively, for use. FIG. 10 shows a state in which the plunger 372 of the upper actuator 37 is elongated while the upper body frame 31 is tilted upward and the thigh frame 33 is tilted upward. The hip frame 32 may be maintained in a horizontal state, and a load (or rotational moment) transmitted from the upper body frame 31 to the upper actuator 37, in addition to a load transmitted from the thigh frame 33 to the lower actuator 38, may be transmitted to the hip frame 32.

Two symmetrical rotational moments transmitted to the hip frame 32 may be countered or balanced by the base frame 35, which may reduce a possibility of the front or rear end of the base frame 35 being lifted up off the installation surface. A length of the base frame 35 may be sufficiently long in order to prevent the base frame 35 and thus the bed 10 from falling or tilting.

Figure 12:
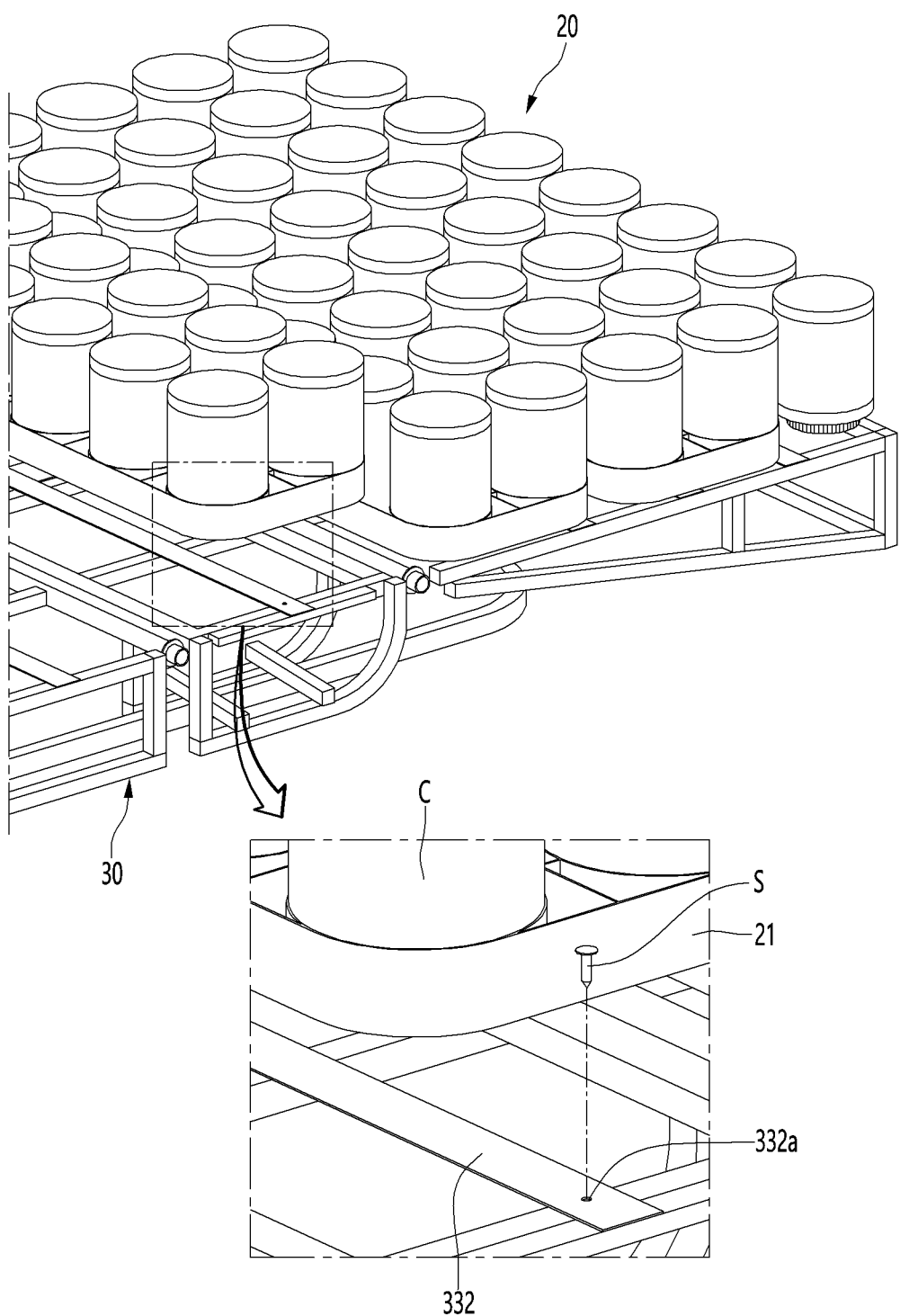
FIG. 12 is a view showing a coupling relationship between a firmness adjuster and the bedframe constituting the bed of FIG. 1.

Referring to FIG. 12, the cushion module 20 may be defined as an assembly of firmness adjusters M1 each having an array of cushions C arranged in a module or cushion case 21. The cushion case 21 may be placed on the first bars (also referred to as cushion seating plates) 312, 322, 332 and 342 provided on the upper surface of the bedframe 30. The first bars 312, 322, 332, and 342 may be located at a center of the bottom of the cushion case 21.

A fastening member S (e.g., screw or bolt) may be inserted into the first bars 312, 322, 332, 342 through a bottom of the cushion case 21 so that the cushion case 21 and cushions C may be coupled to the bedframe 30. A through hole through which the fastening member S passes may be formed in a center of a bottom of side ends of the cushion case 21. In addition, a fastening hole 332a through which the fastening member S passes may be formed at left and right edges of the first bars 312,322,332,342, so that the side ends of the cushion case 21 may be fixed to the first bars 312, 322, 332, and 342. An optional adhesive member (e.g., double-sided tape) may be provided on the upper surface of first bars 312,322,332,342 so that a bottom of the cushion case 21 may be further secured to the first bars 312,322,332,342.

Figure 13:
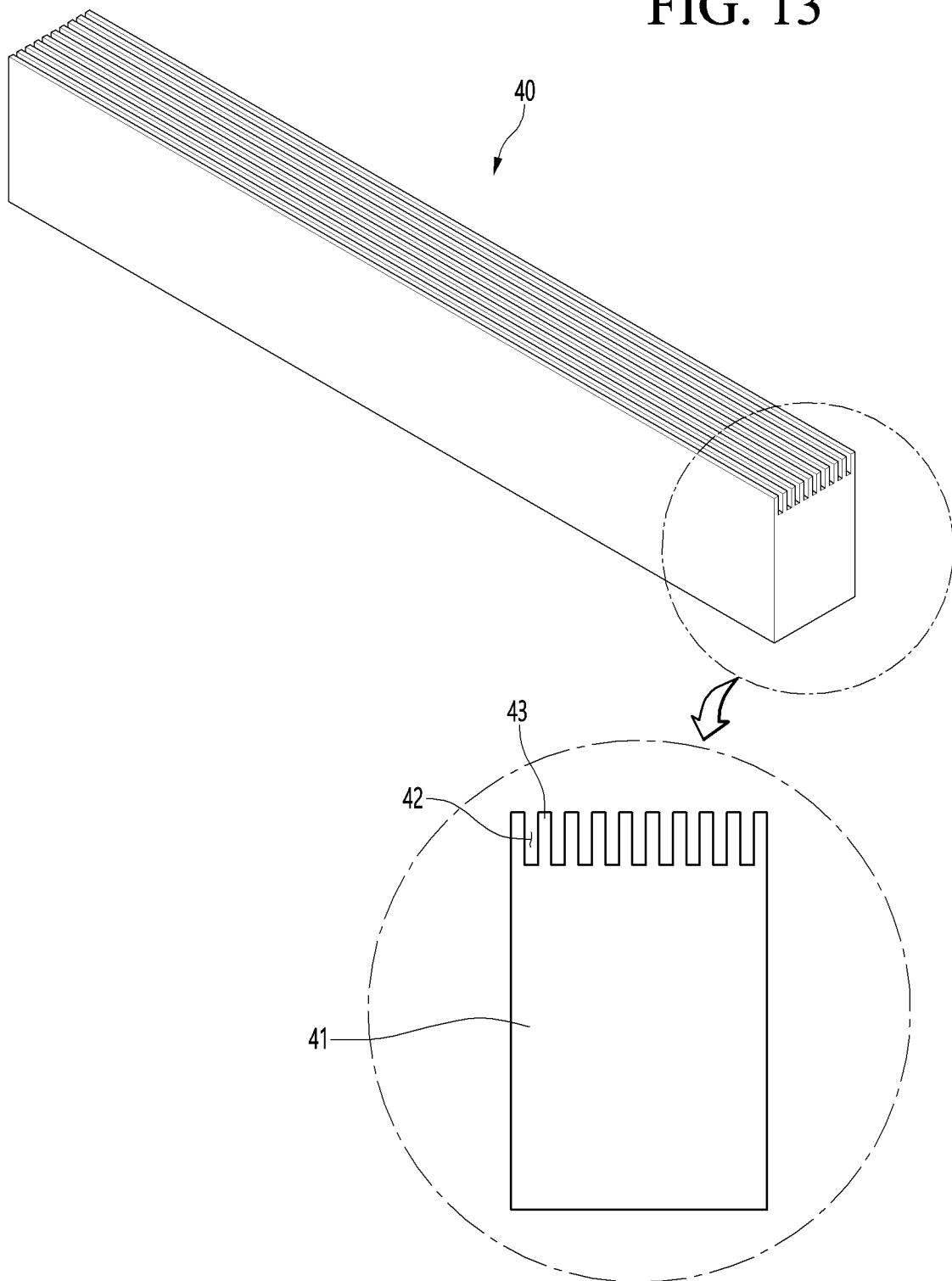
FIG. 13 is a perspective view of a partition or partition cushion according to an embodiment.

Referring to FIG. 13, at least one partition or wall 40 according to an embodiment may be interposed between adjacent cushion modules to prevent interference between adjacent cushion modules. The partition 40 may be provided at a hinge axis between adjacent frames of the bedframe 30.

There may be a plurality of partitions 40 lying along an upper hinge axis serving as a rotation center of the upper body frame 31, a lower hinge axis serving as a rotation center of the thigh frame 33, and at a hinge axis serving as a rotation center of the calf frame 34. Alternatively or in addition thereto, the calf frame 34 may rest on the relative rotating connection flanges 334,344.

A partition 40 provided between the upper body frame 31 and the hip frame 32 may be defined as a first partition. A partition 40 provided between the hip frame 32 and the thigh frame 33 may be defined as a second partition. A partition 40 provided between the thigh frame 33 and the calf frame 34 may be defined as a third partition.

When the upper body frame 31 is tilted upward, the cushion C at the rear end of the upper body frame 31 may approach an upper portion of the cushion C at the front end of the hip frame 32, and without a partition 40 therebetween, may contact the cushion C such that the cushions C become deformed and compressed. Similarly, when the thigh frame 33 is tilted upward, adjacent cushions C (one at the front end of the thigh frame 33 and one at the rear end of the hip frame 32) may approach each other, and, without a partition 40 therebetween, may contact and compress each other. By providing the first partition 40 between the upper body frame 31 and the hip frame 32 and the second partition 40 between the hip frame 32 and the thigh frame 33, during a bending motion of the upper body frame 31 and/or the thigh frame 33, the cushions C may press on and deform the partitions 40 instead of other cushions C.

The third partition 40 may have a thickness greater in the front-rear direction than a gap between a cushion C placed at a rear end of the thigh frame 33 and a cushion C placed at a front end of the calf frame 34. When the third partition 40 is sandwiched between the thigh frame 33 and the calf frame 34, the third partition 40 may be maintained in a compressed state when no external force is applied and/or the bedframe 30 is in the default state (i.e., a horizontal or flat state).

As the thigh frame 33 is tilted upward, the distance between the cushions C adjacent to the front and rear ends of the third partition 40 may increase. As a result, the third partition 40 may expand by a restoring force such that a front-rear thickness increases toward a natural thickness of the third partition 40. Since the rear end of the thigh frame 33 and the front end of the calf frame 34 may rotate relative to each other, a shape of the third partition 40 may be transformed or extended into a fan or wedge shape having a larger upper end thickness than a lower end thickness.

Each partition 40 may be made of the same material as the topper 12 or the safe guard 13, and thus a shape deformation may occur when an external force is applied. The partition 40 may return to an original state when the external force is removed.

The partition 40 may include a body 41, a plurality of slits 42 formed on an upper end of the body 41, and a plurality of fins 32 defined between the plurality of slits 42. The plurality of slits 42 may be formed at the upper end of the body 41 to facilitate a deformation of the upper end of the partition 40. The plurality of slits 42 and fins 43 may extend in the longitudinal direction of the partition 40 (a width direction or left-right direction of the bedframe 30). The slits 42 and fins 43 may alternate with each other along a thickness direction of the partition 40 (a length direction or front-rear direction of the bedframe 30.

Figure 14:
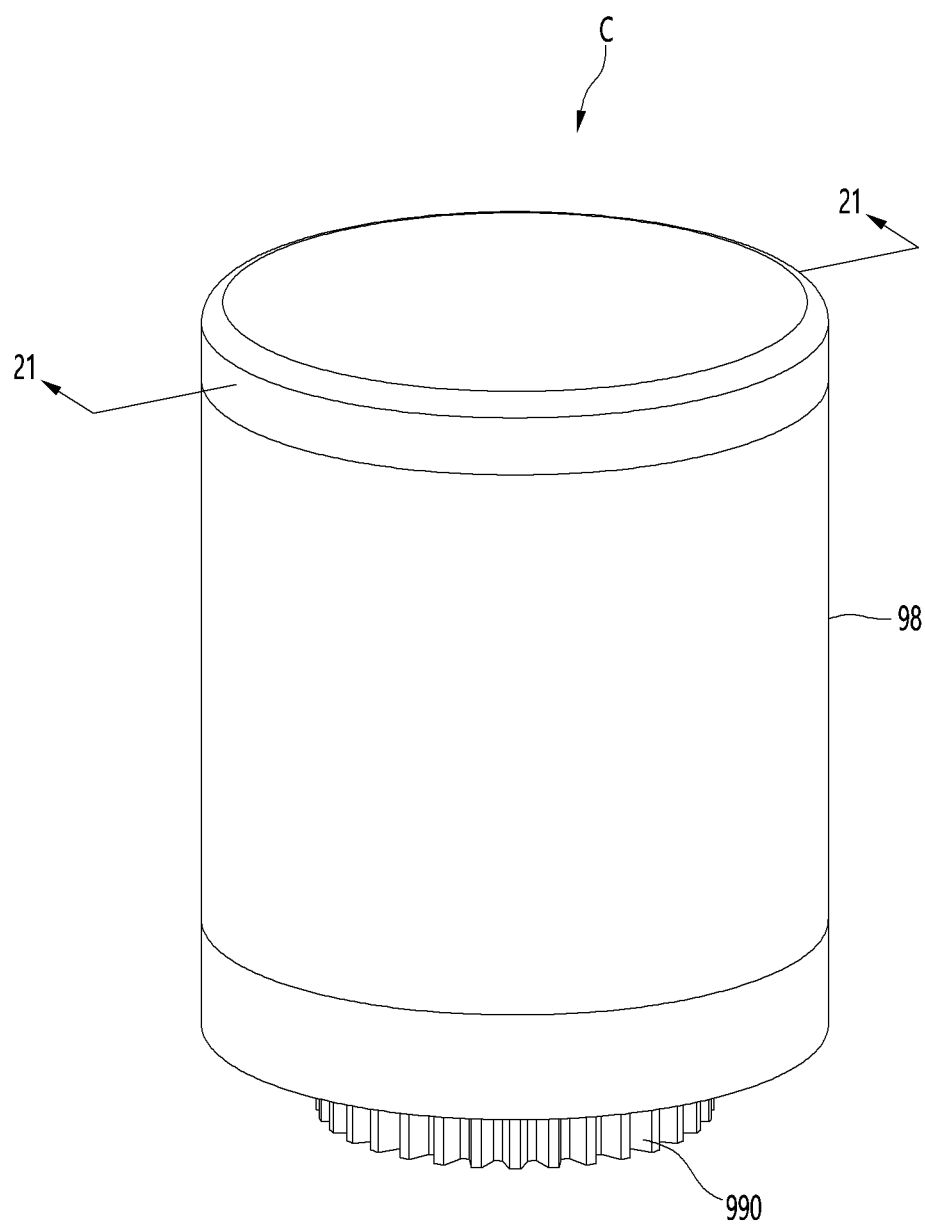
FIG. 14 is a front perspective view of a cushion according to an embodiment.
Figure 15:
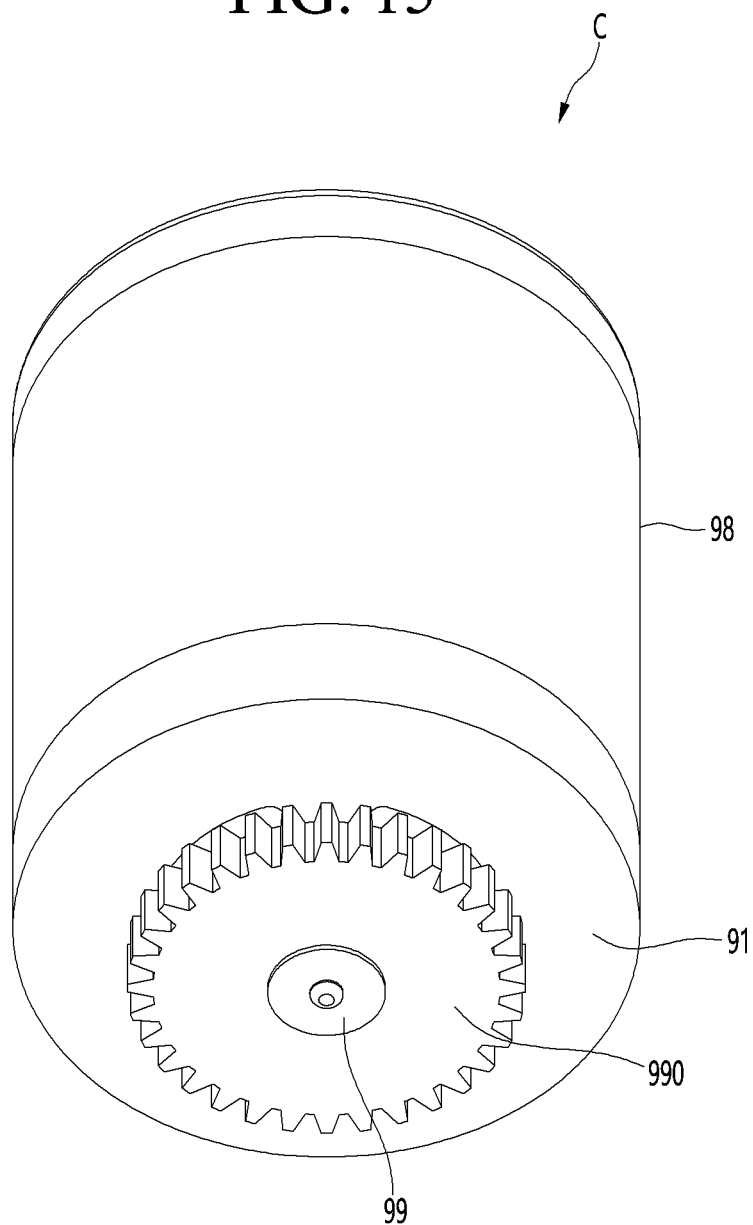
FIG. 15 is a bottom perspective view of the cushion.

Referring to FIGS. 14-16, the cushion C may have a cylindrical shape, but embodiments disclosed herein are not limited. For example, the cushion C may have a polygonal cylindrical shape.

Each cushion C may include an outer case 91, an inner case 92, an outer spring 93, an inner spring 94, and an upper cover 97, a lead screw 99, and a transmission gear 990. The cushion C may further include an inner spring cover 95, an outer spring cover 98, and a buffer or inner cover 96.

The outer and inner springs 93 and 94 may each include a coil spring wound in a spiral shape, but embodiments disclosed herein are not limited. For example, the outer and inner springs 93 and 94 may alternatively be accordion springs or made of a cushion or other elastic material.

The inner spring 94 may have a diameter smaller than that of the outer spring 93 and may have an elastic modulus or a spring constant smaller than that of the outer spring 93. An elastic strength of the inner spring 94 may be set or predetermined to be smaller than an elastic strength of the outer spring 93. The elastic strength or spring constant may be inversely proportional to an amount of deformation. For example, an amount of deformation of the inner spring 94 may be greater than that of the outer spring 93 with respect to a same applied axial force. As an alternative, the elastic strength or spring constant of the inner spring 94 and the outer spring 93 may be set or predetermined to be equal to each other.

A thread may be formed on an outer circumferential surface of the lead screw 99, and the transmission gear 990 may be coupled to a lower end of the lead screw 99. The lead screw 99 may be rotatably coupled to a center of a bottom of the outer case 91, and the inner case 92 may be screwed onto the outer peripheral surface of the lead screw 99. An inner surface of the inner case 92 may be optionally formed with screws to facilitate coupling to the lead screw 99. By a rotation of the lead screw 99 and a position of the inner case 92 within the outer case 91, the inner case 92 may rise or descend along the lead screw 99.

The inner spring cover 95 may surround the inner spring 94 and may include a thin fabric or an elastic material, but is not limited thereto. A shape of the inner spring cover 95 may be deformed according to an elastic deformation of the inner spring 94 and restored based on a restoration of the inner spring 94.

The outer spring cover 98 may surround the outer spring 93 and may be made of a same material as the inner spring cover 95, but embodiments disclosed herein are not limited to materials of the inner and outer spring covers 98 and 95. Like the inner spring cover 95, the outer spring cover 98 may be deformed or restored based on a deformation or restoration of the outer spring 93.

The buffer 96 may be mounted on a bottom surface of the upper cover 92, and an upper end of the inner spring 94 may contact a bottom surface of the buffer 96 to absorb shock and noise. For example, when the inner case 92 is lowered to a point where the upper end of the inner spring 94 is spaced apart from a bottom surface of the upper cover 97 and a vertical force acts or changes on the cushion C, the buffer 96 may absorb noise generated when the inner spring 94 hits a bottom surface of the upper cover 97.

Figure 17:
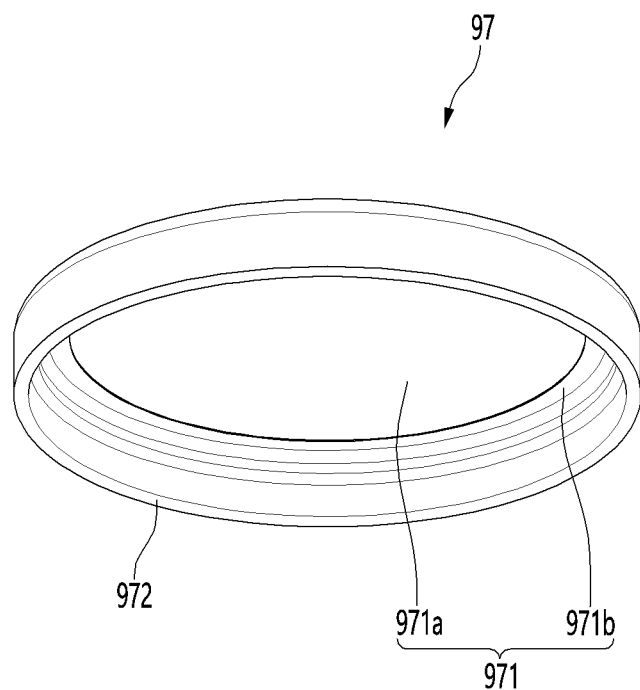
FIG. 17 is a bottom perspective view of an upper cover constituting a cushion according to an embodiment.

Referring to FIG. 17, the upper cover 97 may have a circular or polygonal cover plate or top plate 971, and a cover sleeve 972 extending downward from an edge of the cover plate 971. A buffer seating recess 971a may be formed on the lower surface of the cover plate 971 to be stepped upward. A bottom surface of the cover plate 971 corresponding to an edge of the buffer seating portion or recess 971a and an inner edge of the cover sleeve 972 may be defined as a spring seating portion or recess 971*b*. The upper end of the outer spring 93 may be seated on the spring seating recess 971*b*.

Figure 18:
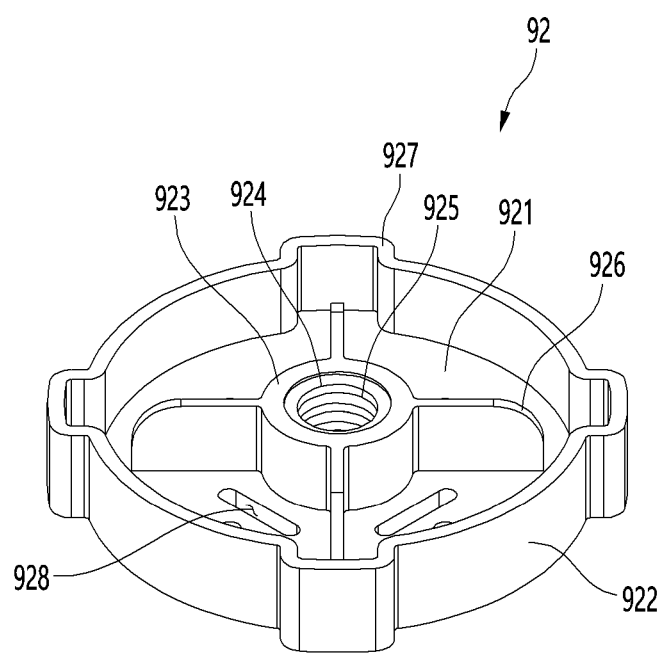
FIG. 18 is a perspective view of an inner case constituting a cushion according to an embodiment.

Referring to FIG. 18, the inner case 92 may include a base plate 921 having a circular or polygonal shape. A base sleeve 922 may extend upward from an edge of the base plate 921, and a screw boss 923 may extend upward from a center of the upper surface of the base plate 921.

The base sleeve 922 may have a plurality of guide protrusions 927 protruding in a radial direction, and the plurality of guide protrusions 927 may be spaced apart in a circumferential direction of the base sleeve 922. Each guide protrusion 927 may be formed by bending and extending the base sleeve 922. The guide protrusion 927 may include a pair of side surfaces or walls extending in a radial direction of the base plate 921 and facing each other, and a front surface or wall connecting the pair of side portions.

A screw hole 924 may be formed inside the screw boss 923, and a screw thread 925 may be formed on an inner circumferential surface of the screw hole 924. A plurality of reinforcing ribs 926 may extend radially outward from an outer circumferential surface of the screw boss 923. A lower end of the inner spring 94 may be provided in a space between outer ends of the plurality of reinforcing ribs 926 and an inner circumferential surface of the base sleeve 922. The plurality of reinforcing ribs 926 may reinforce a strength of the screw boss 923 and also reduce or prevent a movement of the inner spring 94 in the radial direction.

One or more holes or slits 928 may be formed in the base plate 921 at positions circumferentially between sides of the reinforcing ribs 926. The holes 928 may be formed to be closer to an outer surface of the screw boss 923 than outer ends of the reinforcing ribs 926, but embodiments disclosed herein are not limited.

Figure 19:
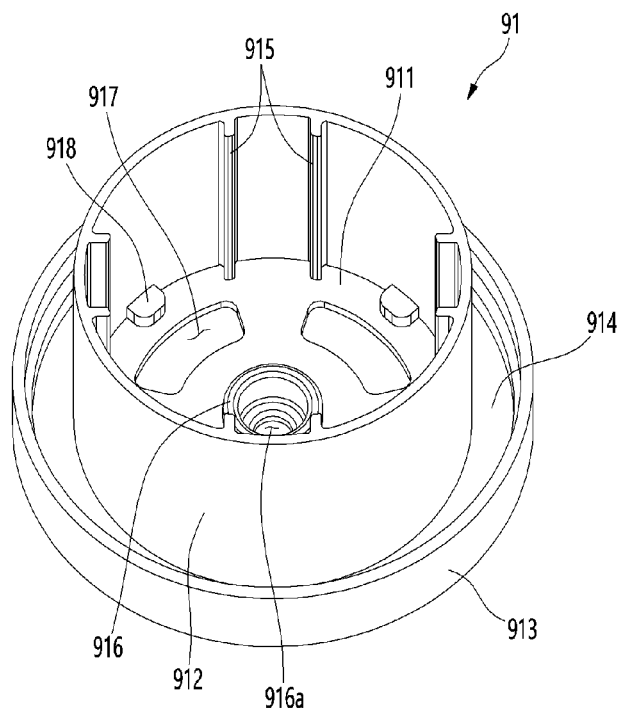
FIG. 19 is a perspective view of an outer case constituting a cushion according to an embodiment.

Referring to FIG. 19, the outer case 91 may include a bottom plate 911 having a circular or polygonal shape, and a case sleeve 912 extending upward from an upper surface of the bottom plate 911. The case sleeve 912 may have a diameter smaller than a diameter of the bottom plate 911.

A spring flange 913 may be bent and extended upward from an outer edge of the bottom plate 911, and the spring flange 913 may radially surround the case sleeve 912. The upper surface of the bottom plate 911 between the spring flange 913 and the case sleeve 912 may be defined as a spring mounting space or recess 914 in which a lower end of the outer sleeve 93 may be seated or mounted.

A pair of guide ribs 915 may extend radially inward from an inner circumferential surface of the case sleeve 912 to define a guide space. The guide ribs 915 in the pair of guide ribs 915 may be spaced apart in a circumferential direction of the case sleeve 912. A plurality of pairs of guide ribs 915 may further be spaced apart from each other along the circumferential direction.

The guide protrusions 927 of the inner case 92 (FIG. 18) may be fitted in the guide space between the pair of guide ribs 915. A position and number of guide spaces formed by the pair of guide ribs 915 may correspond to a position and a number of the guide protrusions 927.

A screw hole 916*a* may be formed in a center of the bottom plate 911. A support sleeve 916 may extend upward at an edge of the screw hole 916*a*. The lead screw 99 may pass through the screw hole 916*a*.

A plurality of air holes or slots 917 may be spaced apart from each other in a circumferential direction in the bottom plate 911. Each of the plurality of air holes 917 may be formed in a long hole or arc shape that curves to be round in the circumferential direction of the bottom plate 911, but a size or shape of the air hole 917 is not limited thereto. The air holes 917 may be provided at positions that are circumferentially between adjacent pairs of guide ribs 915 and/or at positions radially inward from the guide ribs 915, but embodiments disclosed herein are not limited.

A plurality of vibration preventing ribs 918 may protrude from an upper surface of the bottom plate 911 at an inner edge of the case sleeve 912. The vibration prevention ribs 918 may protrude radially inward from an inner peripheral surface of the case sleeve 912 toward a center of the bottom plate 911. A side of the vibration prevention rib 918 facing the center of the bottom plate 911 may be curved or rounded, and the vibration prevention rib 918 may have a semicircle or elliptical shape, but embodiments disclosed herein are not limited.

Figure 20:
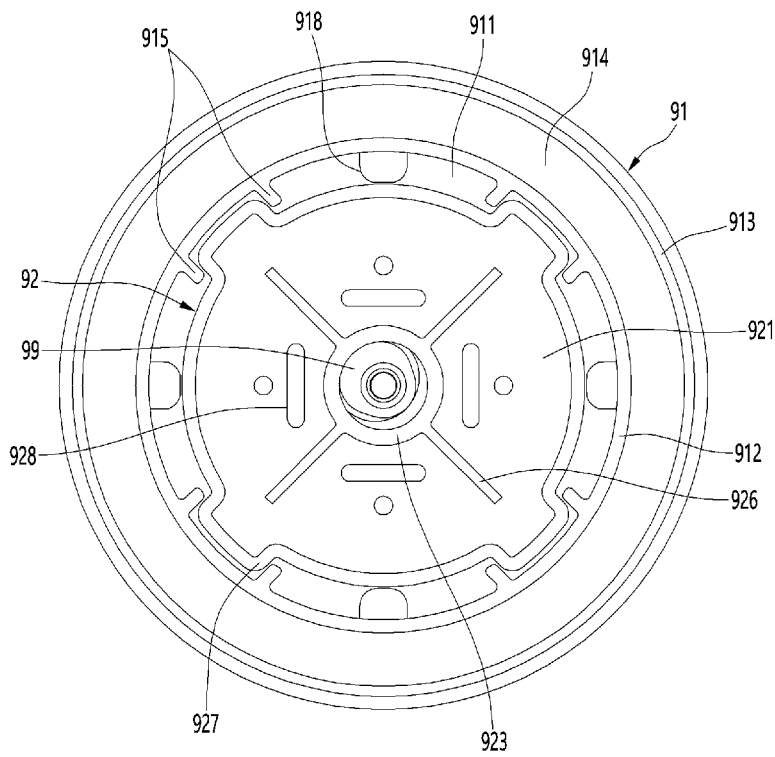
FIG. 20 is a plan view showing a state in which an outer case, an inner case, and a lead screw constituting a cushion are coupled.

Referring to FIG. 20, the pair of guide ribs 915 may contact side surfaces of the guide protrusions 927 formed on the inner case 92. The guide protrusion 927 may be supported by the guide rib 915 to prevent or reduce a spinning movement of the inner case 92 in the circumferential direction when the inner case 92 is raised or lowered.

When the inner case 92 descends to a bottom surface of the outer case 91, the vibration prevention rib 918 may contact an outer circumferential surface of the inner case 92 to prevent or reduce rattling of the inner case 92 along the radial direction and reduce or prevent noise.

Figure 21:
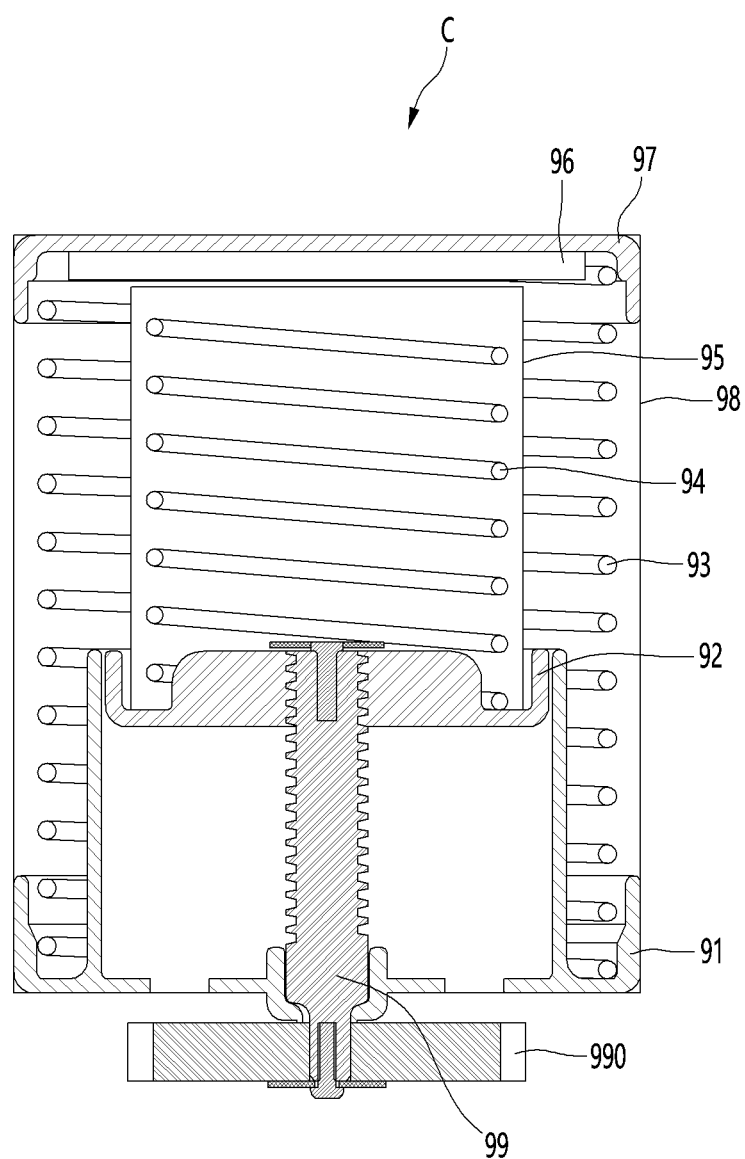
FIG. 21 is a longitudinal sectional view of the cushion cut along 21-21 of FIG. 14 in a state in which no external force is applied.
Figure 22:
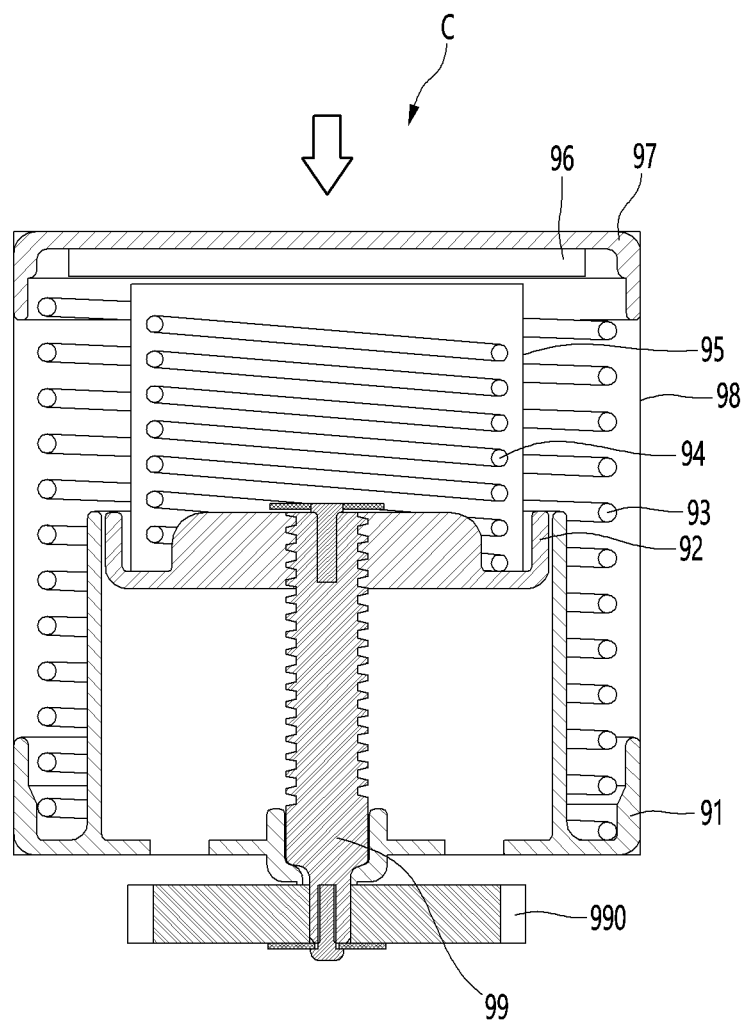
FIG. 22 is a longitudinal sectional view of the cushion member cut along 21-21 of FIG. 14 in a state in which an external force is applied.

Referring to FIGS. 21 and 22, the lead screw 99 may be rotated in a clockwise or counterclockwise direction to adjust a height of the inner case 92. In a basic state in which no external force is applied, the upper end of the inner spring 94 may or may not touch the buffer 96 depending on the height of the inner case 92.

When an external force in the vertical direction acts on the upper surface of the cushion C, the outer cover 97 may descend and compress the outer spring 93 and the inner spring 94 simultaneously, or, the outer spring 93 may be first compressed before the inner spring 94 and outer spring 93 are compressed together.

A firmness or cushion strength of the cushion C may be adjusted by adjusting a height of the inner spring 94. When the lead screw 99 is rotated in a direction that induces the inner spring 94 to be raised to have a height similar to a height of the outer spring 93, and the user sits on the bed, both the outer and inner springs 93 and 94 may be compressed. As a weight of the user acts on both the outer and inner springs 93 and 94, a deformation amount of each of the outer and inner springs 93 and 94 may be less than if all of the weight of the user acted on only one of the outer or inner springs 93 and 94. When the outer and inner springs 93 and 94 are compressed at a same time, the user may perceive an increased firmness. When the lead screw 99 is rotated such that the inner spring 93 is lowered so that a height of a top of the inner spring 94 is significantly below a height of the top of the outer spring 93, the weight of the user may act on the outer spring 93, a deformation amount of the outer spring 93 may be greater, and the user may perceive a decreased firmness. The upper cover 97 and/or inner cover 96 may prevent or reduce an uncomfortable feeling from a protruding end of the lead screw 99 when the inner spring 94 is lowered.

Figure 23:
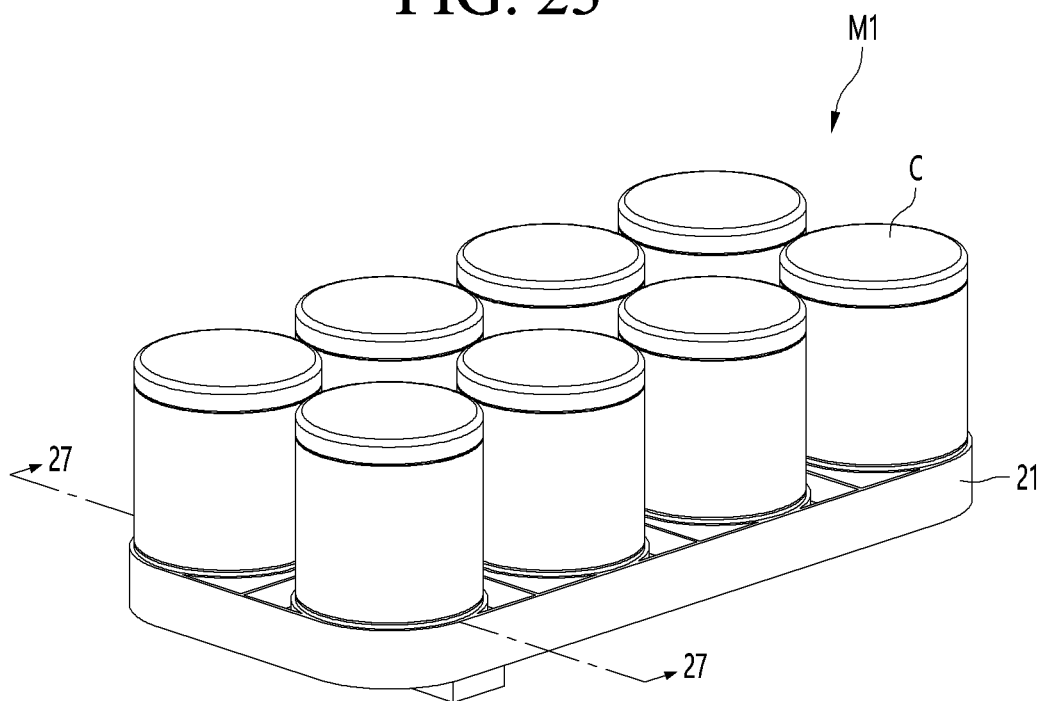
FIG. 23 is a side perspective view of a firmness adjuster according to an embodiment.
Figure 24:
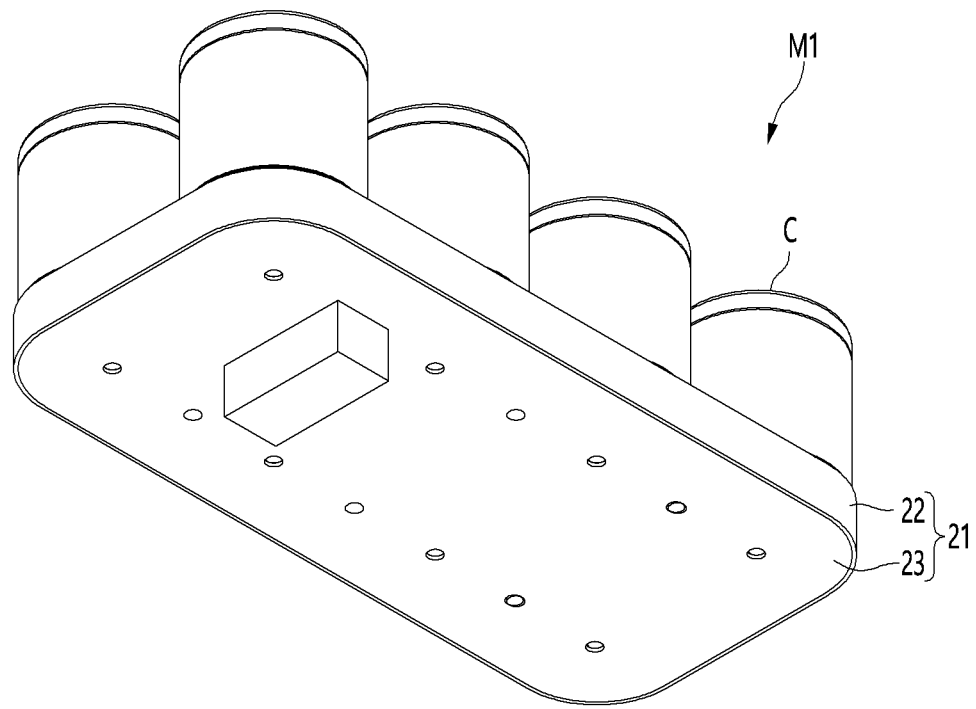
FIG. 24 is a bottom perspective view of the firmness adjuster according to an embodiment.

Referring to FIGS. 23 and 24, the cushion module 20 may include a plurality of firmness adjusters M1 each having a cushion case 21 and a plurality of cushions C arranged in the cushion case 21. The figures show that one firmness adjuster M1 may have eight cushions C, but embodiments disclosed herein are not limited to eight cushions C per firmness adjuster M1. The firmness adjuster M1 may include a drive 24 (e.g., motor or actuator) (See FIG. 25) to collectively and equally adjust an elastic strength of the cushions C.

There may be a plurality of firmness adjusters M1 corresponding to various areas of the bed. For example, there may be one firmness adjuster M1 for each of the upper frame 31, hip frame 32, thigh frame 33, and calf frame 34. As another example, there may be two firmness adjusters M1 for each of the upper, hip, thigh, and calf frames 31-34, one for each of the left and right sides of the upper, hip, thigh, and calf fames 31-34. Embodiments disclosed herein are not limited to an arrangement of firmness adjusters M1.

Figure 25:
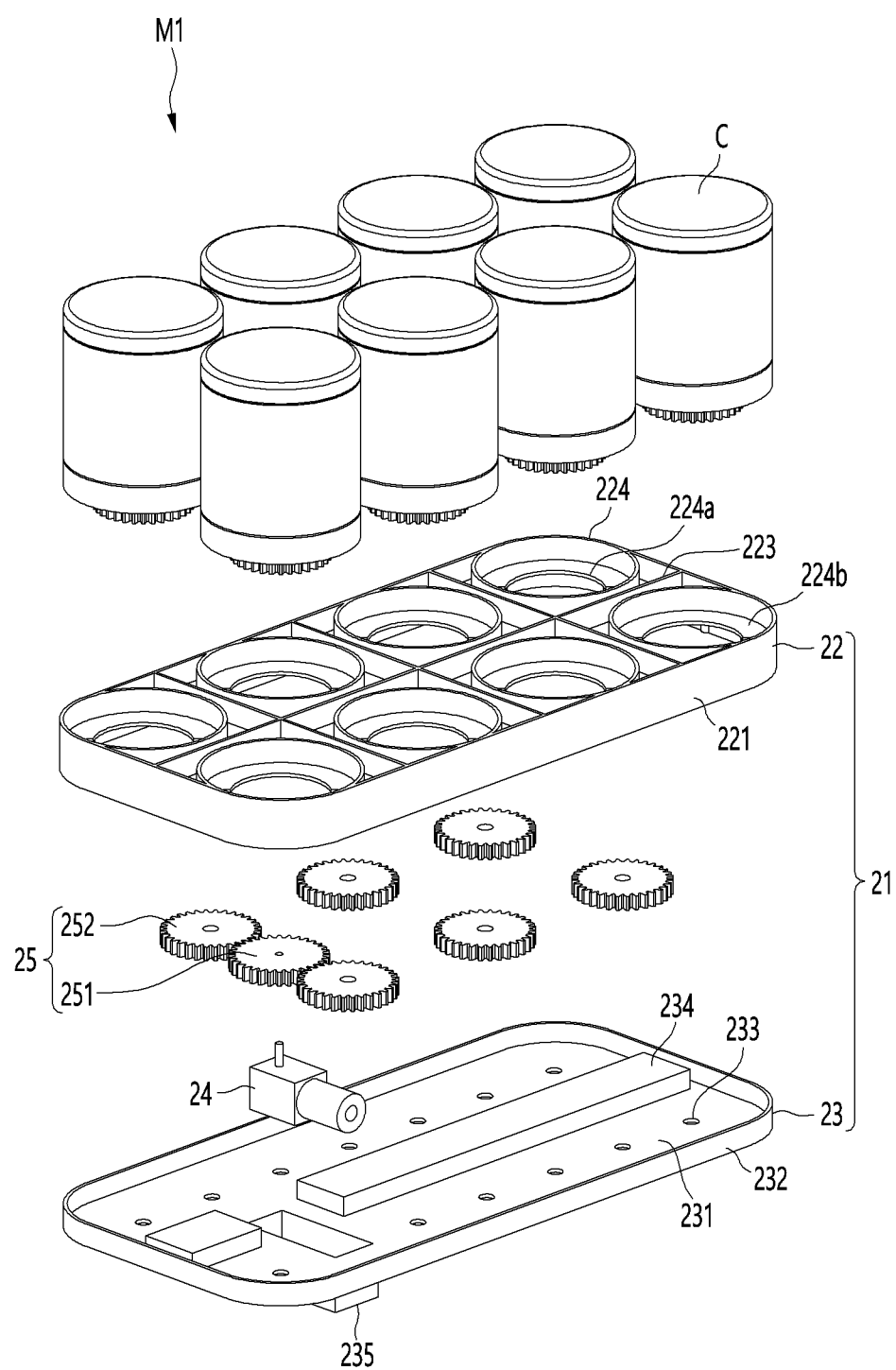
FIG. 25 is an exploded perspective view of a firmness adjuster according to an embodiment.

The module case 21 may include a bottom or outer case 23 and an upper or inner case 22. The drive 24 may be provided in a motor housing 235, which may be a recess or cavity formed in a bottom of the bottom case 23 (FIG. 25). The drive 24 may be provided between an upper surface of the bottom case 23 and a bottom surface of the upper case 22.

Figure 26:
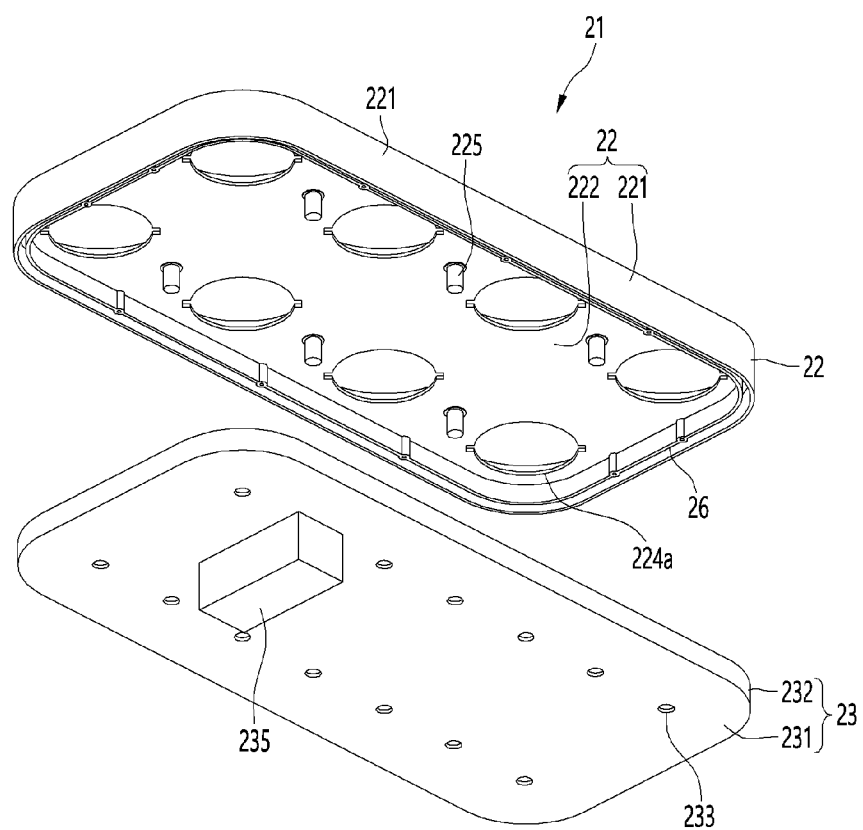
FIG. 26 is an exploded perspective view showing a bottom structure of a cushion case constituting the firmness adjuster.

Referring to FIGS. 25 and 26, the drive 24 may include a drive motor. For convenience of description, the drive 24 will be hereinafter referred to as a motor 24. A gear assembly 25 may be rotatably moveable by the motor 24. For example, FIG. 25 shows that a shaft may extend upward from the motor 24 to be rotatably coupled to a gear of the gear assembly 25. A plurality of other gears of the gear assembly 25 may engage with the gear rotated by the motor 24 to rotate. The motor 24 and gear assembly 25 together may be referred to as a rotational force transmission or transmitter that transmits a rotational force.

The upper case 22 may include an outer frame or wall 221 formed in a rectangular shape with a predetermined height, and an inner plate 222 formed inside the outer wall 221. The inner plate 222 may be provided a predetermined distance upward from a lower end of the outer wall 221 to divide the inner space of the upper case 22 into an upper space and a lower space. The gear assembly 25 may be provided in the lower space of the upper case 22, and the plurality of cushions C may be provided in the upper space of the upper case 22.

A plurality of gear shafts 225 may protrude from the bottom surface of the inner plate 222 so that gears G to be described later may be rotatably mounted. A plurality of partition plates or walls 223 may protrude from the upper surface of the inner plate 222 to divide the upper space of the outer frame 221 into a plurality of small spaces in which the cushions C may be provided.

The plurality of partition plates 223 may include a plurality of horizontal or first partition plates 223 extending in the width direction of the upper case 22 and arranged at equal intervals in the length direction, and at least one vertical or second partition plate 223 extending in the length direction of the upper case 22. The second partition plate 223 may divide the upper space of the outer frame 221 into left and right sides.

A number of second partition plates 223 may be determined according to a number of rows (extending in the front-rear direction) in which the plurality of cushions C are arranged, and the number of first partition plates 223 may be determined according to a number of rows or columns (extending in the left-right direction) in which the plurality of cushions C are arranged.

A support sleeve or flange 224 may extend in each of a plurality of small spaces partitioned by the first and second partition plates 223, and a through hole 224a may be provided in the inner plate 222 at an inner side of the support sleeve 224. The support sleeve 224 and the partition plates 223 may have a same or similar height, and an inner diameter of the support sleeve 224 may be formed to have a size corresponding to an outer diameter of the cushion C.

The through hole 224a may have a diameter smaller than an inner diameter of the support sleeve 224. A seating surface 224b may be formed on the upper surface of the inner plate 222 at an inner bottom of the support sleeve 224 to support an outer edge of the cushion C.

A diameter of the through hole 224a may have a size corresponding to or slightly bigger than that of an outer diameter of the transmission gear 990 so that when the cushion C is seated inside the support sleeve 224 on the seating surface 224b, the transmission gear 990 may be exposed through or pass through the through hole 224a to the lower space of the outer frame 221.

Meanwhile, a seal 26 or gasket may be provided at an edge of the lower space of the upper case 22 to reduce or prevent an inflow of foreign matter through a coupling portion or area between the bottom case 23 and the upper case 22. The seal 26 may also reduce or prevent noise (e.g., noise of the gear assembly 25) generated in the lower space of the outer frame 221.

The bottom case 23 may include a bottom plate 231 and a side wall 232 extending upward from an edge of the bottom plate 231. The side wall 232 may contact the inner circumferential surface of the outer frame 21 defining a lower space of the upper case 22. The seal 26 may contact an upper end of the side wall 232 and/or may be fitted between an outer circumferential surface of the upper end of the side wall 232 and the inner circumferential surface of the outer wall 221. Alternatively, the side wall 232 may fit in a space between the seal 26 and the outer wall 221.

The seal 26 may be made of an elastic, rubber, or plastic material, and may extend downward from the bottom surface of the upper case 22. The seal 26 may be provided at an inner side of the outer wall 221 and extend along an outer side or perimeter of the bottom surface of the upper case 22.

A plurality of shaft holes 233 may be formed in the bottom plate 231 at positions below or aligning with the plurality of gear shafts 225. Alternatively, the shaft holes 223 may be omitted, and a length of the gear shaft 225 may correspond to a depth of the lower space of the upper case 22 (i.e., a distance between the bottom surface of the inner plate 222 and the bottom plate 231). As another alternative, the shaft holes 223 may instead be formed by recessing an upper surface of the bottom case 23 downward.

A motor housing 235 to house the motor 24 may protrude from a bottom surface of the bottom plate 231. The motor housing 235 may be formed such that a portion of the bottom plate 231 is recessed or stepped downward by a predetermined depth. Alternatively, a communication hole may be formed in the bottom plate 231, and a separate housing may be coupled to a bottom of the bottom plate 231 at a position directly below the communication hole to define the motor housing 235.

The gear assembly 25 may include a drive gear 251 driven by the motor 24 and at least one driven gear 252 configured to engage with and be driven by the drive gear 251. The transmission gears 990 of the cushions C may be adjacent to the driven gears 252. There may be idle gears not part of the cushions C that are provided between adjacent transmission gears 990 so as to transmit a rotational force to the transmission gears 990 that are part of the same firmness adjuster M1. Alternatively, when there is a plurality of driven gears 252, all of the plurality of driven gears 252 may be defined as idle gears. As another alternative, there may be one driven gear 252 and a plurality of idle gears. Embodiments disclosed herein are not limited to an arrangement of the gear assembly 25 and the transmission gears 990.

The gear shaft 225 may extend from the bottom surface of the inner plate 222. Alternatively, the gear shaft 225 may extend upward from the top surface of the bottom plate 231.

A spacer 234 may be provided in a center of the bottom plate 231 in a space between two rows of transmission gears 990 that extend in a length direction of the cushion case 21. The spacer 234 may be a panel or frame extending in the length direction, but embodiments disclosed herein are not limited.

The spacer 234 may prevent the driven gears 252 or idle gears from being moved in a width direction of the module case 21 and disrupting a gear coupling of the gear assembly 25 and the transmission gears 990. The spacer 234 may have a height corresponding to a gap between the inner plate 222 and the bottom plate 231, and may prevent or reduce sagging of the inner plate 222. The spacer 234 may optionally be configured to add structural rigidity to the cushion case 21.

Figure 27:
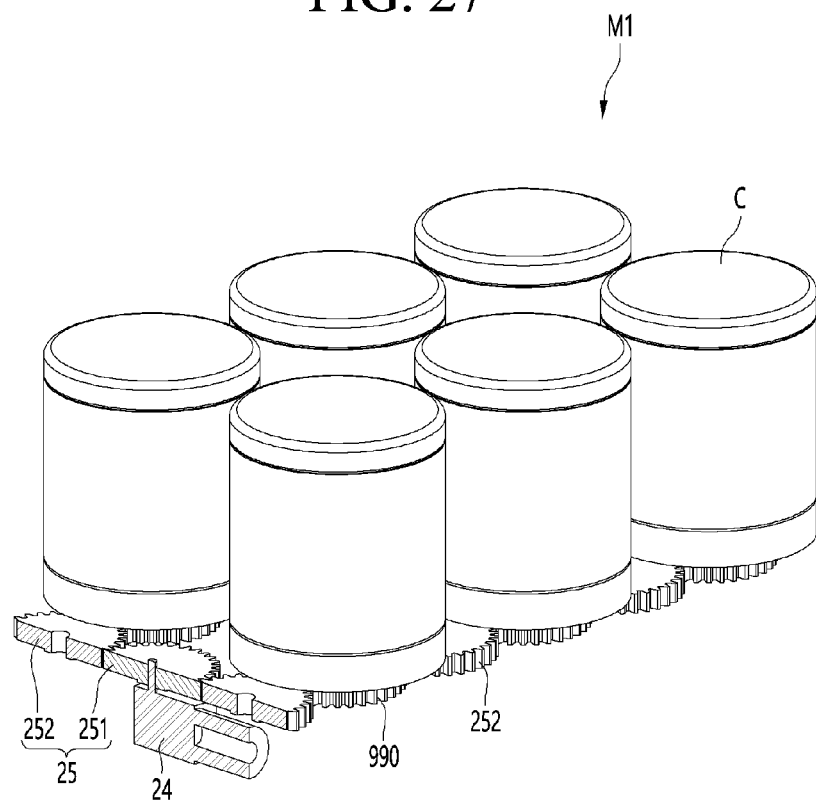
FIG. 27 is a cut-away perspective view of a bedframe taken along 27-27 of FIG. 23.
Figure 28:
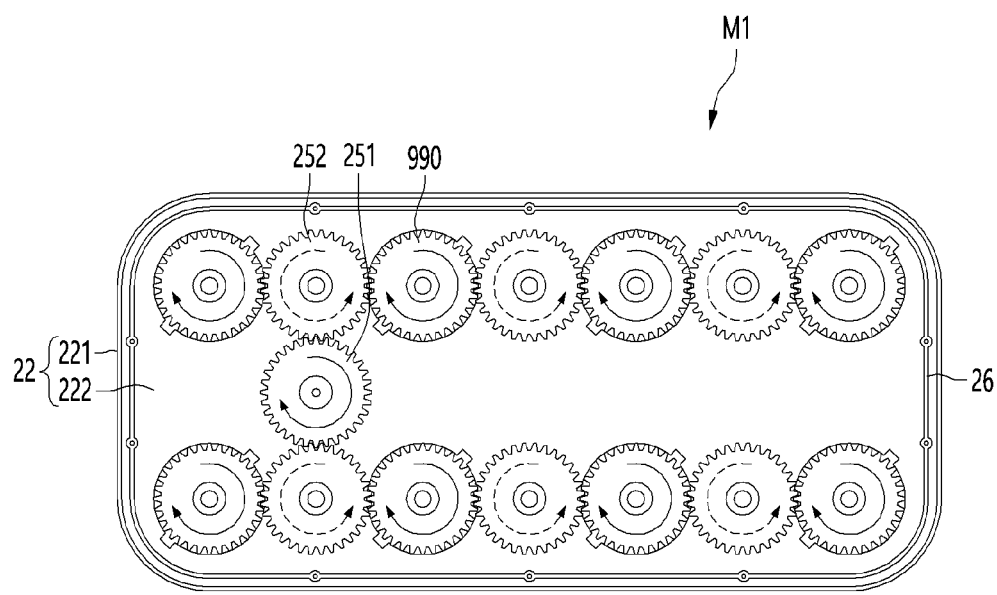
FIG. 28 is a bottom view of the firmness adjuster according to an embodiment from which a bottom case is removed.

Referring to FIGS. 27 and 28, the transmission gears 990 and the driven gears 252 may be alternately arranged with each other, and all of the transmission gears 990 may rotate in the same direction. A rotational force supplied from the motor 24 may be transmitted to the driven gear 252 through the driving gear 251, and the rotational force transmitted to the driven gear 252 may be transmitted to a transmission gear 990 and subsequent transmission gears 990 via other driven gears 252 or idle gears. For convenience of description, a gear directly connected to the drive gear 251 may be defined as the driven gear 252, while a gear provided between adjacent transmission gears 990 may be defined as the idle gear.

The drive gear 251 may be engaged with a driven gear row located at an outer side or end (e.g., a front end) of the cushion case 21, but embodiments disclosed herein are not limited. For example, the motor 24 and motor housing 235 may be provided at a center of the bottom case 23, and the drive gear 251 and driven gear 252 may be provided in a middle or center portion of the bottom case 23, with idle gears provided at either side or end.

When a firmness for a particular area of the bed is set through a user interface (e.g., provided in the bedframe 30, safe guard 13, remote controller 800 described later or on a mobile or web application, the motor 24 of a corresponding firmness adjuster M1 may rotate, a rotational force may be transmitted to the gear assembly 25, and the plurality of cushions C in a same firmness adjuster M1 may be controlled to have a same elastic strength. The user may desire that a firmness of the bed be uniform, in which case, all of the firmness adjusters M1 may be controlled such that all of the cushions C have the same firmness.

In addition, although the Figures show a 2×4 arrangement of the cushions C in each firmness adjuster M1, embodiments disclosed herein are not limited to such a number or arrangement and may be customized, along with a size of the cushions C and an overall size of the firmness adjuster M1. When a plurality of cushions C are provided in one row, one driven gear 252 may be connected to the driving gear 251. When three or more rows of cushions C are provided, if idle gears are provided between adjacent driven gears 252, a firmness of three or more rows of cushions C can be controlled with one motor 24.

Figure 29:
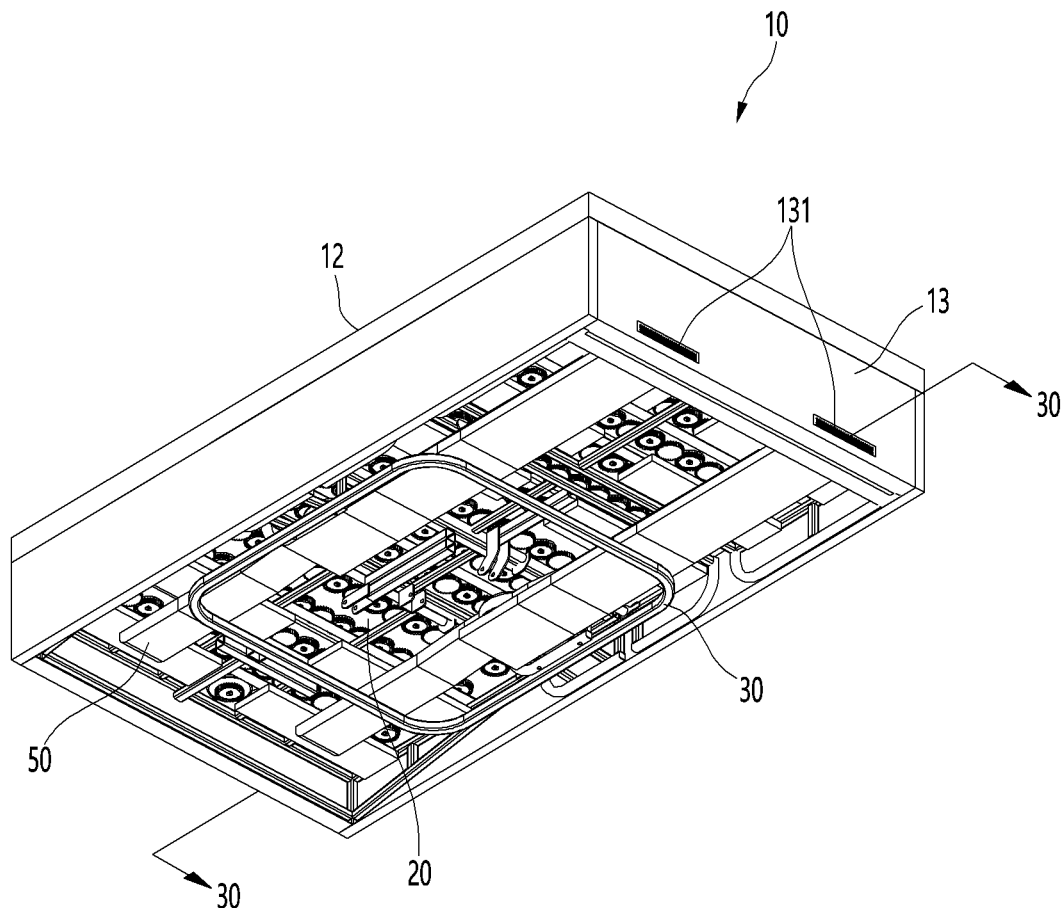
FIG. 29 is a bottom perspective view of the bed of FIG. 1 provided with a drying module or dryer.
Figure 30:
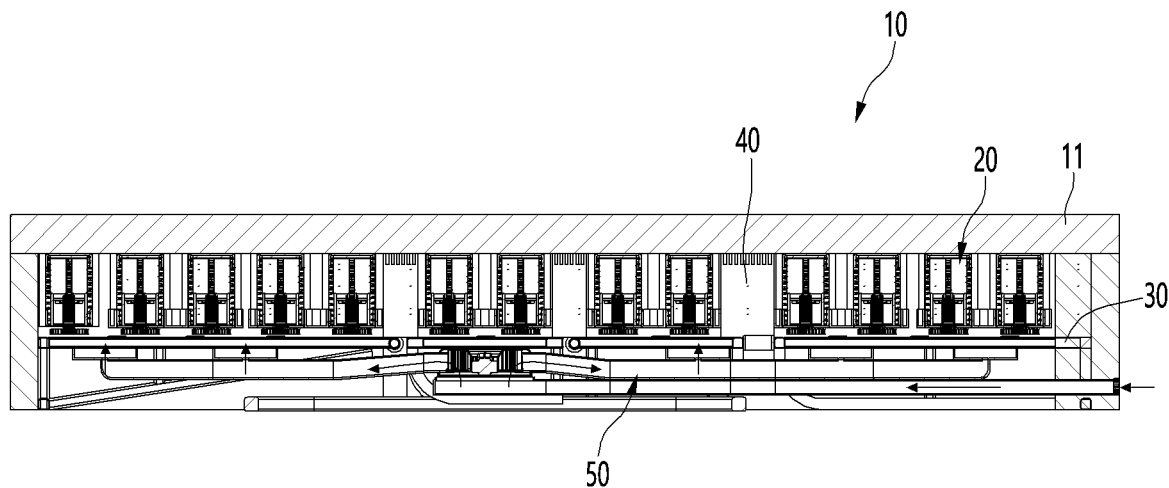
FIG. 30 is a longitudinal sectional view of the bed cut along 30-30 of FIG. 29.

Referring to FIGS. 29 and 30, a drying module 50 that supplies air or fluid to dry the topper 12 may be mounted on a bottom of the bed 10 (e.g., at a bottom of the cushion module 20 or bedframe 30) according to an embodiment. An inlet 131 to suction ambient air may be formed in the safe guard 13 at the foot of the bed 10. Alternatively, the inlet 131 may be formed in the safe guard 13 provided near the head of the bed 10; however, since user's tend to push a head of their bed against a wall, an inlet 131 provided at the foot may be better to suction the air. Embodiments disclosed herein are not limited to a position of the inlet 131. The inlet 131 may be positioned in consideration of an installation condition of the bed 10 or a layout of a bedroom. As another example, there may be a plurality of inlets 131 provided in the safe guards 13 at both the head and the foot of the bed, and the inlets 131 may be provided near corners and/or near lower ends of the safe guards 13.

The inlet 131 may be connected to an air intake passage or duct (e.g., suction duct 52 described later) formed in the drying module 50. Air introduced into the drying module 50 through the inlet 131 may be discharged toward the topper 12 through an indoor air discharge hole or outlet formed in the drying module 50. A structure of the drying module 50 will be described in more detail with reference to FIG. 31, but as seen in FIGS. 29 and 30, the drying module 50 may be configured as hollow extensions extending lengthwise under left and right sides of the bed and communicating with the inlets 131, and outlets may be formed in an upper surface of the long rectangular extensions. Each extension of the drying module 50 may include a fan to suction air. Embodiments disclosed herein are not limited, and various drying modules are disclosed in co-pending U.S. application Ser. No. 17/090,062 filed on Nov. 5, 2020, the entire contents of which are incorporated by reference herein.

As shown in FIG. 30, a plurality of outlets may be formed in the drying module 50 to face the topper 12. Air may be discharged upward from the drying module 50, pass through the cushion module 20, and flow toward the topper 12 to dry the topper 12.

Since the topper 12 may be formed of a porous latex or memory foam, some of the air hitting the bottom of the topper 12 may pass through the topper 12. The rest of the air hitting the topper 12 may be diffused to an edge of the bottom surface of the topper 12 and rise along a side of the topper 12. The air rising along the side of the topper 12 may flow through a space between the bed cover 11 and a top surface of the topper 12 to evaporate moisture that has penetrated the top surface of the topper 12.

The outlet of the drying module 50 may not contact a bottom surface of the cushion module 20 or bedframe 30. Air discharged through the outlet may rise through a plurality of gaps formed in the cushion module 20 and may be evenly distributed over the entire bottom of the topper 12.

Figure 31:
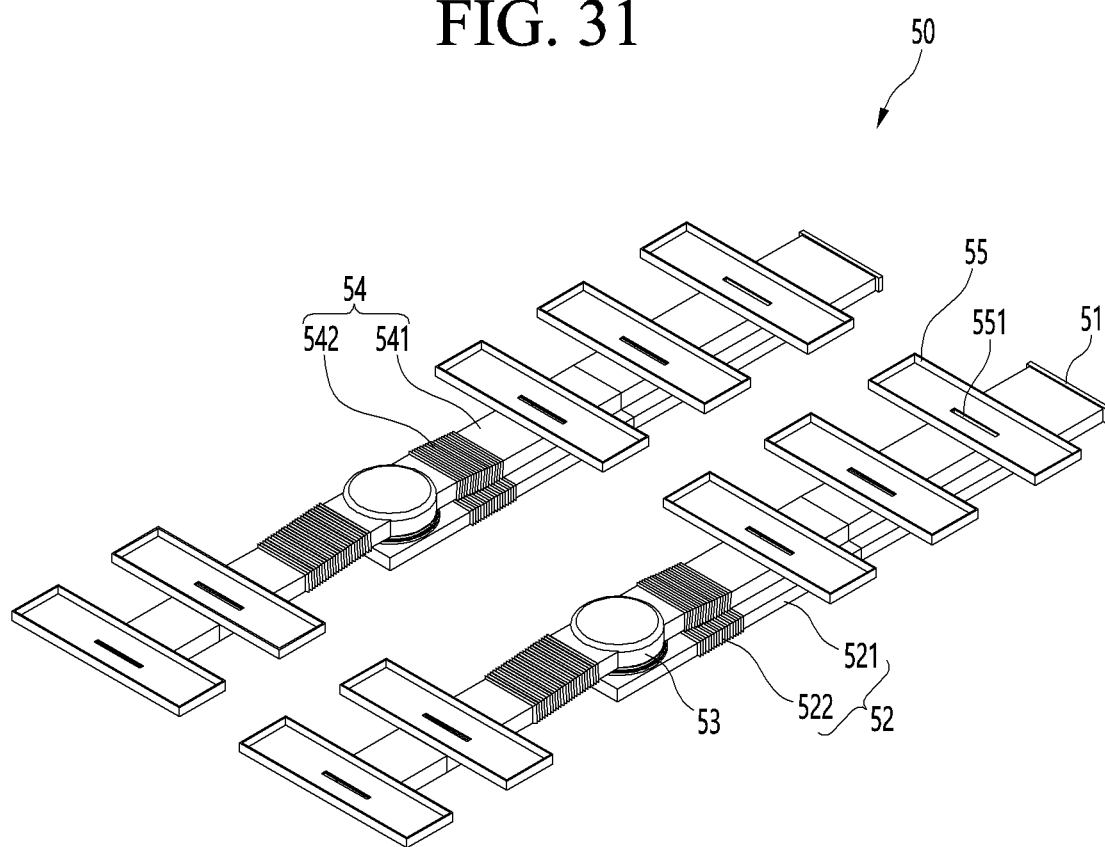
FIG. 31 is a perspective view of the drying module.

Referring to FIG. 31, the drying module or dryer 50 may include at least one fan or blower 53 to suction air, at least one suction duct 52 having a first end connected to a suction hole or side of the fan 53, and at least one supply duct 54 having a first end connected to a discharge hole or side of the fan 53. A second end opposite to the first end of the suction duct 52 may communicate with the inlet 131, and a filter 51 may be provided at the second end of the suction duct 52 to filter suctioned air. The supply duct 54 may be formed with discharge or outlet ducts 55, each discharge duct 55 having an outlet or discharge port 551. The discharge port 551 may be formed in a slit. The drying module 50 may have two sets of suction ducts 52, supply ducts 54, fans 53, etc. corresponding to left and right sides of the bed, but embodiments disclosed herein are not limited. A number of sets of suction ducts 52, supply ducts 54, fans 53, etc. may correspond to a number of inlets 131.

The second end of the suction duct 52 may be defined as an air intake or inlet of the drying module 50, and the discharge port 551 formed in the discharge duct 55 may be defined as an air discharge port or outlet of the dryer module 50. The suction and supply ducts 52 and 54 may be formed as hollow rectangular extensions having flat upper surfaces, but embodiments disclosed herein are not limited to a rectangular shape. Two supply ducts 54 coupled to opposite sides of the fan 53 may be at least partially provided on top of the upper surface of the suction duct 52, and the discharge ducts 55 may be provided on top of the upper surface of the supply duct 54. The filter 51 may be mounted at the second end of the suction duct 52, or alternatively may be mounted in the suction port 131 formed in the safe guard 13.

The drying module 50 may be fixed to the bedframe 30 such that, when the bedframe 30 is tilted, the drying module 50 may also be tilted. The suction duct 52 may include flexible ducts or sections 522 capable of bending and rigid ducts or section 521 that may not bend. Like the suction duct 52, the supply duct 54 may be formed of a combination of rigid ducts 541 and flexible ducts 542. The rigid ducts 521 and 541 and flexible ducts 522 and 542 may alternatively be referred to as hard and soft ducts. The flexible ducts 522 and 542 may be corrugated pipes or tubes and/or have an accordion spring structure. Alternatively, the flexible ducts 522 and 542 may be formed of an elastic or soft material, but embodiments disclosed herein are not limited.

The flexible ducts 522 and 542 may be provided under rotation axes of the bedframe 30 (i.e., under the partitions 40). For example, the flexible ducts 522 and 542 may be provided under where the upper body frame 31 and the hip frame 32 meet, where the hip frame 32 and the thigh frame 33 meet, and where the thigh frame 33 and the calf frame 34 meet.

The sets of suction and supply ducts 52 and 54 and fans 53 of the drying module 50 may be arranged in a width direction of the bed 10. As another alternative arrangement, although the fan 53 may have one inlet, the fan 53 may have multiple outlets and multiple sets of supply ducts 54 coupled to the multiple outlets of the fan 53. Such an alternative arrangement may have supply ducts 54 extending radially outward from the fan 53.

The fan 53 may be a centrifugal fan (e.g., a turbo fan) that suctions air in an axial direction and discharges air in a radial direction, but embodiments disclosed herein are not limited. The fan 53 may include a hub, blades, and a fan housing to accommodate the hub and blades. A single suction port or inlet may be formed on a bottom surface of the fan housing, and a plurality of discharge ports or outlets may be formed on a side surface of the fan housing. The fan 53 may be provided at a position far from the user's ear (e.g., at a foot of the bed 10) to reduce or prevent noise from disrupting the user.

As shown, a pair of discharge ports may be formed on opposite side surfaces of the fan housing of the fan 53. A pair of supply ducts 54 may extend a predetermined length in opposite directions from the fan housing of the fan 53 to be aligned in a single row. However, depending on the structure of the bedframe 30, the supply ducts 54 may be angled less than 180 degrees apart.

A plurality of discharge ducts 55 may extend across an upper surface of the supply duct 54, and the plurality of discharge ports 551 may be spaced apart from each other in the longitudinal direction of the supply duct 54. The discharge port 551 may penetrate the discharge duct 55 to communicate with outlets of the supply duct 54. The plurality of discharge ducts 55 and the supply ducts 54 may be injection molded into a single body. Alternatively, the plurality of discharge ducts 55 may be manufactured separately and later combined with the supply duct 54.

Each of the plurality of discharge ducts 55 may have a predetermined width and may extend for a predetermined length in a direction crossing an extending direction of the supply duct 54. An upper surface of the discharge duct 55 may be opened, and the discharge port 551 may penetrate a bottom surface. Alternatively, the discharge duct 55 may have a closed upper surface to be a hollow box or rectangle, and the discharge port 551 may penetrate both the upper and lower surfaces to communicate with the outlet of the supply duct 54. As another alternative, the discharge duct 55 may have an inlet formed in the bottom surface and communicating with the outlet of the supply duct 54, and the discharge port 551 may be formed in the upper surface. Embodiments disclosed herein are not limited.

The discharge port 551 may have a predetermined width, extends a predetermined length in the longitudinal direction of the discharge duct 55, and may be formed in a slit shape, but embodiments disclosed herein are not limited. When the discharge port 551 has a narrow slit shape, a speed of air discharged through the discharge port 551 may be increased to be effectively transferred to the topper 12. The width of the discharge duct 55 may correspond to a width of the partition 40, but dimensions of the discharge duct 55 are not limited.

When the drying module 50 includes one set of supply ducts 54, fan 53, and suction duct 52, the drying module 60 may be provided under a center of the bed 10, and the discharge duct 55 may have to a length corresponding to a width of the bed 10 or the topper 12. A length of the discharge port 551 may be elongated to extend width-wise under a majority of the bed 10.

The suction duct 52 may be approximately parallel to the supply duct 54, but embodiments disclosed herein are not limited. As another example, the suction duct 52 may be orthogonal to the supply duct 54 to extend in the width direction of the bed 10. As a length of the suction duct 52 decreases, a flow resistance may decrease. The suction port or inlet of the suction duct 52 may be provided at a side of the bed 10.

Figure 32:
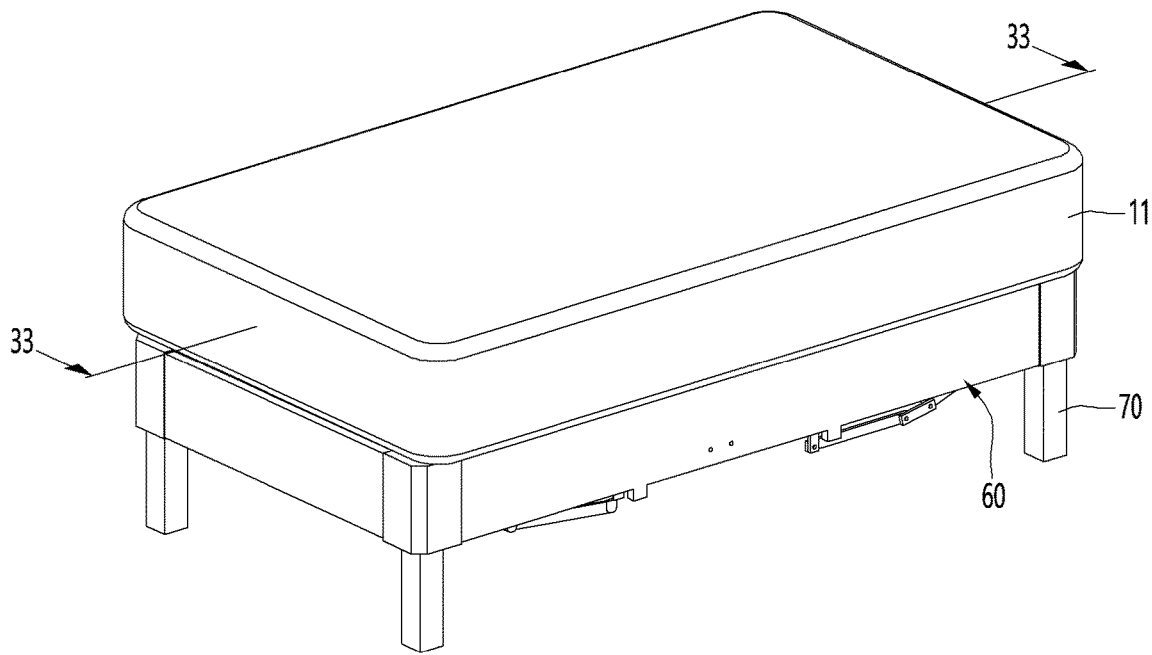
FIG. 32 is a perspective view of a bed according to another embodiment.
Figure 33:
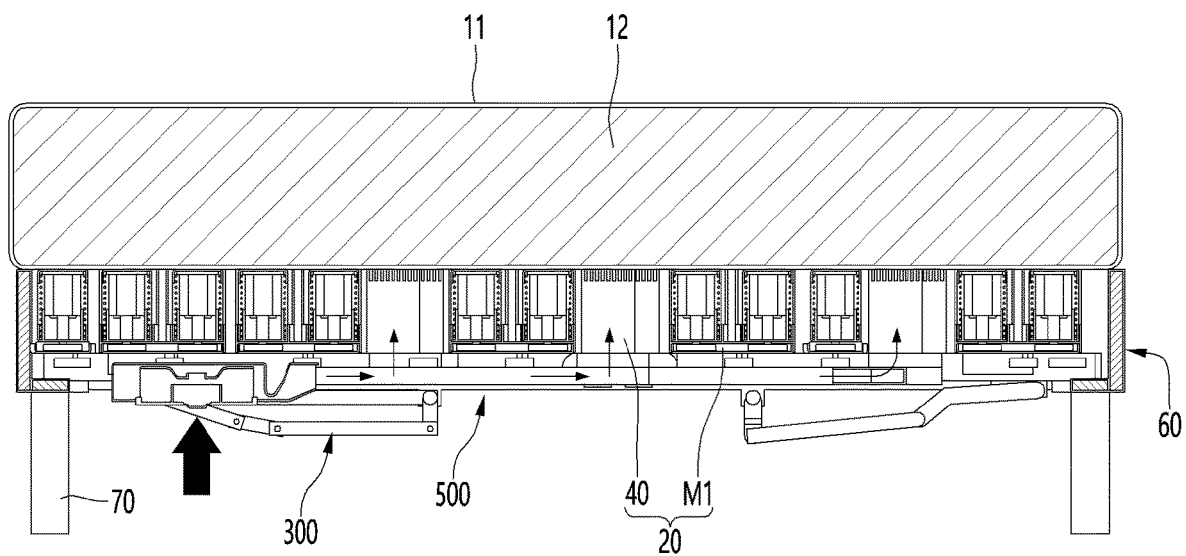
FIG. 33 is a longitudinal sectional view of the bed taken along 33-33 in FIG. 32.

Referring to FIGS. 32 and 33, a bed 10a according to a second embodiment may include a cushion module 20, a bedframe 300, and a topper 12 that is detachable from the cushion module 20. The topper 12 may be surrounded by a bed cover 11. Although a thickness of the topper 12 is shown to be greater than a thickness of the topper 12 shown in FIG. 3, embodiments disclosed herein are not limited to a thickness of the topper 12. For example, the topper 12 of the second embodiment may be just as thin or thick as the topper 12 of the first embodiment.

A drying module or dryer 500 may be provided below the bedframe 300, and the drying module 500 may be coupled to the bedframe 300 so that when the bedframe 300 is tilted, a portion of the drying module 500 may also be tilted. The drying module 500, like the drying module 50 described with reference to FIGS. 30-32, may suction ambient air and supply air to the topper 12 to dry the topper 12. The cushion module 20 may be defined as an assembly or array of firmness adjusters M1 and partitions 40, similar to the first embodiment.

The bed 10a may further include a guard frame 60 surrounding the cushion module 20 and the bedframe 300. The guard frame 60 may be similar to the safe guard 13 described with reference to FIGS. 1-32, but may also support a weight of the bedframe 300. The bedframe 300 may be coupled to an inside or inner surface of the guard frame 60 as one body, and at least a portion of the bedframe 300 may be bendable or tiltable while remaining secured to the guard frame 60. Here, the guard frame 60 may be more like a typical bedframe, while the bedframe 300 may primarily be a mattress mover, and could optionally be part of a mattress set.

The bed 10a may further include a plurality of legs 70 coupled to the corners of the guard frame 60. A bottom surface of the guard frame 60 may be spaced apart from the installation surface by a length of the leg 70, so that a link 3210, 3220 to be described later may be prevented from contacting the installation surface.

A height of the leg 70 may be designed so that components of the bedframe 300 do not contact the installation surface during an operation of the bedframe 300.

The leg 70 may be omitted if the bedframe 300 and the drying module 500 are designed do not touch the installation surface during an operation. For example, the guard frame 60 may contact the installation surface, and the bedframe 300 may be coupled to a middle or upper portion of the guide frame 60 at a position such that the bedframe 300 does not contact the installation surface during an operation.

Figure 34:
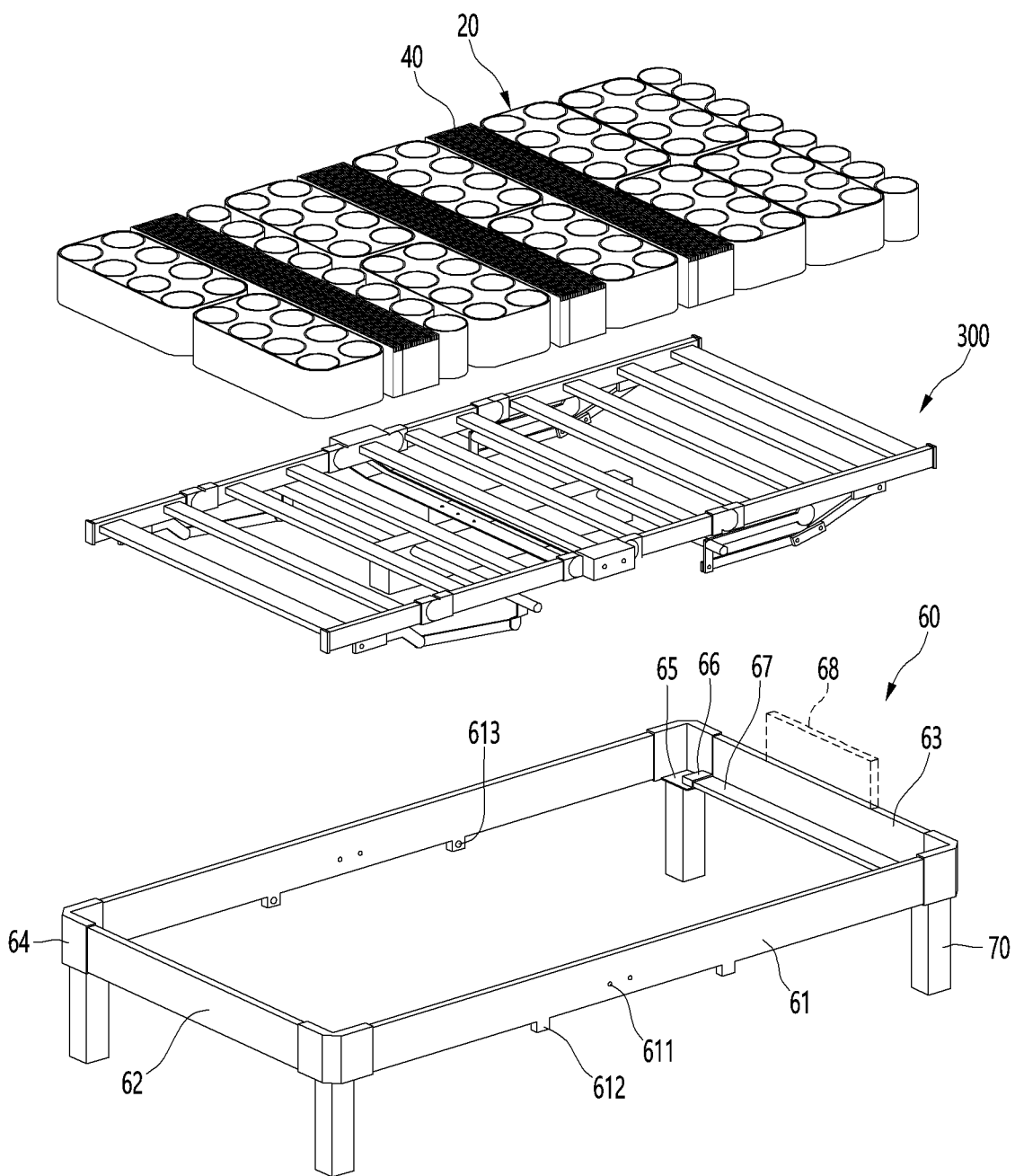
FIG. 34 is an exploded perspective view of the bed of FIG. 32.
Figure 35:
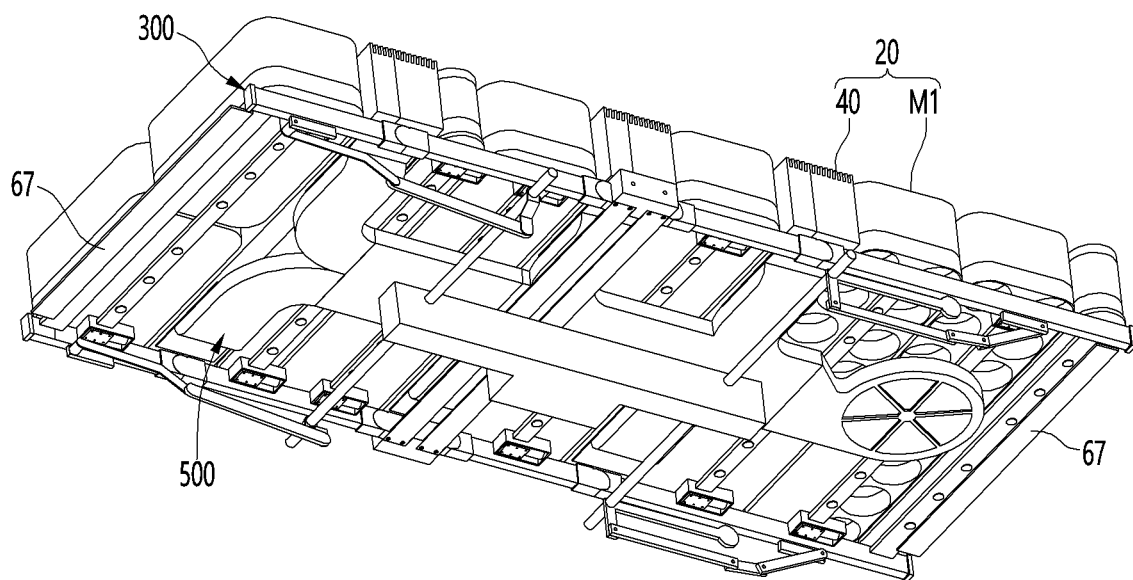
FIG. 35 is a bottom perspective view of cushion module or assembly and a bedframe combination according to an embodiment.

Referring to FIGS. 34-35, since the cushion module 20 may have a same or similar structure as the cushion module 20 described with reference to FIGS. 1-32, a repetitive description of the cushion module 20 will be omitted. The guard frame 60 may include a head frame or head 62, a toe frame or foot 63 opposite to the head frame 62, and a pair of side frames 61 extending between the head frame 62 and the toe frame 63. The head frame 62 may be provided at an edge of the cushion module 20 adjacent to the user's head when the user lies down. In addition, the toe frame 63 may be provided at an edge of the cushion module 20 adjacent to the user's foot.

The guard frame 60 may further include four connectors or brackets 64 provided at corners, respectively, where the head, toe, and side frames 62, 63, and 61 meet. The connector 64 may bend or curve by 90 degrees, and adjacent, perpendicular ends of the head, toe, and side frames 62, 63, and 61 may be coupled to ends of the same connector 64. The head, toe, and side frames 62, 63, and 61 may be connected via the four connectors 64 to form a single guard frame 60.

Four edge plates 65 may be provided at a lower edge of the guard frame 60 inside the four corners, respectively, to couple to the legs 70, and a fixing bracket 66 may be provided at each edge plate 65. Two support plates 67 may be provided at an inner side of a lower end of the head frame 62 and the toe frame 63, respectively, and left and right ends of the support plates 67 may be supported by the fixing brackets 66. The fixing bracket 66 may have an n-shape so that both ends of the support plate 67 are fitted to or within the fixing bracket 66.

Bottom surfaces of the front and rear ends (i.e., the head and foot) of the bedframe 300 may be placed on the support plate 67 to prevent sagging or drooping. Centers of left and right sides of the bedframe 300 may be fixed to the side frame 61 by a fixing block 3310 to be described later with reference to FIGS. 36-37. A fastening hole 611 may be formed in a central portion of the side frame 61 so that a fastening member (e.g. screw or bolt) described later may couple the side frame 61 and the fixing block 3310. A link drive shaft connection end 612 may extend or protrude downward at a lower end of the side frame 61. A link drive shaft 3150 to be described later may be rotatably connected to the link drive shaft connection end 612.

A topper guard or frame 68 may extend or protrude upward at an upper end of the toe frame 63 to prevent the topper 12 from sliding down while the bedframe 300 is tilted. The topper guard 68 may be formed integrally with the toe frame 63, or alternatively may be formed separately and later combined with the toe frame 63.

The drying module 500 may be provided under the cushion module 20 and fixed to the bedframe 300. A part of the drying module 500 may be tilted together with the bedframe 300.

Figure 36:
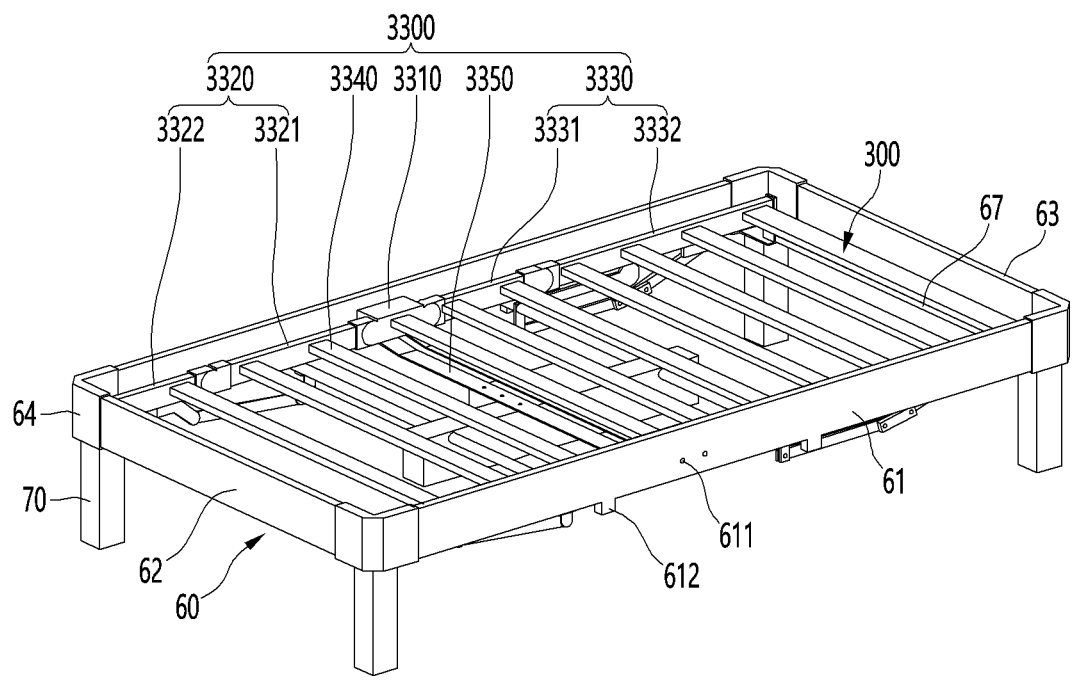
FIG. 36 is a perspective view from above of a combination of a bedframe and a guard frame according to an embodiment.
Figure 37:
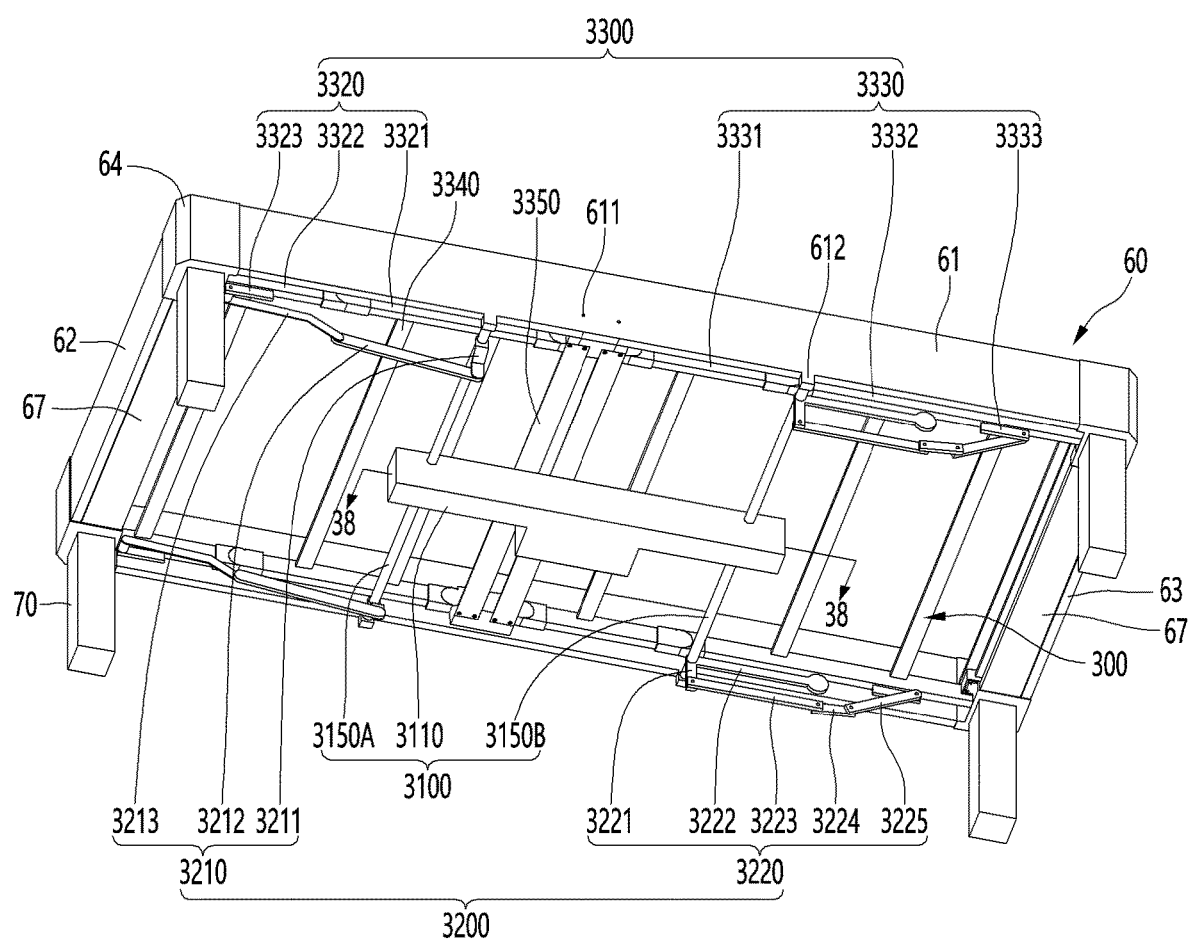
FIG. 37 is a perspective view from below of a combination of a bedframe and a guard frame according to a second embodiment.

Referring to FIGS. 36 and 37, the bedframe 300 may include a motion generator 3100, a motion link 3200, and a seating frame 3300. The seating frame 3300 may provide a surface on which the cushion module 20 is placed, and the seating frame 3300 may be bent and tilted by a driving force supplied from the motion generator 3100. The seating frame 3300 may include a pair of fixing blocks 3310, an upper body frame 3320, a lower body frame 3330, a cushion seating plate or bar 3340, and a fixing bar 3350.

The pair of fixing blocks 3310 may be fixed to inner surfaces of the pair of side frames 61 of the guard frame 60 to face each other. A fastening member (e.g., a screw or bolt) may pass through the fastening hole 611 formed in the side frame 61 and be inserted into the fixing block 3310. The pair of fixing blocks 3310 may be located at a central point of the side plate 61, but embodiments disclosed herein are not limited.

A rear end of the upper body frame 3320 and a front end of the lower body frame 3330 may be rotatably coupled to the fixing block 3310. The upper body frame 3320 may include a pair of rear frames 3321 having rear ends rotatably coupled to the pair of fixing blocks 3310, respectively, and a pair of front frames 3322 rotatably coupled to the front ends of the rear frames 3321, respectively. Each of the pair of rear frames 3321 and the pair of front frames 3322 may be parallel to each other.

The lower body frame 3330, like the upper body frame 3320, may have a pair of front frames 3331 rotatably coupled to the pair of fixing blocks 3310 and a pair of rear frames 3332 rotatably coupled to rear ends of the front frames 3331, respectively. The cushion seating plate 3340 may connect frames among the front and rear frames 3322, 3331, 3321, and 3332 that are provided parallel to each other.

The seating frame 3300 may be defined as a structure including a plurality of parallel cushion seating plates 3340 connected to each other to resemble a slatted bed frame. With respect to the upper body frame 3320, the front frame 3322 may be or include a pair of parallel straight bars, and at least one seating plate 3340 may connect the pair of parallel straight bars of the front frame 3322. The rear frame 3321 may be or include a pair of parallel straight bars, and at least one seating plate 3340 may connect the pair of parallel straight bars of the rear frame 3321. Similarly, with respect to the lower body frame 3330, the front frame 3331 may be or include a pair of parallel straight bars, and at least one cushion seating plate 3340 may connect the pair of parallel straight bars of the front frame 3331. The rear frame 3332 may be or include a pair of parallel straight bars, and at least one cushion seating plate 3340 may connect the pair of parallel straight bars of the rear frame 3332. A coupling between the cushion seating plates 3240 and the bars may be optionally rotatable at tilting axes. Furthermore, at lease one cushion seating plate 3340 may be coupled (e.g., rotatably coupled) to the fixing block 3310.

Similar to how the seating frame 39 described with reference to FIGS. 1-32 is divided into sections that move or pivot relative to each other (upper body frame 31, the hip frame 32, the thigh frame 33, and the calf frame 34), the seating frame 3300 may be divided into sections that move or pivot relative to each other, the sections being defined by the pair of front frames 3322 of the upper body frame 3320 and the cushion seating plates 3340 therebetween, the pair of rear frames 3321 of the upper body frame 3320 and the cushion seating plates 3340 therebetween, the pair of front frames 3331 of the lower body frame 3330 and the cushion seating plates 3340 therebetween, and the pair of rear frames 3332 of the lower body frame 3330 and the cushion seating plates 3340 therebetween.

Left and right ends of the fixing bar 3350 may connect bottom surfaces of the pair of fixing blocks 3310, respectively, so as to reduce or prevent sagging of the bedframe 300. In addition, a transmission or transmitter 3110 of the motion generator 3100 may be coupled to the fixing bar 3350. The transmission 3110 will be described in more detail later.

An upper link connection end or front bracket 3323 may be provided on a bottom surface of the pair of front frames 3322 of the upper body frame 3320. A lower link connection end or rear bracket 3333 may be provided on a bottom surface of the pair of rear frames 3322 of the lower body frame 3330, respectively.

The motion generator 3100 may tilt or pivot the various sections of the seating frame 3300 via the motion link 3200. The motion generator 3100 may include one transmission 3110 and a link drive shaft 3150 penetrating the transmission. Both ends of the link drive shaft 3150 may connect to the link drive shaft connection end 612, respectively.

The link drive shaft 3150 may be a pair of shafts coupled to the transmission 3110. The pair of shafts of the link drive shaft 3150 may include a front shaft 3150A passing through a front end of the transmission 3110 and a rear shaft 3150B passing through a rear end of the transmission 3110.

A mounting groove or recess may be formed on an inner surface of the link driving shaft connecting end 612, and an end of the link driving shaft 3150 may be fitted into the mounting groove. Alternatively, the mounting groove may be a hole. Further, a plurality of ball bearings may be arranged on an inner circumferential surface of the mounting groove so that frictional force may be reduced when the link drive shaft 3150 rotates. Since both ends of the link drive shafts 3150 may be connected to the link drive shaft connection end 612, a load of the motion generator 3100 and the motion link 3200 may be supported by the guard frame 60.

The motion link 3200 may include a pair of front links 3210 connected to both ends of the front shaft of 3150A, and a pair of rear links 3220 connected to both ends of the rear shaft 3150B. The front link 3210 may have a two-fold link structure via a moveable link 3213 and a fixing link 3212, while the rear link 3220 may have a multi-fold link structure via an arm link 3222, a fixing link 3223, a moveable link 3225, and a connection link 3224.

The front link 3210 may include a rear bracket 3211 extending downward from the font shaft 3150A. The fixed link 3212 may extend from an end of the bracket 3211, and the movable link 3213 may be rotatably connected to a rear end of the fixing link 3212. A front end of the movable link 3213 may be connected (either fixedly or rotatably) to the front bracket 3323. The front bracket 3323 may be formed to be parallel to the front frame 3322 of the upper body frame 3320, while the rear bracket 3211 may extend downward.

Figure 41:
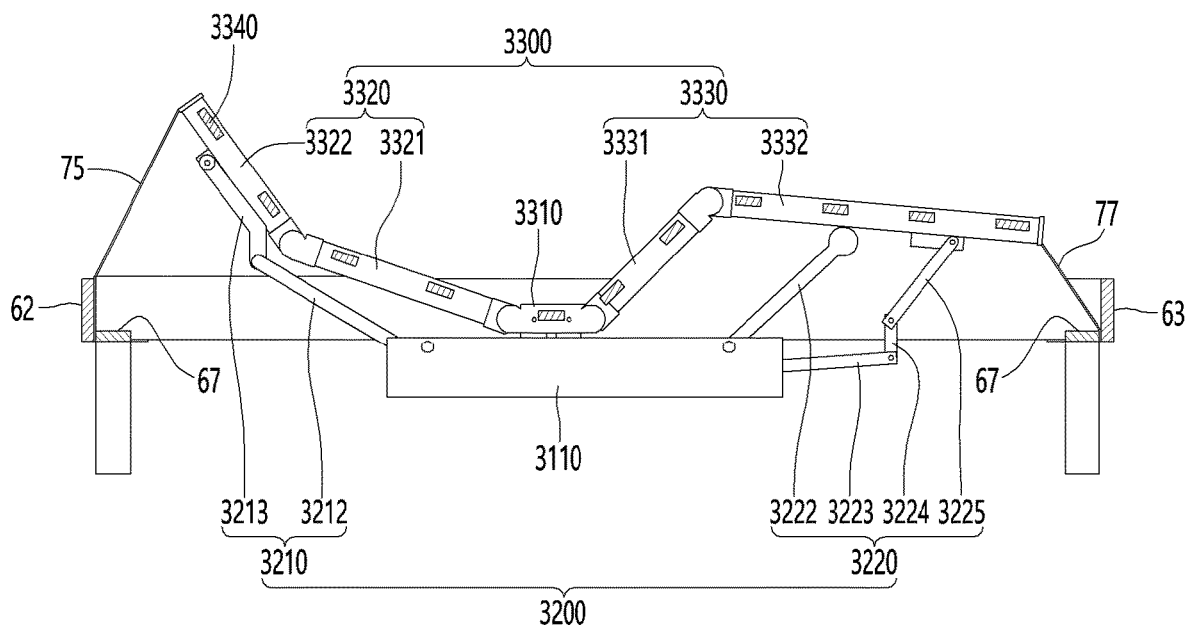
FIG. 41 is a longitudinal sectional view of the motion controller cut along 41-41 in FIG. 40.

A rear end of the fixing link 3212 may be fixed to a bottom end the bracket 3211, and the front shaft 3150A, the bracket 3211, and the fixing link 3212 may rotate as one body. When the front shaft 3150A rotates, the bracket 3211 and fixing link 3212 may rotate with the front shaft 3150A, while the moveable link 3213 may rotate or pivot with respect to the fixing link 3212. FIG. 41 shows a state in which the front shaft 3150A has been rotated to tilt the bracket 3211 and fixing link 3212.

The rear link 3220 may include a front bracket 3221 extending downward from the rear shaft 3150B. The arm link 3222 may extend from the rear shaft 3150 in a direction perpendicular to a downward extension direction of the front bracket 3221. The fixed link 3223 may have a front end rotatably connected to a rear end of the front bracket 3221. The connection link 3224 may have a front end rotatably connected to a rear end of the fixing link 3223. The rear end of the connection link 3224 may be rotatably connected to a front end of the movable link 3225. The front bracket 3221 and the arm link 3222 may be formed of a single member that is bent in an L-shape, but embodiments disclosed herein are not limited. The rear shaft 3150B may pass through the bracket 3221 to be fixed.

The arm link 3222 may include an arm link body horizontally extending from the rear shaft 31506, and a circular slider may be formed at a rear end of the arm link body. A diameter of the slider may be larger than a width of the arm link body so that an upper surface of the slider of the arm link 3222 may contact the lower surface of the rear frame 3332 of the lower body frame 3330.

An upper surface of the slider may slide along a bottom surface of the rear frame 3332 while maintaining contact so that when the rear shaft 3150B rotates, the rear frame 3332 of the lower body frame 3330 may move or pivot relative to the front frame 3331 of the lower body frame 3330. The rear end of the movable link 3225 may be rotatably connected to the rear bracket 3333. The rear bracket 3333 of the rear link 3220 may have a similar structure as the front bracket 3323 of the front link 3210. The rear shaft 3150B, the front bracket 3221, and the arm link 3222 may rotate together as one body.

As previously described, the front link 3210 may have a two-fold link structure via the moveable link 3213 and the fixing link 3212, and the rear link 3220 may have a multi-fold link structure via the arm link 3222, fixing link 3223, moveable link 3225, and connection link 3224. Although the rear link 3220 is shown to be a four-fold link, embodiments disclosed herein are not limited in a number of links comprising the front and rear links 3210 and 3220.

Figure 38:
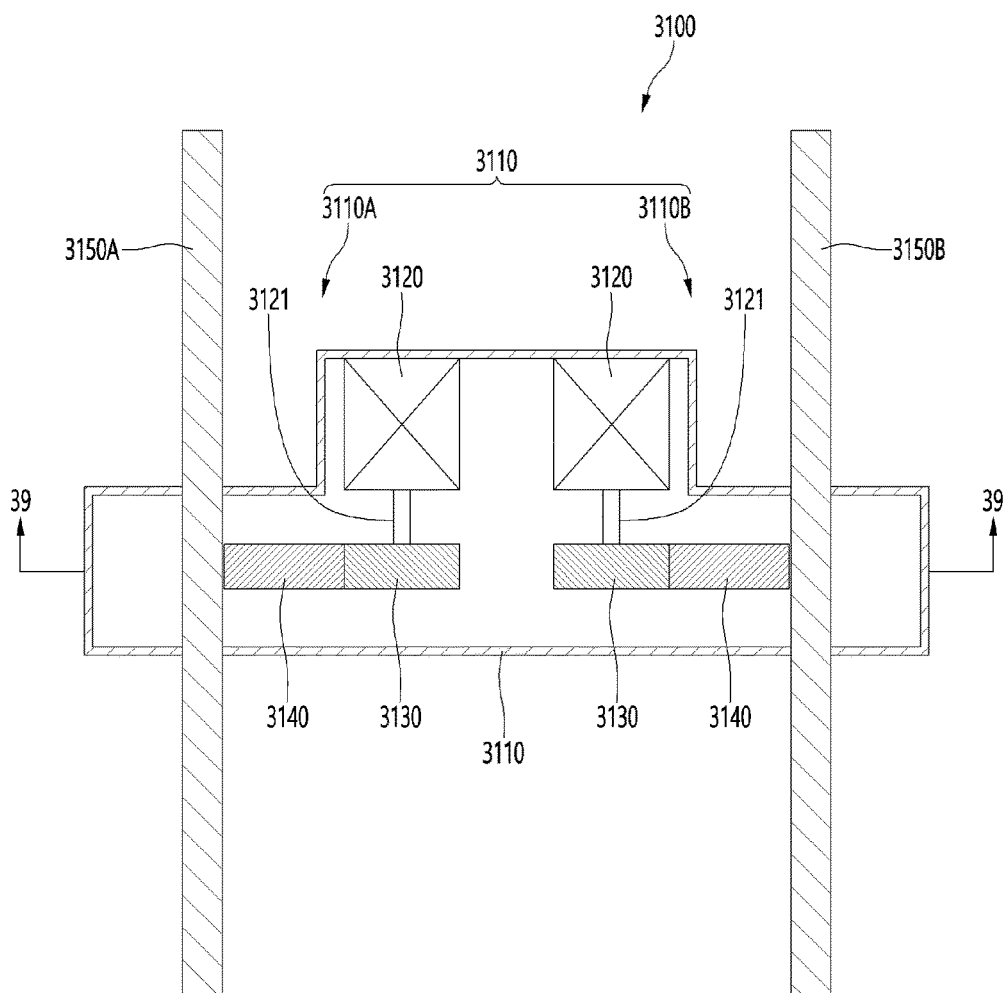
FIG. 38 is a cross-sectional view of a motion generator of the bedframe cut along 38-38 of FIG. 37.
Figure 39:
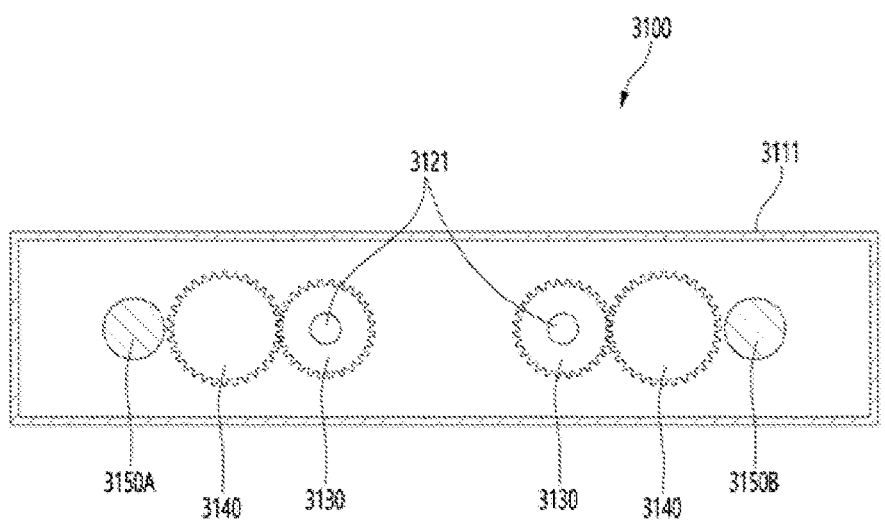
FIG. 39 is a longitudinal sectional view of a motion generator cut along 39-39 of FIG. 38.

Referring to FIGS. 38 and 39, the motion generator 3100 may generate a driving force via the transmission 3110 to rotate the front and rear shafts 3150A and 3150B of the link drive shaft 3150, which may be connected to the transmission 3110. The transmission 3110 may include a gear box or container 3111 and front and rear transmission assemblies 3110A and 3110B provided inside of the gear box 31110 and corresponding to the front and rear shafts 3150A and 3150B, respectively. Each transmission assembly 3110A, 3110B may include a motor 3120, a tilting gear 3130 connected to a rotation shaft 3121 of the motor 3120, and a reduction gear 3140 meshed with or configured to engage with the tilting gear 3130.

Each of the front and rear shafts 3150A and 3150B may penetrate the gear box 3110 and rotate while being meshed or engaged with the reduction gear 3140. The two transmission assemblies 3110A and 3110B may independently drive a rotation of the front and rear shafts 3150A and 3150B, respectively, so that the upper body frame 3320 and the lower body frame 3330 may be adjusted independently of each other.

Various types of structures may be implemented as the transmission 3110, and embodiments disclosed herein are not limited to the front and rear transmission assemblies 3110A and 3110B described. Embodiments disclose herein may include all types of transmissions 3110 in which power is generated from a gearbox 3110 and transmitted to a link drive shaft 3150.

Figure 40:
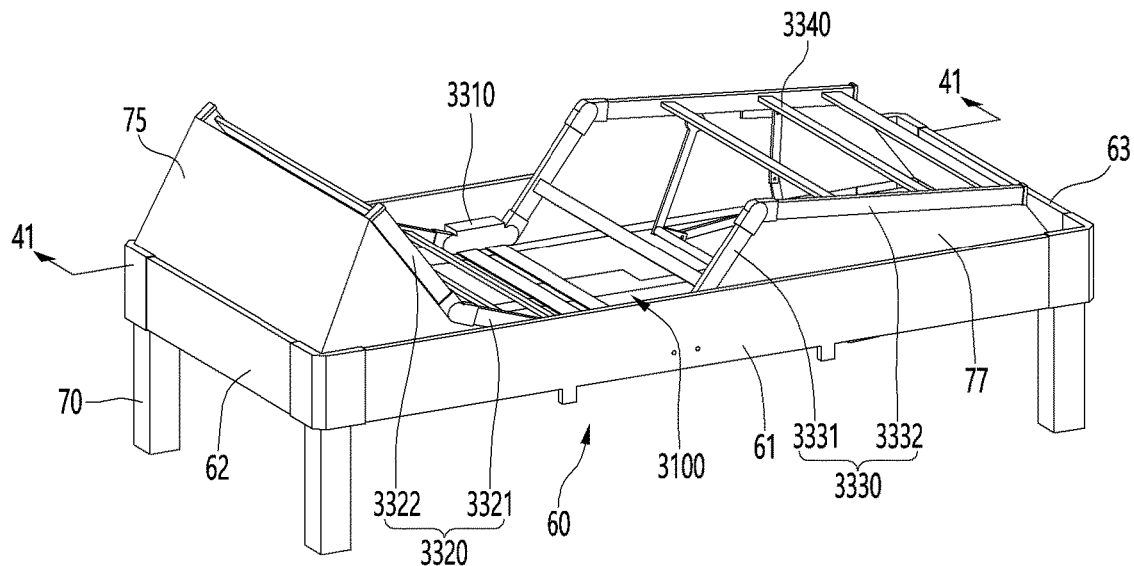
FIG. 40 is a perspective view showing the operation of the bedframe according to an embodiment.

Referring to FIGS. 40 and 41, when power is supplied to the motion generator 3100 and the motor 3120 is operated, the link driving shaft 3150 may rotate. When the front shaft 3150A rotates, the front link 3210 may rotate to tilt the upper body frame 3320 by a predetermined angle, and when the rear shaft 3150B rotates, the rear link 3220 may rotate to tilt the lower body frame 3330 by a predetermined angle.

The fixed link 3212 of the front link 3210 may be fixed to the rear bracket 3211, while an end of the movable link 3213 may maintain a connection to the front frame 3322 via the front bracket 3323. When the motor 3120 in the front transmission assembly 3110A is operated, the front shaft 3110A rotates, and the front link 3210 rotates to tilt both the front and rear frames 3322 and 3321 of the upper body frame 3320 upward by a predetermined angle.

When the motor 3120 in the rear transmission assembly 3110B is operated, the rear shaft 3110B rotates, and the front bracket 3221 and the arm link 3222 may rotate as one body. The rear frame 3332 of the lower body frame 3320 may be lifted as the arm link 3222 rotates upward. As the arm link 3222 and the front bracket 3221 rotate, the fixed link 3223 may be pushed forward, and a rear end of the rear frame 3332 may be supported via the rear link 3333 and the moveable link 3225. In addition, the rear end of the front frame 3331 may be rotated as the lower frame 3332 rises, resulting in a state as shown in FIG. 41.

As the arm link 3222 rotates by a rotation of the rear shaft 3150b, the arm link 3222 may slide along the bottom surface of the lower frame 3322. Without the moveable link 3225 and rear bracket 3333, the rear end of the rear frame 3332 may sag downward.

As the upper body frame 3320 and/or the lower body frame 3330 are tilted, a space or gap may form between the upper body frame 3320 and the guard frame 60 and/or between the lower body frame 3330 and the guard frame 60. Foreign substances may be introduced into or under the bed 10a through the gap, and body parts may be caught and injured in the gap.

In order to prevent such problems, at least one blocking film or layer 75, 77 may be provided. The blocking film 75, 77 may include an upper or front blocking film 75 connecting the upper body frame 3320 and the guard frame 60, and a lower or rear blocking film 77 connecting the lower body frame 3330 and the guard frame 60 can do. The front and rear blocking films 75 and 77 may alternatively be referred to as cover sheets or blocking sheets.

The front and rear blocking films 75 and 77 may be formed of a soft or elastic cloth, sheet, or band, a folded or wrinkled cloth, a material having an accordion bellow or spring shape, etc. Embodiments disclosed herein are not limited to a material of the front and rear blocking films 75 and 77.

Figure 42:
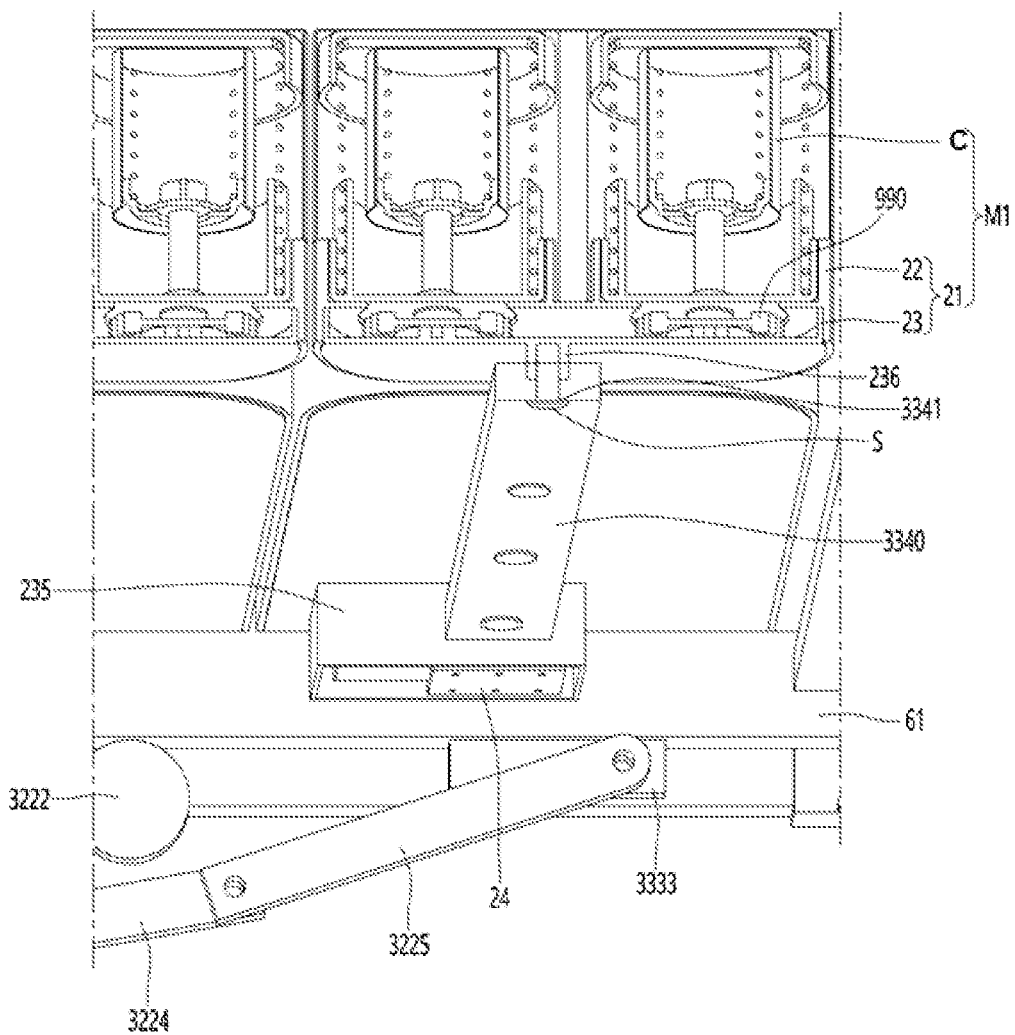
FIG. 42 is a partially cut-away perspective view showing an enlarged view of the firmness adjuster being coupled to the bedframe according to an embodiment.

Referring to FIG. 42, the cushion module 20 may be an assembly of a plurality of firmness adjusters M1, and each of the firmness adjusters M1 may include a cushion case 21 and a plurality of cushions C provided in the cushion case 21. The cushion case 21 may include an upper or outer case 22 and a bottom or inner case 23. When the bottom case 23 is coupled to the cushion seating plate 3340, the cushion module 20 may constitute one section of the bedframe 300. In addition, the topper 12 may be detachable from the cushion module 20.

A plurality of fastening bosses 236 may be formed on the bottom surface of the bottom case 23 to be spaced apart by predetermined intervals. In addition, a plurality of fastening holes 3241 may be formed in the cushion seating plate 3340.

A fastening member S (e.g., screw or bolt) may pass through the fastening hole 3241 and be inserted into the fastening boss 236. The cushion case 21 may be fixed to the cushion seating plate 3340 by the fastening member S. As an alternative, the fastening boss 236 may be omitted, and an inner surface of the fastening hole 3341 may have threads. Embodiments disclosed herein are not limited.

Figure 43:
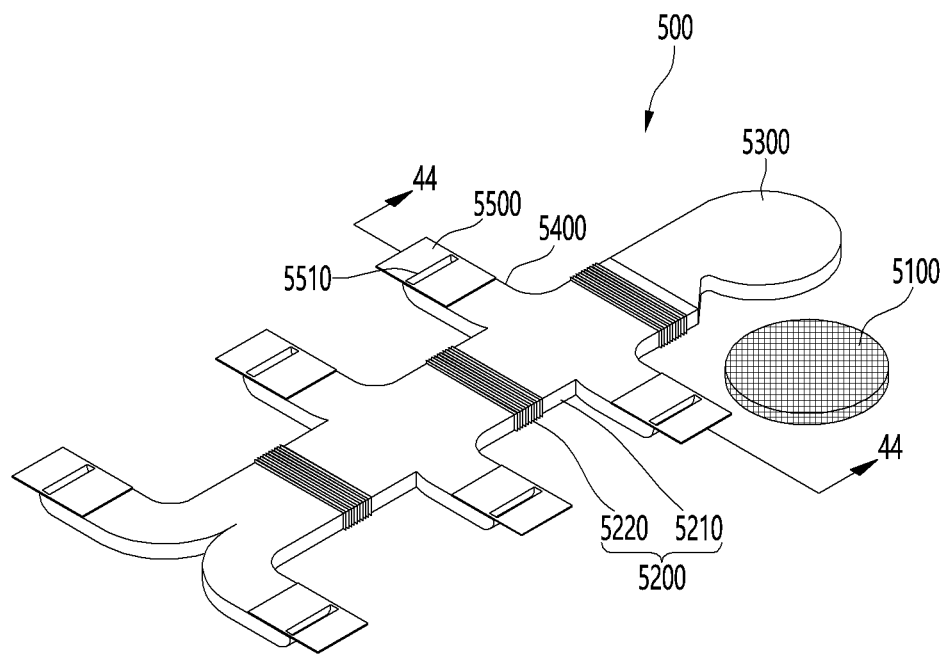
FIG. 43 is a perspective view of a drying module of the bed of FIG. 2.
Figure 44:
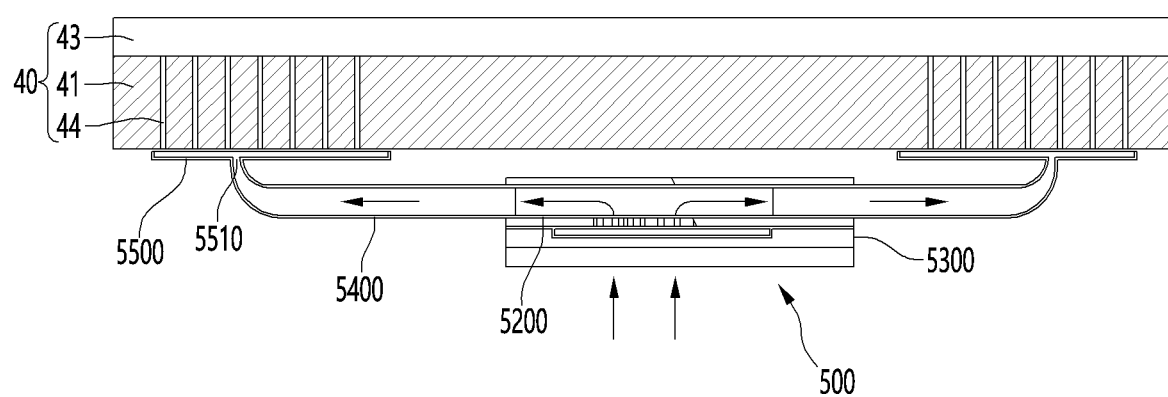
FIG. 44 is a longitudinal cross-sectional view of a bed cut along 44-44 of FIG. 43 with a topper placed on an upper side of the drying module.
Figure 45:
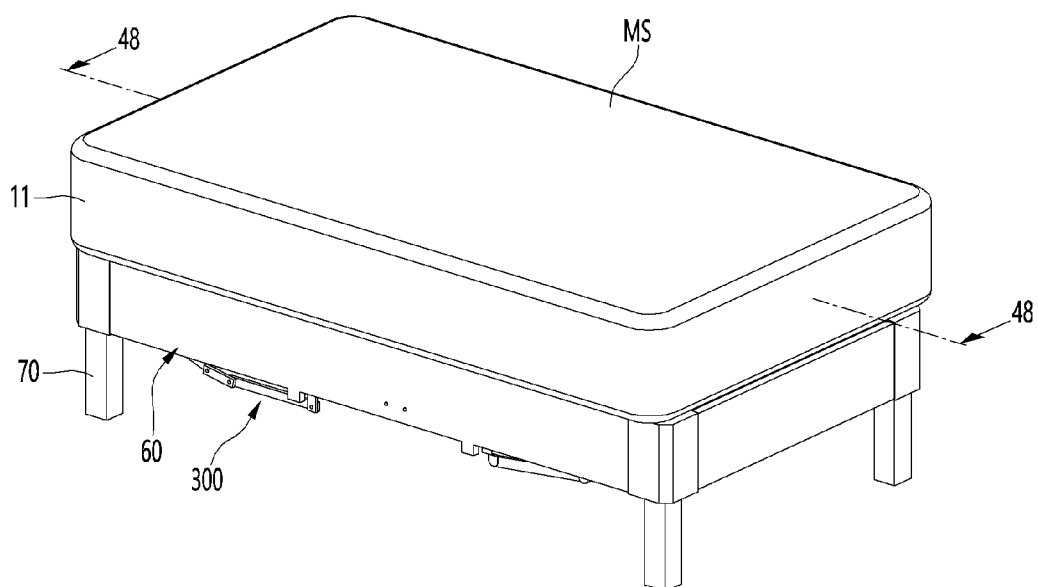
FIG. 45 is a perspective view from above of a bed according to another embodiment.
Figure 46:
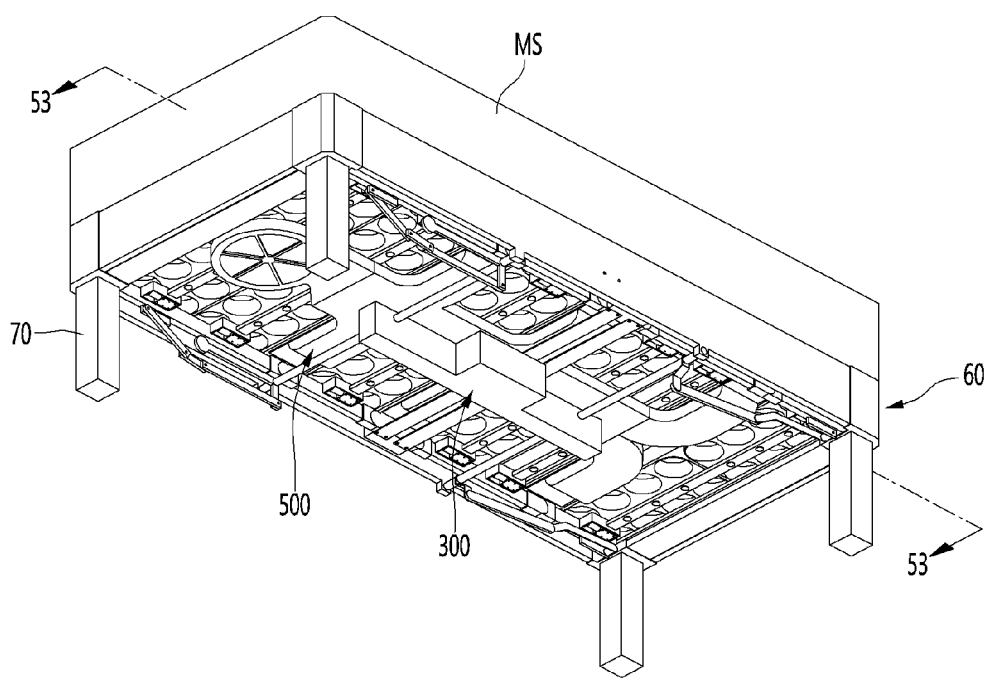
FIG. 46 is a perspective view as viewed from below of the bed of FIG. 45.
Figure 47:
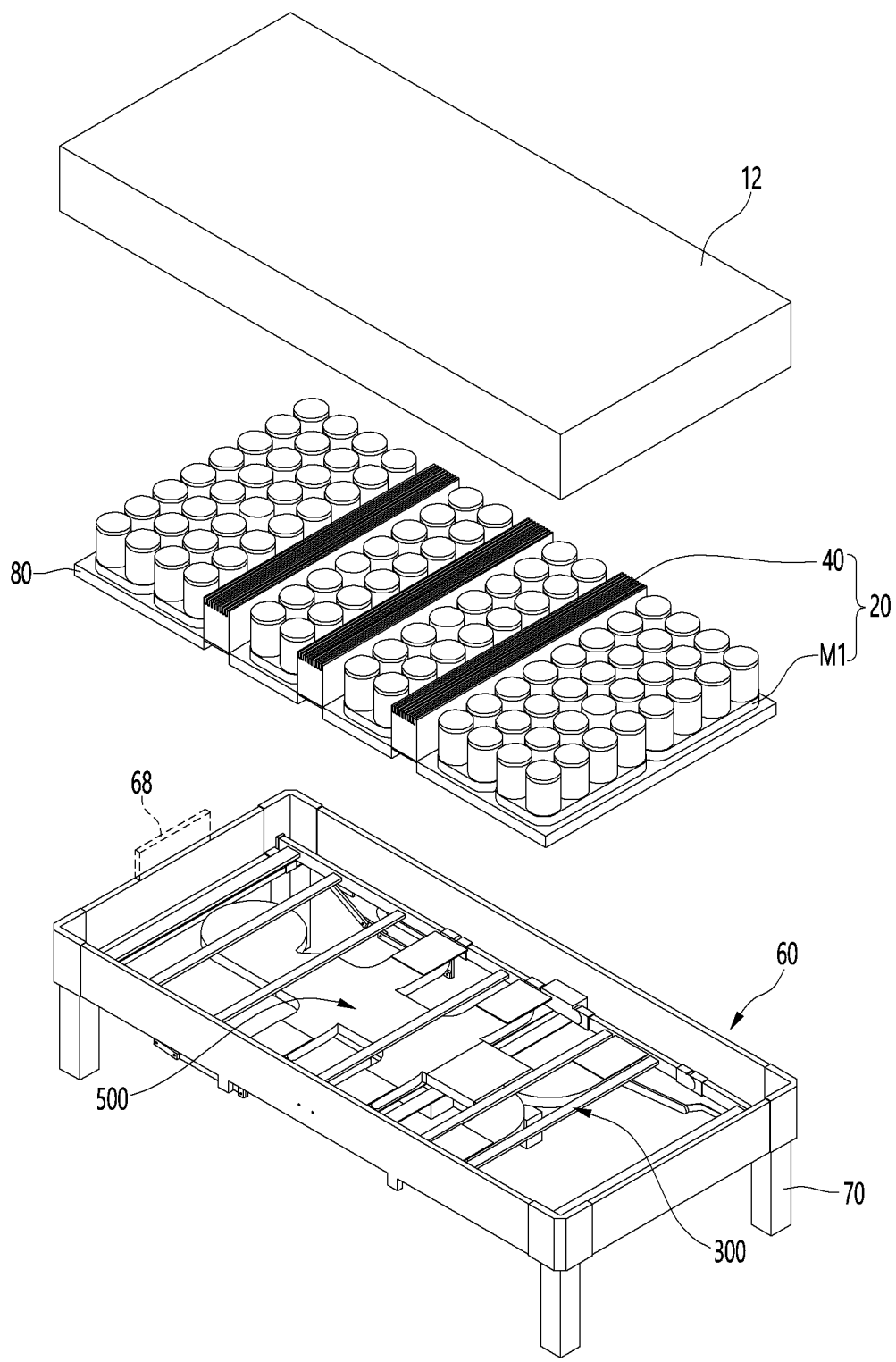
FIG. 47 is an exploded perspective view of the bed of FIG. 45.
Figure 48:
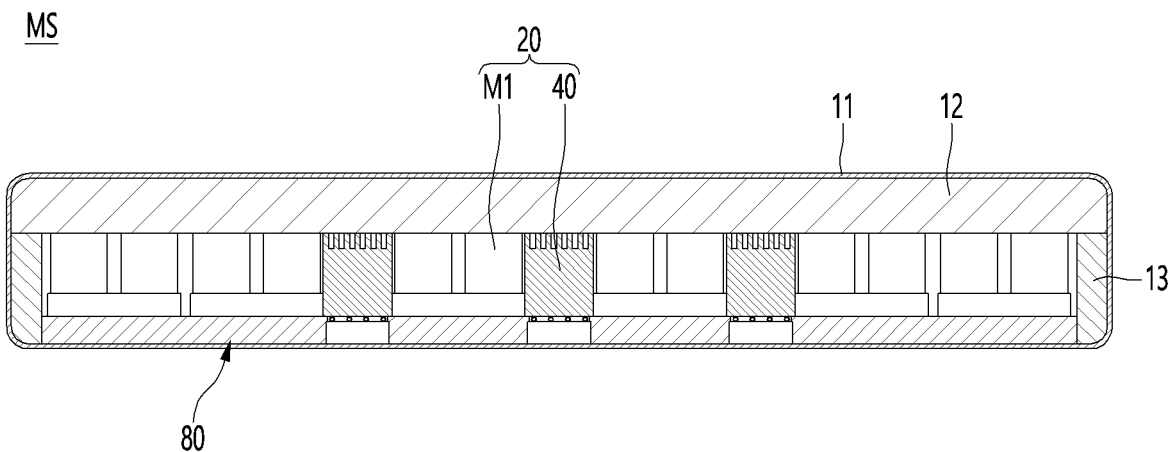
FIG. 48 is a longitudinal sectional view of a mattress set cut along 48-48 of FIG. 45.

Referring to FIGS. 43 and 44, the drying module 500 may include a fan 5300, a filter 5100 provided at an inlet of the fan 5300, a supply duct 5200 connected to an outlet of the fan 5300, a branch duct 5400 extending from a side of the supply duct 5200, and a discharge duct 5500 connected to an outlet of the branch duct 5400.

Unlike the suction duct 52 described with reference to FIGS. 1-32, a suction duct may be omitted in the bed 10a, as the drying module 500 may be separated from the installation surface by the legs 70 so that flow resistance may be low when suctioning air. However, when the leg 70 is excluded, a suction duct may be connected to the inlet of the fan 5300. In this alternative case, the filter 5100 may be mounted at an inlet end of the suction duct.

The fan 5300 may be installed as far as possible from the user's ear to reduce inconvenience and noise reaching the user. For example, the fan 5300 may be provided at a point adjacent to the toe frame 63 of the guard frame 60. The supply duct 5200 may extend in a longitudinal direction of the bed 10a from the outlet of the fan 5300 and along a center of the bottom of the bed 10a.

Similar to the supply duct 54 described with reference to FIGS. 1-32, the supply duct 5200 may include a hard duct 5210 and a soft or flexible duct 5220. The supply duct 5200 may be fixed to the bedframe 300 so as to move with a motion of the bedframe 300.

The branch duct 5400 may extend in a width direction of the bed 10a from left and right sides of the supply duct 5200. The branch duct 5400 may have an end that is convexly bent or curved, and an upper surface of the curved end may be opened to form the outlet of the branch duct 5400.

The outlet of the branch duct 5400 may be connected to a center of a bottom of the discharge duct 5500. A discharge port or slit 5510 may be formed in a slit shape at a center of the bottom of the discharge duct 5500. Like the discharge duct 55 described with reference to FIGS. 1-32, an upper surface of the discharge duct 5500 may be opened so air discharged from the discharge port 5510 may collide with a bottom surface of the partition 40.

The discharge duct 5500 may have a predetermined width, which may correspond to a width of an upper side of the branch duct 5400 and/or a width of the partition 40, but embodiments disclosed herein are not limited. The discharge duct 5500 may extend in a direction parallel to the branch duct 5400.

As shown in 44, the partition 40 may be formed of a body 41, fins 43, and a plurality of ventilation holes 44 formed in the body 41. The plurality of ventilation holes 44 may be formed to be directly above the discharge ducts 5500 so that air discharged from the discharge duct 5500 may pass through the ventilation hole 44 to the topper 12.

Due to structural characteristics of the cushion module 20, when the discharge duct 5500 is placed under the cushion case 21, the air discharged from the discharge duct 5500 may spread to the side and the topper 12, and an amount of air reaching the topper 12 may be significantly reduced. By aligning the discharge duct 5500 with the plurality of ventilation holes 44, most of the air discharged from the discharge duct 550 may pass through the partition 40 to a bottom of the topper 12. Air that does not pass through the partition 40 may spread to the side of the topper 12 or be guided to the topper 12 through gaps formed between the firmness adjusters M1. As an alternative, a button of the cushion case 21 may be formed with hole to allow air to pass through between the cushion.

Referring to FIGS. 45 to 48, a bed 10b according to a third embodiment may have a cushion module 20 separable from the bedframe 300. A topper 12 and the cushion module 20 may be held together by a bedsheet 11 (e.g., a fitted or elastic sheet or a mattress protector) to form a mattress set MS.

The bed 10b may include a guard frame 60 and a bedframe 300 coupled to the guard frame 60. The mattress set MS may be detachably seated in the bedframe 300. According to design conditions, the bed 10b may optionally include a plurality of legs 70 extending from the lower four corners of the guard frame 60.

The guard frame 60, the bedframe 300, and the drying module 500 coupled to the bedframe 300 may be similar to the bed 10a described with reference to FIGS. 33-44. Accordingly, redundant descriptions of these configurations are omitted, and the contents described in the second embodiment are applied mutatis mutandis.

The mattress set MS may include a mattress (i.e., the cushion module 20 and the topper 12) and a seat plate 80 on which the mattress is placed. The mattress set MS may be interpreted as further including the bed cover 11 surrounding the mattress and the module seating plate 80.

According to design conditions, the mattress set MS may further include a safe guard 13 surrounding side surfaces of the cushion module 20 and the seat plate 80. Since the safe guard 13 has already been described when describing the bed 10 according to the first embodiment with reference to FIGS. 1-32, redundant descriptions will be omitted. The cushion module 20 may include a plurality of firmness adjusters M1 and a plurality of partitions 40 provided between the plurality of firmness adjusters M1 as described above.

Figure 49:
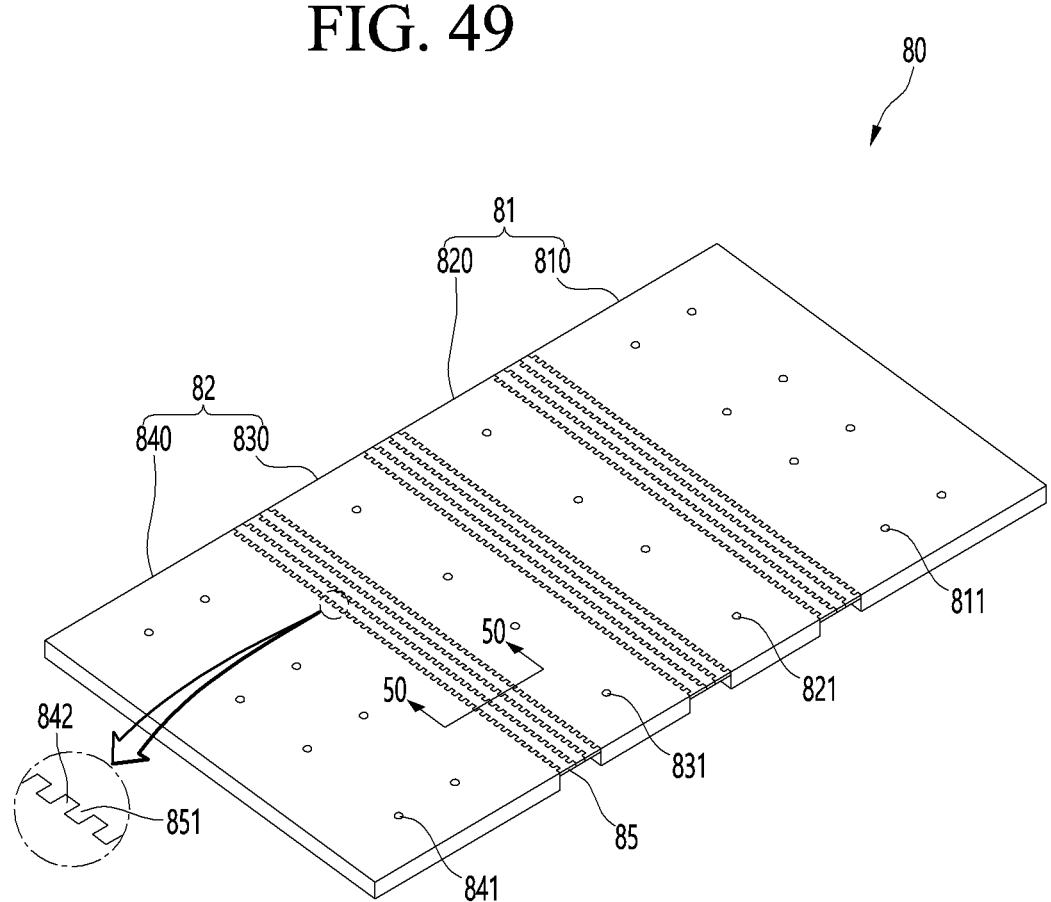
FIG. 49 is a perspective view of a seating plate constituting a mattress set for the bed of FIG. 45.
Figure 50:
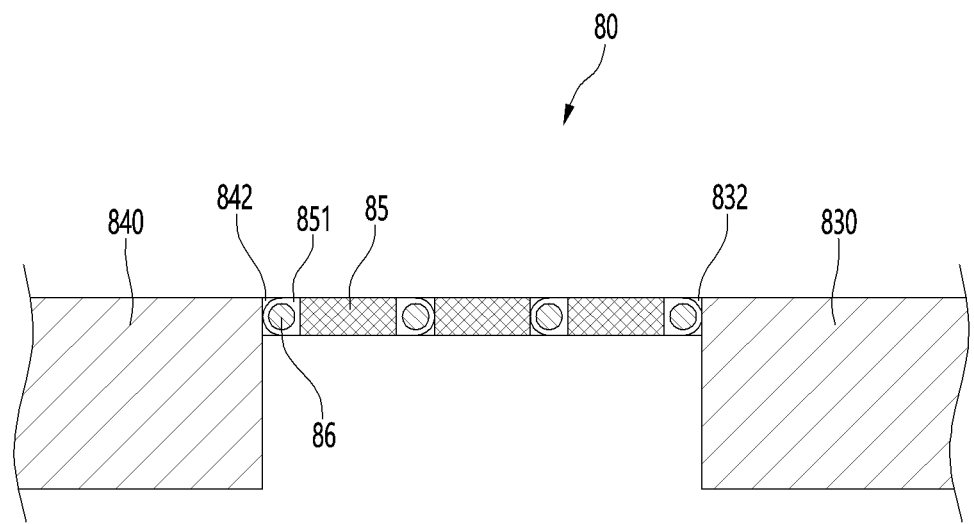
FIG. 50 is a partial longitudinal sectional view of a seating plate cut along 50-50 of FIG. 49.
Figure 51:
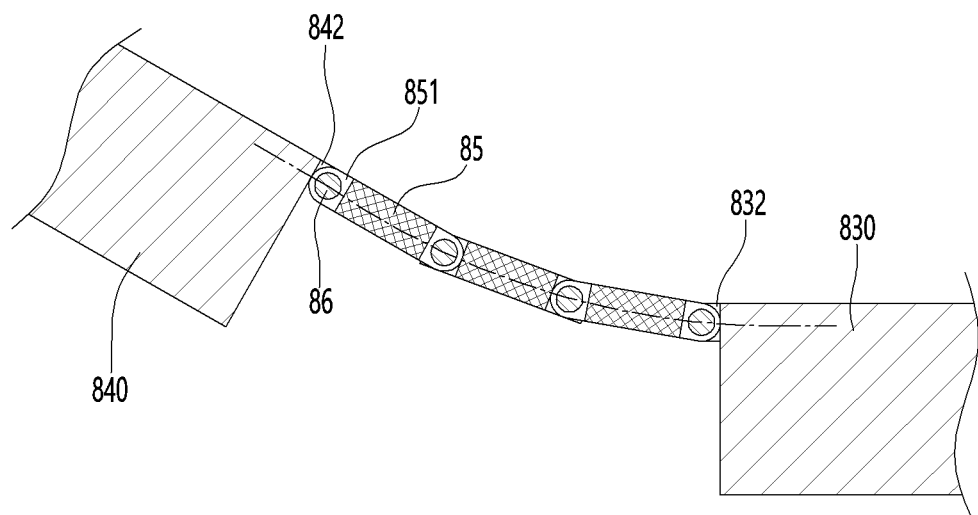
FIG. 51 is a partial longitudinal sectional view of the seating plate cut along 50-50 of FIG. 49 in a tilted state of the bedframe.

Referring to FIGS. 49 to 51, the plurality of firmness adjusters M1 (FIG. 48) may be fixed to an upper surface of the seat plate 80. The seat plate 80 may have a plate structure formed by a plurality of plates 810, 820, 830, 840 that are hinged or rotatably coupled to each other, the plurality of plates 810, 820, 830, 840 corresponding to sections of the bed frame 300 configured to be adjustable. The seat plate 80 may include an upper body plate 81 and a lower body plate 82, which may be provided on the upper body frame 3330 and lower body frame 3320 (FIGS. 33-44), respectively.

The upper body plate 81 may include a front plate 810 and a rear plate 820 rotatably connected to the front plate 810. The front plate 810 may be provided on a section of the upper body frame 3320 having the front frame 3322, and the rear plate 820 may be provided on a section of the upper body frame 3320 having the rear frame 3321 (see also FIG. 54).

Figure 54:
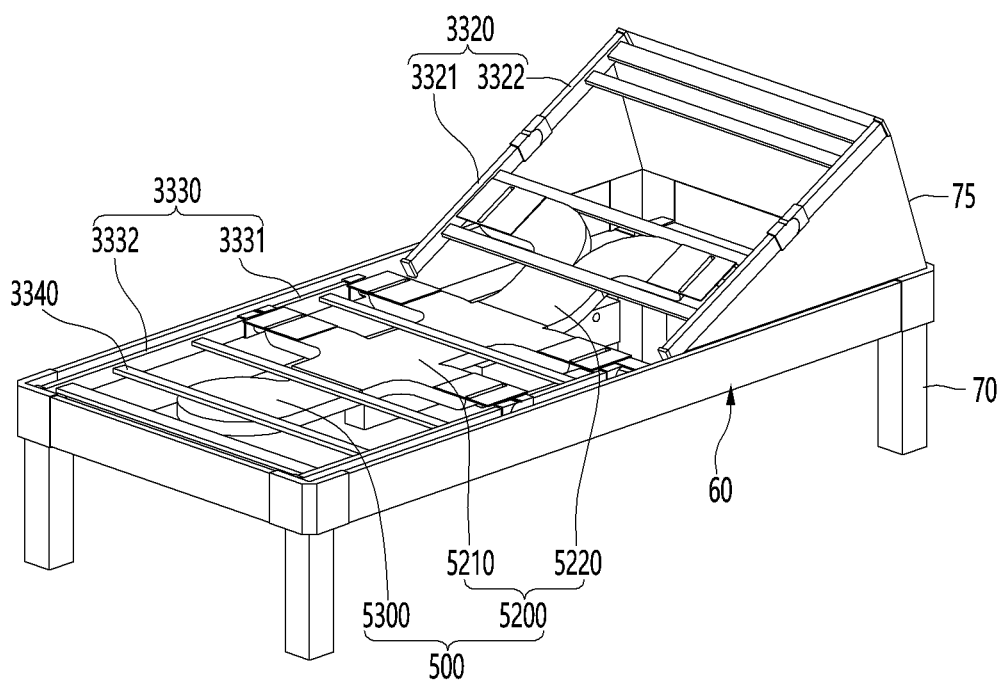
FIG. 54 is a perspective view of a bedframe showing a state in which the upper body frame is tilted.

The lower body plate 82 may include a front plate 830 and a rear plate 840 rotatably connected to the front plate 830. The front plate 830 may be provided on a section of the lower body frame 3330 having the front frame 3331, and the rear plate 840 may be provided on a section of the lower body frame 3330 having the rear frame 3332 (FIG. 54).

A plurality of fastening holes 811, 821, 831 and 841 may be formed in each of the plates 810, 820, 830, and 840, respectively. When the plurality of firmness adjusters M1 are seated on the seat plate 80, a plurality of fastening members (e.g., bolts or screws) may penetrate the fastening holes 811, 821, 831, 841 and the firmness adjusters M1. As an example, the structure described in FIG. 42 may be applied. A fastening boss may extend from the bottom surface of the bottom case 23 to be inserted into the fastening holes 811, 821, 831, 841, and the fastening members may be inserted into the fastening boss and holes 811, 821, 831, 841. The plates 810, 820, 830, and 840 may optionally include a plurality of holes through which air discharged from the dying module 50 may flow, depending on a configuration of the drying module 50.

As shown in FIGS. 50 and 51, adjacent plates among the plates 810, 820, 830, and 840 may be connected by one or more joint plates 85 and a plurality of joint hinges 86. A plurality of extension ends or protrusions 832, 842 may protrude from each of the ends of the plates 810, 820, 830, and 840. The plurality of extension ends 832, 842 may be spaced apart from each other at a predetermined interval in a width direction of the seat plate 80. The joint plates 85 may have a plurality of extension ends 851 which extend past the joint hinge 86, and the plurality of extension ends 851 may be configured to fit within or be engaged with the plurality of extension ends 832, 842 of the plates 810, 820, 830, and 840.

The plurality of extension ends 851, 821, and 842 may have teeth that engage or mesh with each other like gears. The plurality of extensions ends 851, 832, and 842 may be formed to have a plurality of protrusions and recesses. The plurality of extensions ends 851 may fit with the plurality of extension ends 832, 842 like pieces to a puzzle, as the protrusions of the extension ends 851 may fit within the recesses formed in the extension ends 832, 842.

The joint hinge 86 may pass through the extension ends 832, 842, 851 so that two abutting plates of the plates 810, 820, 830, and 840 may rotate or pivot relative to each other. When two plates of the plates 810, 820, 830, and 840 are directly connected by one joint hinge 86, a degree of freedom of bending of the plates 810, 820, 830, and 840 may be low. A bending degree of freedom of the plates 810, 820, 830, and 840 may be defined as a radius of curvature of a curve (as shown by the dotted line in FIG. 51). A high degree of bending freedom may correspond to a large a radius of curvature. The higher the degree of bending freedom, the smoother the plates 810, 820, 830, and 840 may appear when bent. When the joint plate 85 is provided, the degree of bending freedom may be increased. As a number of joint plates 85 increases, the degree of bending freedom may increase. The figures show three joint plates 85 between two adjacent plates (in FIGS. 50-51, between front and rear plates 830 and 840 of the lower body plate 82), but embodiments disclosed herein are not limited to a number of joint plates 85, and an appropriate number may be selected according to a desired tilting angle or degree of bending freedom.

A plurality of grooves of the extension ends 851 may engage with the plurality of extension ends 832 and 842 protruding from the side surfaces of the plates 810, 820, 830, and 840. The extension ends 851 may be formed at both front and rear ends or sides of the joint plate 85. Accordingly, the joint plate 85 and a side surface or end of a plate among the plates 810, 820, 830, and 840 may be meshed with each other. The joint hinge 86 may be a cylindrical rod passing through the grooves of the extension ends 832, 842, and 851. The joint hinge 86 may be a rotation axis between a joint plate 85 and an adjacent plate 810, 820, 830, and/or 840.

A portion where two adjacent plates are connected by one or more joint plates 85 may be defined as a joint bending portion. The joint bending portion may be a section including a plurality of joint plates 85 (e.g., three) and a plurality of joint hinges 86 (e.g., four) coupling the plurality of joint plates 85 to two adjacent plates 810, 820, 830, and/or 840.

Figure 52:
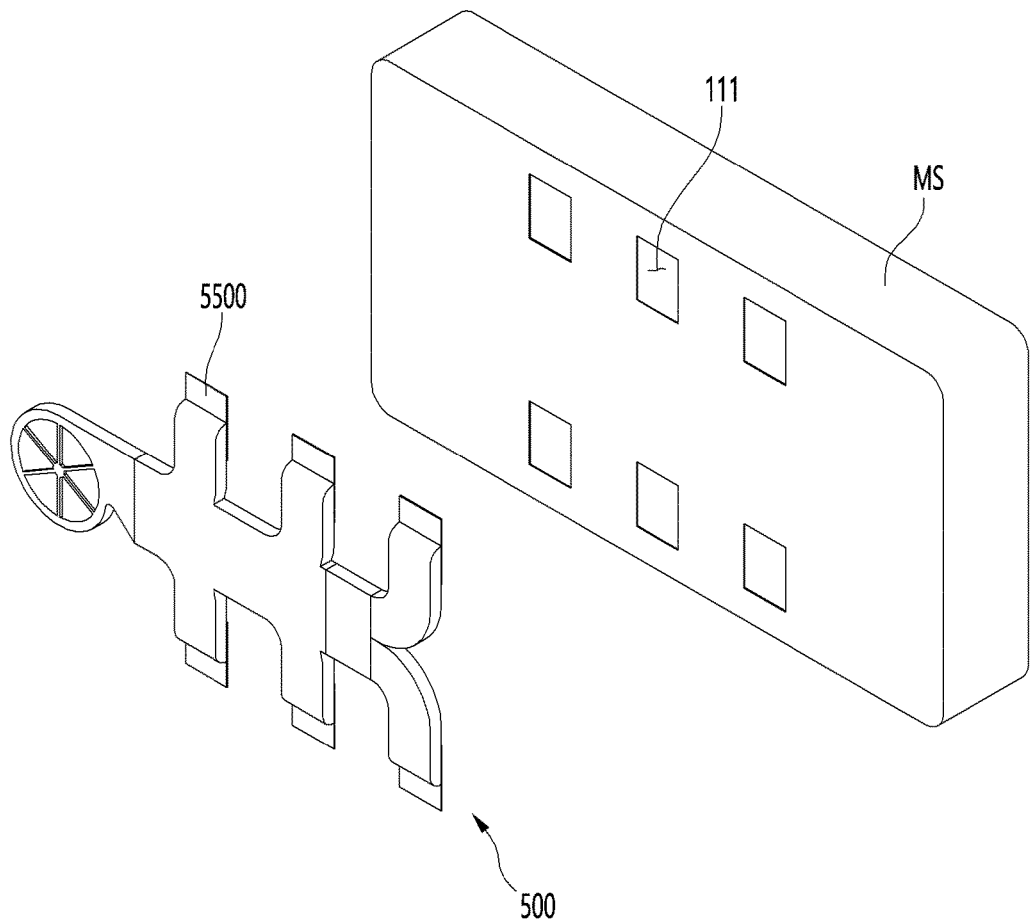
FIG. 52 is an exploded perspective view of a mattress set and a drying module constituting the bed of FIG. 45.
Figure 53:
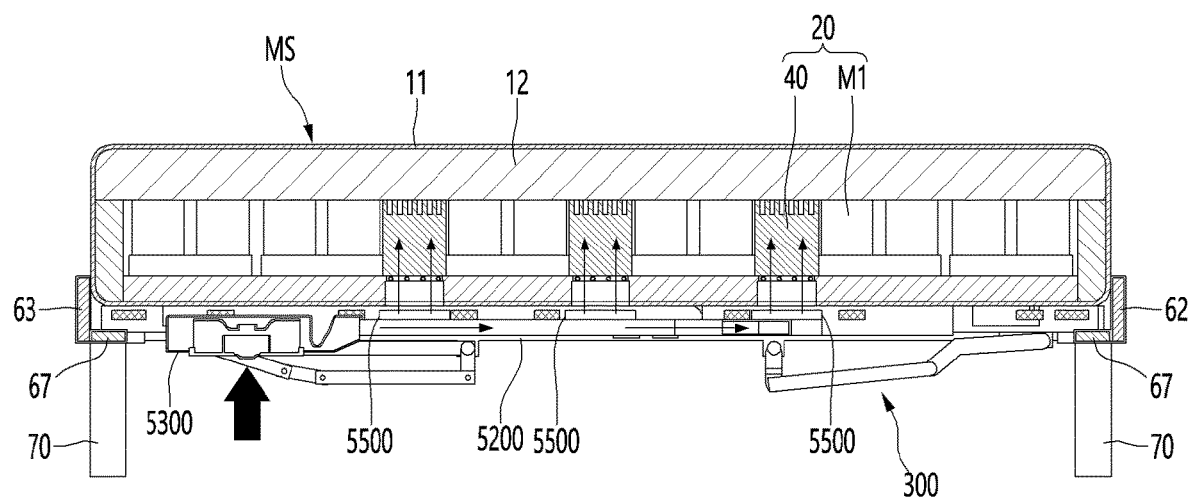
FIG. 53 is a longitudinal cross-sectional view of the bed taken along 53-53 of FIG. 46.

Referring to FIGS. 52 and 53, a bottom of the bed cover 11 may be formed with a plurality of guide or air holes 111 so that air supplied from the drying module 500 may be guided toward the topper 12. The plurality of guide holes 111 may align with joint bending portions in the seat plate 80 and/or the discharge ducts 550. A number of guide holes 111 may correspond to a number of discharge ducts 550.

When the mattress set MS is seated on the bedframe 300, the guide hole 111 and the discharge duct 550 may be aligned in a vertical direction so that the air discharged from the discharge duct 550 may be supplied into the mattress set MS through the guide hole 111. Air discharged from the discharge duct 550 may rise through gaps formed in the joint bending portion and may be guided to the partition 40. As shown in FIG. 44, when a plurality of ventilation holes 44 are formed in the partition 40, air may be easily transferred to the topper 12.

The fan 5300 may be provided under the user's feet when the user is lying down so that a disruption of noise from the fan 5300 during sleep may be reduced. A distance from an inner surface of the head frame 62 to an inner surface of the toe frame 63 may be designed to be longer than a length of the mattress set SM. While the mattress set SM is placed on the bedframe 300, an upper end of the toe frame 63 may be higher than a bottom of the mattress set SM. When the upper body frame 3320 is tilted upward, a rear end of the mattress set MS may be caught by the toe frame 63 and prevented from slipping downward.

As previously described, a stopper guard 68 may protrude from the upper end of the toe frame 63 to further prevent slipping. In addition, when the legs 70 are included, the dryer module 5000 may not require a suction duct, and air may be suctioned directly into the fan 5300.

Referring to FIG. 54, as previously described, an upper blocking film or layer 75 and a lower blocking film or layer 77 may cover gaps during an operation of the seating frame 3300. A part of the supply duct 5200 fixed to the upper body frame 3320 and/or the lower frame 3330 may be made of a hard duct 5210, and a part of the supply duct 5200 provided under the joint bending portions may be made of a soft or flexible duct 5220.

Figure 55:
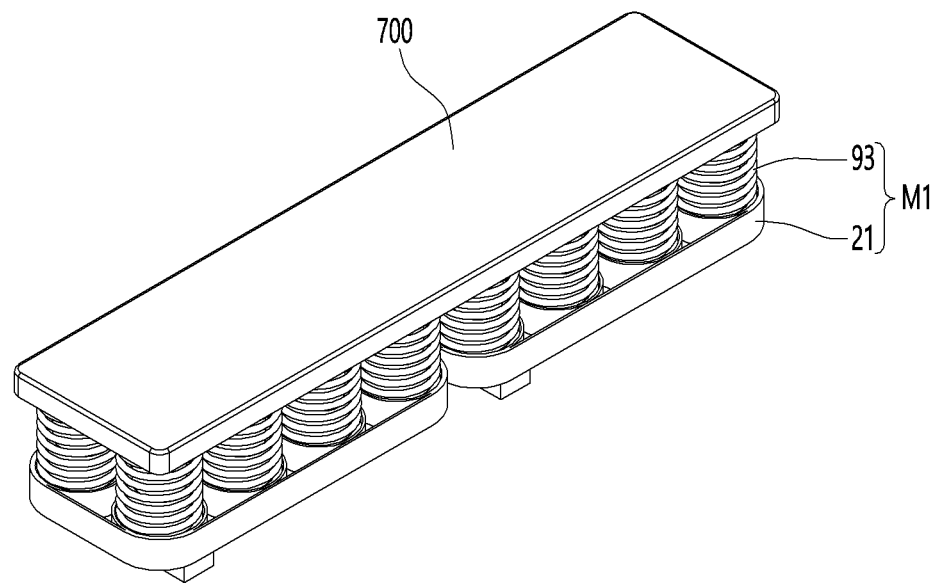
FIG. 55 is a perspective view of a firmness adjuster according to an embodiment in which a buffer plate is coupled to an upper surface of the cushions.
Figure 56:
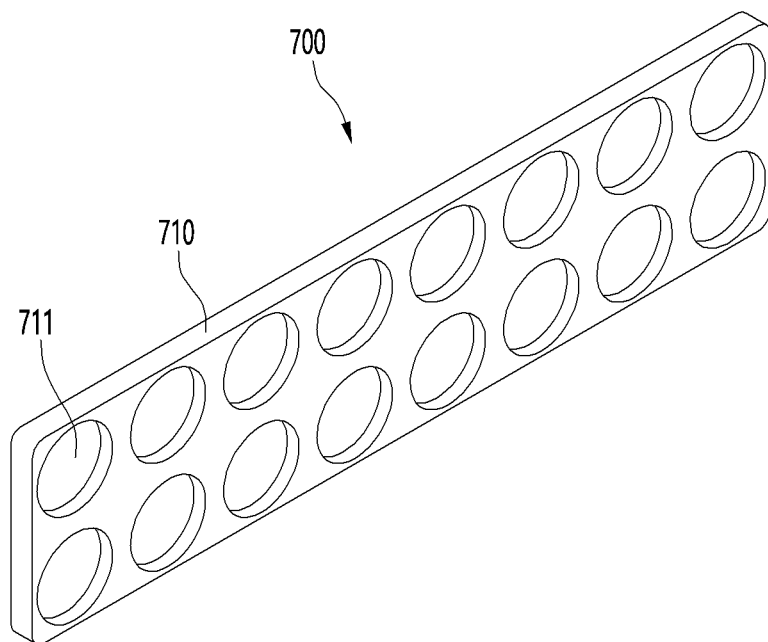
FIG. 56 is a bottom perspective view of the buffer plate.

Referring to FIGS. 55 and 56, at least one buffer plate 700 may be provided on top of the cushion module 20 to prevent or reduce discomfort from a back or waist pressing against the cushions C while the topper 12 is compressed. For example, there may be one buffer plate 700 that covers two adjacent firmness adjusters M1, as shown in FIG. 55, which may correspond to a section of the seating frame 3300 (e.g., a section above the upper body frame 3200, or a section above the front frames 3322) However, embodiments disclosed herein are not limited with respect to an arrangement of the buffer plate 700 and firmness adjusters M1.

The topper 12 may be a memory or latex foam material that is pressed flat by a vertical load and then returns or decompresses to an initial or original state when the load is removed. When a thickness of the topper 12 is too thin or the user's weight exceeds average, an amount of compression of the topper 12 may be large, and an upper surface of the cushion C, which includes outer and inner springs 93 and 94, may press against the user's back or waist, resulting in discomfort. Since there may be gaps between the plurality of cushions C, when lying down for a long time, the user's back or waist may be stiffened by the cushions C, causing discomfort.

In order to prevent such discomfort, the buffer plate 700 may be interposed between the topper 12 and the cushions C. The buffer plate 700 may be provided over firmness adjusters M1 of one row.

A length of the buffer plate 700 may correspond to the width of the topper 12, and a width of the buffer plate 700 may correspond to the width of the firmness adjuster M1. The width of the buffer plate 700 may mean the shorter side, while the length may mean the longer side. The buffer plates 700 may be arranged to reduce spaced or a height difference between cushions C, which may cause discomfort, while still allowing firmness adjustment of the firmness modules M1.

The buffer plate 700 may include a buffer body 710 having a predetermined thickness, width, and length, and a plurality of cushion receiving grooves or recesses 711 formed on the bottom surface of the buffer body 710. The buffer body 710 may have a rectangular shape with rounded corners, but embodiments disclosed herein are not limited.

Upper ends of the cushions C may be inserted into the plurality of cushion receiving grooves 711, which may provide added security to an arrangement of cushions C. Even if a portion of the mattress set SM is tilted by the bedframe 300, collisions between adjacent cushions C may be reduced or prevented by the cushion receiving grooves 711. The cushion receiving groove 711 may be similar to the cushion receiving groove or recess 123 described in FIGS. 5 and 6.

Hereinafter, a description of automatically adjusting the firmness of the bed by monitoring a sleeping position of the user will be described according to an embodiment. Such a method may be applicable to the beds 10, 10*a*, 10*b* described with reference to FIGS. 1-56.

Figure 57:
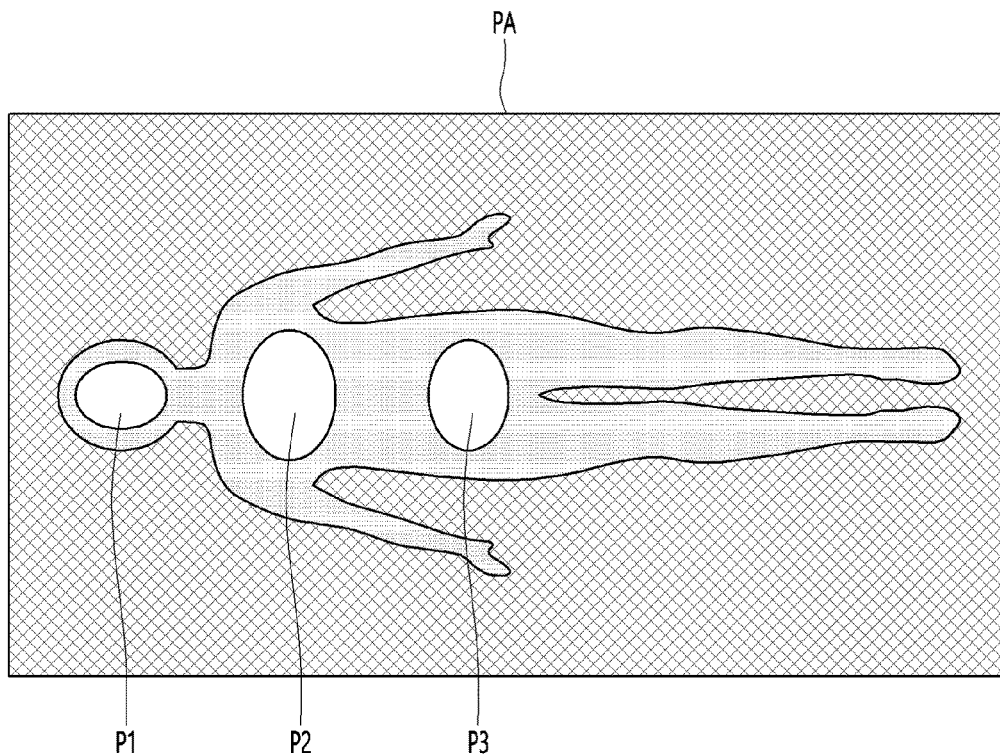
FIG. 57 is a view showing a point at which a user's weight to be laid upright is concentrated on a body pressure sensing sheet provided on a bed according to an embodiment.
Figure 58:
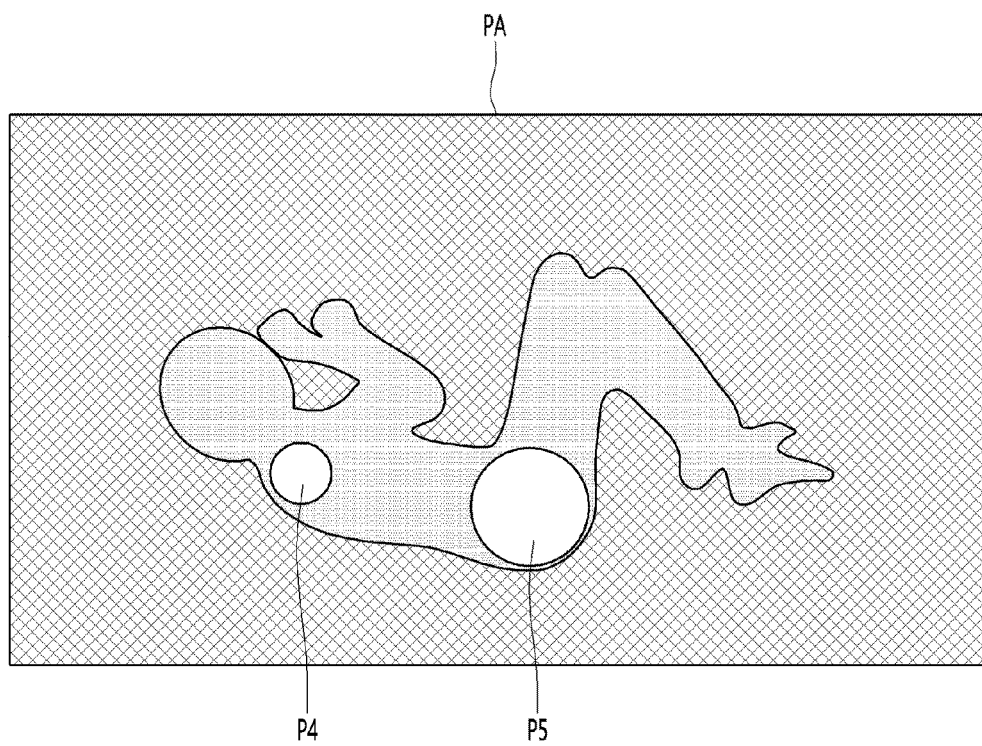
FIG. 58 is a view showing a point where weight is concentrated when a user lies on the side of the body pressure sensing sheet.

Referring to FIGS. 57 and 58, the beds 10, 10*a*, and 10*b* according to an embodiment may further include a body pressure sensing sheet PA configured to sense a pressure at particular regions or sections. The top sheet 11 may be implemented as the body pressure sensing sheet PA, or the body pressure sensing sheet PA may be an additional sheet provided above or below the top sheet 11. Embodiments disclosed herein are not limited.

The body pressure sensing sheet PA may include a fibrous pressure sensor that is thin and has high flexibility. The body pressure sensing sheet PA may feel like cloth. The body pressure sensing sheet PA may include a first layer having a plurality of first electrode lines arranged in a first (e.g., horizontal) direction, a second layer having a plurality of second electrode lines arranged in a second (e.g., vertical) direction, and an intermediate later provided between the first and second layers to reduce or prevent direct contact between the first and second electrode lines. The intermediate layer may include a conductive fabric whose resistance value may be changed by vertical pressure. Points where the first electrode line and the second electrode line intersect may be pressure measurement points.

Embodiments disclosed here are not limited to measuring pressure via the intersecting first and second electrode lines described above. The body pressure detection sheet PA may have various structures and/or include various types of fibrous body pressure detection sensors (e.g., weight or tension sensors) capable of measuring a body pressure or weight of the user.

A body pressure distribution may be sensed using the fiber-type body pressure sensor of the body pressure detection sheet PA, and based on a collective result of multiple measures at the pressure measurement points, different pressures in different sections of the bed that correspond to different firmness adjusters M1 may be sensed. A corresponding firmness adjuster M1 may be independently controlled based on a desired firmness and sensed pressure above the corresponding firmness adjuster M1. The body pressure sensing sheet PA may be attached to the top surface of the topper 12 or may be alternatively embedded in the topper 12.

A control box may be mounted on one side of the guard frame 60, and a microcomputer or a controller may be installed inside the control box. A body pressure value measured by the body pressure detection sheet PA may be transmitted to the controller, and the controller may process collected body pressure data through sampling and filtering processes.

The controller may create an image representing a distribution of body pressure for each body area of the user based on the processed data and output the image to a display. The display may be provided in the guard frame 60, remote controller, or may be a separate screen pad. Alternatively or in addition thereto, the image may be accessible via a mobile or web application that communicates with the controller, which may have a communication module (e.g., a WiFi or Bluetooth module). The body pressure distribution image as shown in FIGS. 57 and 58 may be displayed on the display. The display may be connected (e.g., wired or wirelessly via WiFi or Bluetooth) to the controller.

As shown in FIGS. 57 and 58, weight may be concentrated to specific parts P1 to P5 of the body according to a user's lying position. Body pressure may increase where weight is concentrated, so the body pressure detection sheet PA may sense relatively high pressure values at parts or sections P1 to P5. The controller may increase the firmness by operating corresponding firmness adjusters M1 that support a body part where body weight is concentrated and body pressure increases.

Hereinafter, a method of automatically or manually adjusting the firmness at an area where weight is concentrated will be described in detail through the flowchart of FIG. 59. During firmness control according to a first embodiment, the controller may automatically adjust firmness of the bed so that the bed may have a uniform firmness. The automatic control may be based on the body pressure distribution data transmitted from the body pressure detection sheet PA described above. However, embodiments disclosed herein are not limited. For example, the firmness of the bed may be adjusted so that a left side corresponding to a left user has a first uniform firmness, and the firmness of the bed at a right side corresponding to a right user may be adjusted to have a second uniform firmness. In other embodiments, the user may be able to select via a user interface (e.g., provided on the display and/or the guard 60) predetermined firmness levels for each region of the bed that corresponds to a firmness adjuster M1.

Figure 59:
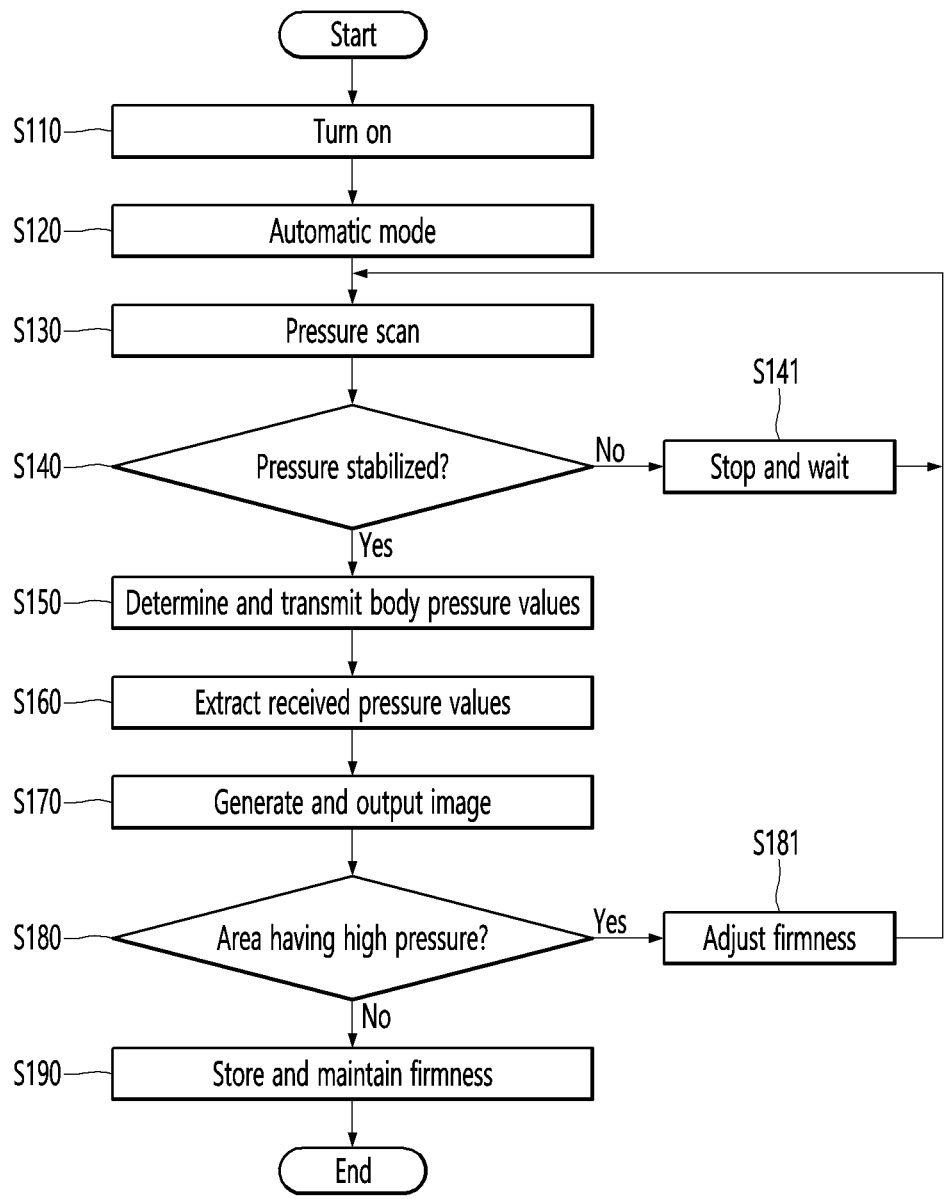
FIG. 59 is a flowchart showing a method of controlling the firmness of a bed of FIG. 1.

Referring to FIG. 59, first, the user may turn on the bed to supply power to the bed 10, 10a, or 10b (S110). The user may lie on the bed 10, 10a, or 10b before or after turning the bed 10, 10a, or 10b on. For example, the user may be able to turn the bed 10, 10a, or 10b on via a remote control or a button on an inner surface of the head frame 62.

When the bed 10, 10a, or 10b is turned on, the motion controller 30 or 300 may be turned on, along with the body pressure sensing sheet PA and a body pressure regulator or controller 800 to be described later. The body pressure regulator 800 may be a user interface (e.g., remote control, mobile or web application) through which the user may select desired firmness levels. The controller may also be turned on.

The user may select an "automatic mode" by operating the body pressure regulator 800 (S120). For convenience of description, the body pressure regulator 800 will be described as a remote controller (shown in FIG. 60) that is wirelessly connected to the controller (e.g., via Bluetooth or WiFi). One of ordinary skill in the art will know that the controller may include a microcomputer and/or processor mounted on a printed circuit board (PCB) provided in the control box.

Figure 60:
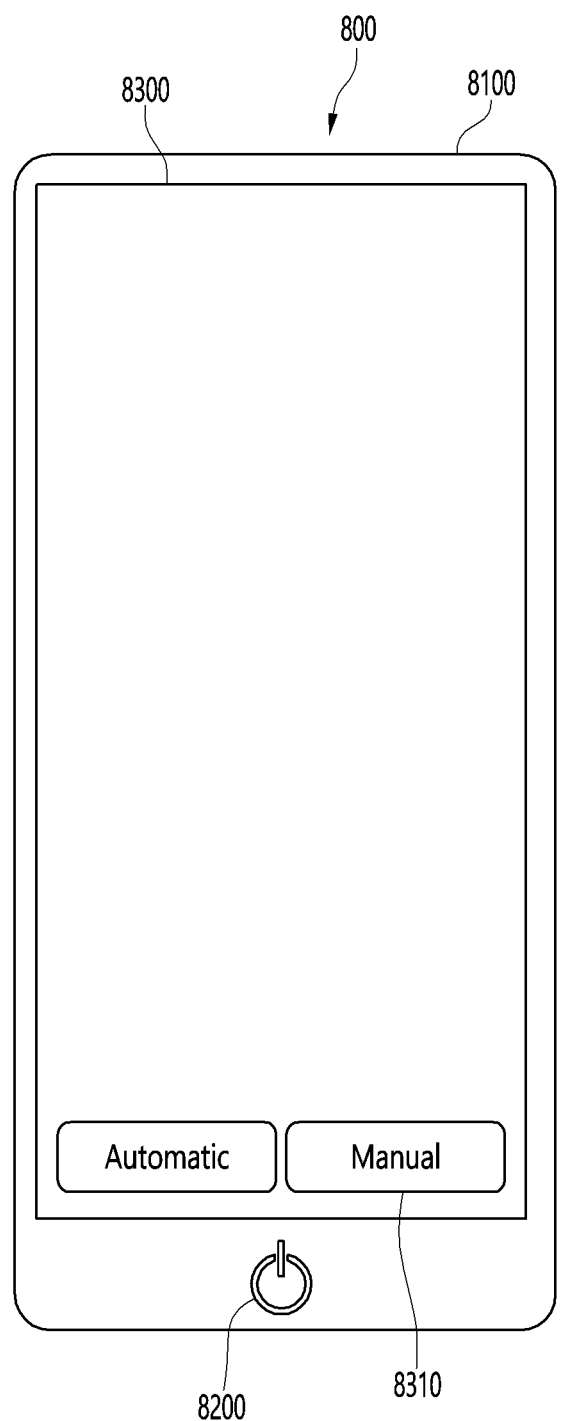
FIGS. 60 to 63 are display screens of the body pressure regulator shown in the process of performing the method of controlling the cushion strength of the bed of FIG. 1.

Referring quickly to FIG. 60, the body pressure regulator 800 may include a main body 8100, a power button 8200 provided on the front side of the main body 8100, and a display 8300 provided on the front side of the main body 8100. The body pressure regulator 800 may be provided with a plurality of mechanical input buttons below the display 8300 and/or or a plurality of touch input buttons on the display 8300. The power button may be a mechanical button that the user must press with a certain amount of force. Embodiments disclosed herein are not limited to an implementation of the power button 8200 or other buttons.

When the user presses the power button 8200, the display 8300 may be activated, and the body pressure regulator 800 and the controller may be wirelessly connected or coupled to communicate (via, e.g., communication modules having WiFi or Bluetooth modules). The display 8300 may display menu items or regions.

For example, while the display 8300 is activated, the user may operate a menu button 8310 to select between the "automatic mode" and a "manual mode" displayed on different sides of the screen display 8300. The body pressure regulator 800 may optionally include a speaker or a light indicator.

The user may initiate the automatic mode by touching a menu button 8310 provided below the automatic mode display (e.g., the left button 8310), and an automatic mode command may be transmitted to the controller through a short-range wireless communication module embedded in the control box. The short-range wireless communication module may include Wi-Fi, Bluetooth, ZigBee, etc. Hereinafter, the controller provided in the control box of the bed will be referred to as a main controller.

Referring back to FIG. 59, when the automatic mode command is received by the main controller, the main controller may transmit a body pressure detection command to a controller of the body pressure detection sheet PA. A body pressure scanning process of detecting body pressure at a plurality of body pressure detection points or areas formed on the body pressure detection sheet PA may be performed (S130). The controller of the body pressure sensing sheet PA may be referred to as a sub controller. The body pressure scanning operation may be performed repeatedly a predetermined number of times within a predetermined time frame, and a plurality of measurement data corresponding to a plurality of times may be extracted for any given point.

The scan may be determined to be complete when measurement data corresponding to a given point is maintained in a predetermined range, indicating that pressure or detection has stabilized at the given point. Whether the body pressure has stabilized based on sensed pressure values being inside the predetermined range may be determined (S140) by the sub controller. For example, when a person lying in bed turns, sensed body pressure values may fluctuate in a very large range outside of the predetermined range, and in this state, an accurate body pressure value may not be obtained. In this example, the sub controller may determine that the body pressure is not stable ("No" after S140). If the body pressure is detected a predetermined number of times at a predetermined time interval and a variation of the body pressure values determined number of times whether the predetermined range, the sub controller may determine that the body pressure scan process has been normally performed and/or that the body pressure has stabilized ("Yes" after S140).

Figure 61:
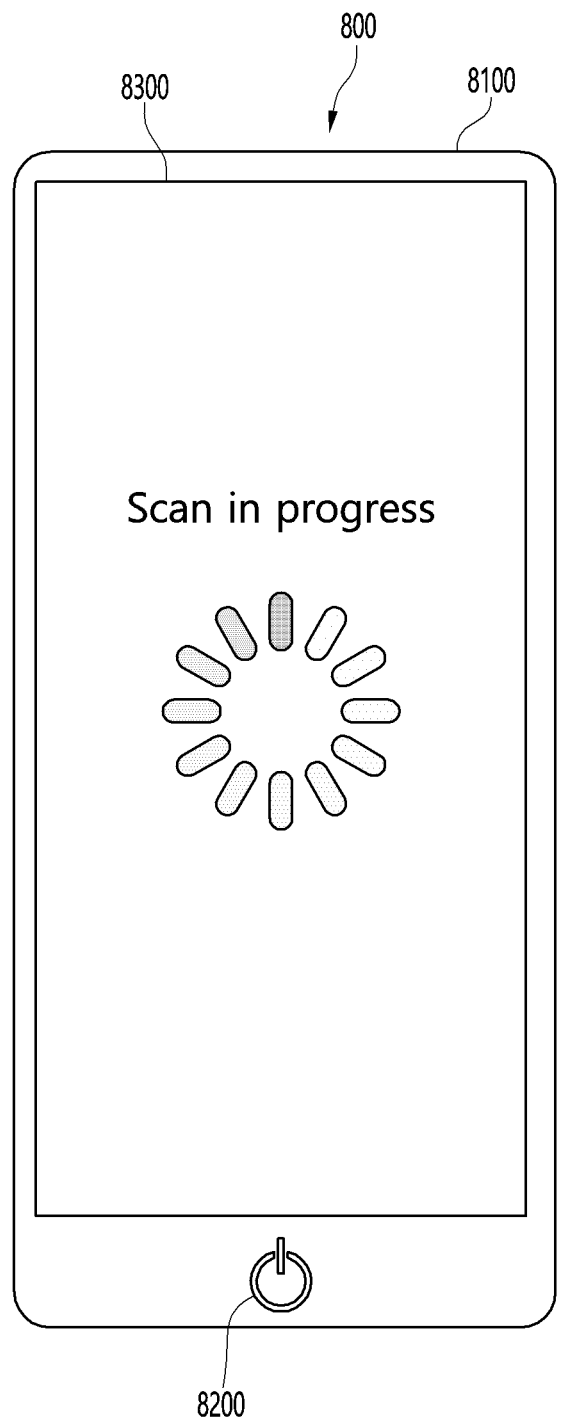

If it is determined that the pressure has not stabilized ("No" after S140), the sub controller may stop the body pressure scan for a predetermined time and wait (S141), and when a predetermined time elapses, the body pressure scanning process (S130) may be resumed or repeated. If it is determined that a fluctuation range of the body pressure values, the body pressure scanning prochin the predetermined range (ngetermined nge o, an average value of the body pressure values ues, the body pressure scanning prochin the 0) nge of a plurality of body pressure values t must be maa certReferring quickly to FIG. 61, when an automatic mode is selected and a body pressure scan is started, information indicating that a body pressure scan is currently in progress may be output on the display 8300 of the body pressure regulator 800.

The information may be provided by any one of text, image, sound, video, or a combination thereof.

Referring back to FIG. 59, once it is determined that the body pressure scan has been completed because the pressure has stabilized ("Yes after S140), and after the body pressure values at points are determined based on an average of values, the controller may transmit the determined body pressure values to the main sub controller (S150). The main controller may extract body pressure values for each body region by processing and analyzing the body pressure values need time are performed at (controller (S160).

The main controller may generate a body pressure distribution image using the extracted body pressure values for each body region and transmit the body pressure distribution image to the body pressure regulator 800. The transmitted body pressure distribution image may be output on the display 8300 of the body pressure regulator 800 (S170).

Figure 62:
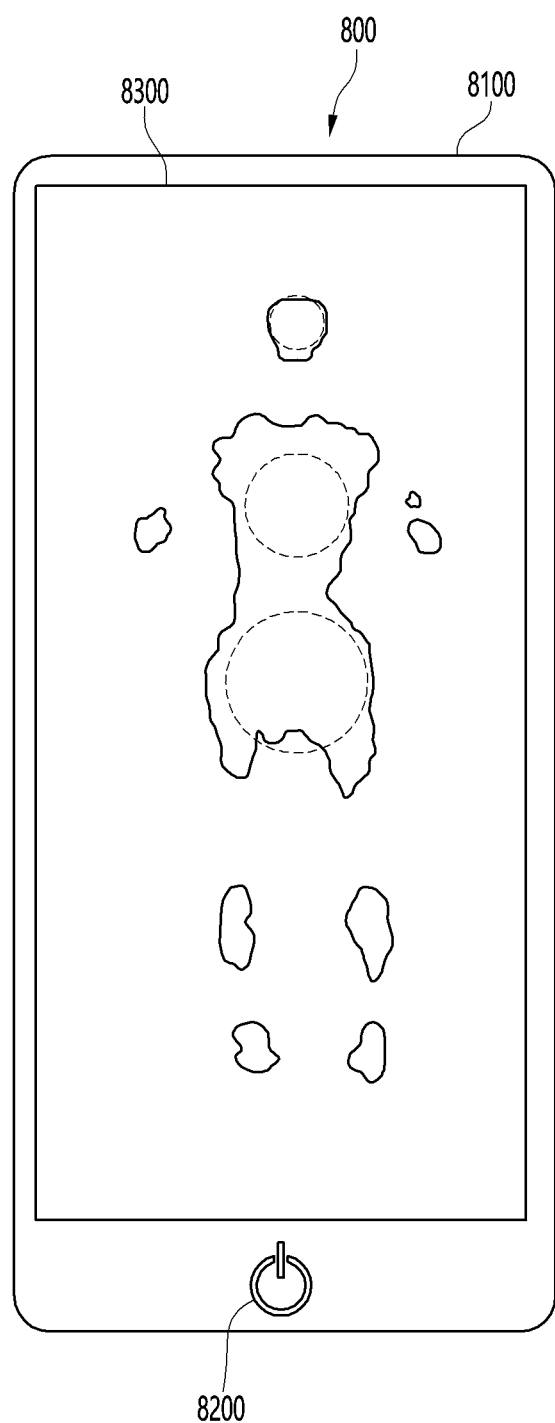

Referring to FIG. 62, a body pressure distribution image generated by the main controller may be expressed as a color or graded image. For example, a point or area determined to have a relatively high pressure value due to a concentration of body weight may have a red color, and a point or area determined to have a relatively low pressure value may have a blue color. Pressure values in between may have colors in between red and blue on the color spectrum. The main controller may optionally normalize sensed pressures over time or across the points or areas to determine which pressures may be considered high for a user and which pressures may be considered low, but embodiments disclosed herein are not limited.

Referring to the dotted line portion of the body pressure distribution image shown in FIG. 62, body pressure may be detected high at the user's head, shoulders, and hips while the user is lying down. Referring back to FIG. 59, the main controller may determine whether there is an area where body pressure is concentrated compared to other areas based on the extracted body pressure data for each body area (S180).

When it is determined that there is an area in which the body pressure value exceeds a predetermined range or value ("Yes" after S180), the main controller may operate the cushion module 20 to adjust (e.g., increase) the firmness at the corresponding area (S181). A range may be determined as a difference between a highest determined pressure and a lowest determined pressure among the areas, and if such a range is larger than the predetermined range, the corresponding area to be adjusted may correspond to the area having the highest determined pressure. As an alternative example, the predetermined range be a difference between a highest determined pressure and an average pressure among the areas or points, and if such a range is larger than the predetermined range, the corresponding area to be adjusted may correspond to the area having the highest determined pressure. In yet another example, if a pressure value sensed in an area exceeds a predetermined pressure, the firmness of such an area may be adjusted. Embodiments disclosed herein are not limited.

Referring back to FIGS. 21 and 27, the main controller may generate a control signal to the motor 24 of the cushion module 20 so that the motor 24 rotates in one direction. A rotational force of the motor 24 may be transmitted to the drive gear 251 and the transmission gear 990 so that the inner case 92 of the cushion C rises.

As the inner case 92 rises, the inner spring 94 also rises, thereby increasing the firmness of the cushion C. As the firmness of the cushion C may increase, the body pressure value sensed in the area above the cushion C may decrease. During an adjustment process (S181), pressure may be continuously sensed (e.g., in short time increments), and when the sensed body pressure value at the area decreases such that a determined range (as described above) falls within the predetermined range, the adjustment process S181 may stop. When the body pressure adjustment in the area is completed through this method, a current firmness of the cushion module 20 and/or the firmness adjuster M1 at the corresponding area may be stored and maintained in a memory of the main controller or controller (S190). Alternatively or in addition thereto, a firmness adjuster M1 may be controlled to lower the inner case 92 based on a comparison between the sensed pressure and a predetermined pressure or predetermined pressure range.

Figure 63:
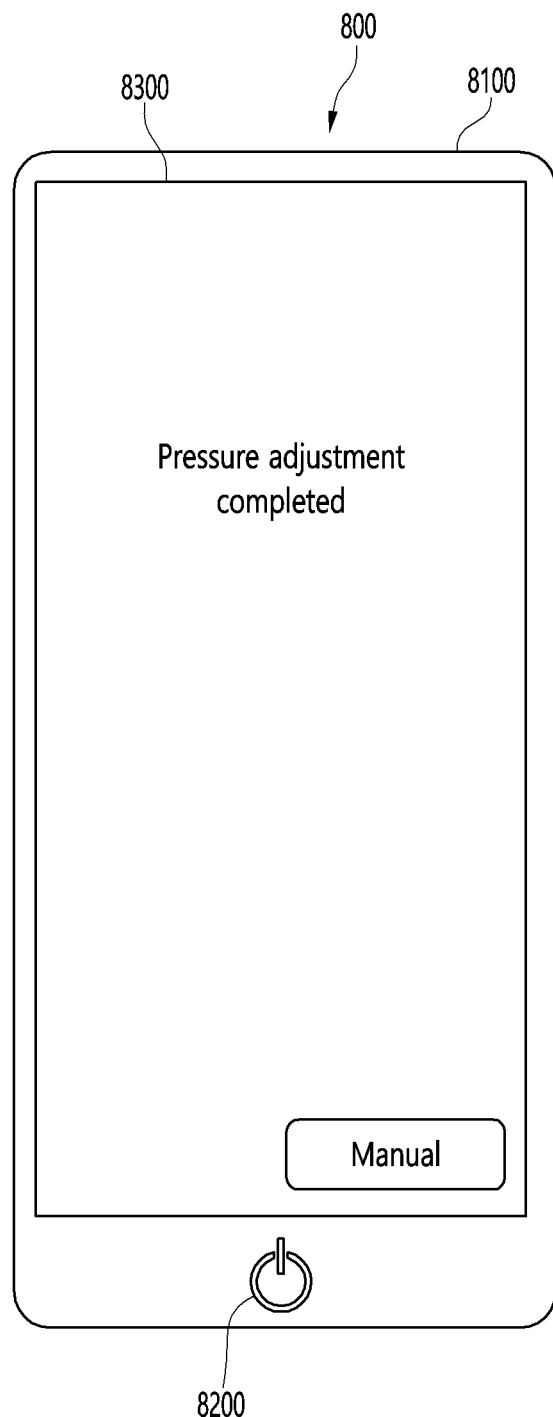

Referring to FIG. 63, when the body pressure adjustment is completed, a message indicating that the body pressure adjustment is completed may be displayed on the display 8300 of the body pressure regulator 800. In addition, a message recommending that the user touch or operate the manual mode button may be displayed if the body pressure control is to be manually readjusted.

In a method of controlling the firmness of the bed according to a second embodiment, the manual mode may be selected after the automatic adjustment method described above, or the manual mode may be selected by the user at the beginning so that the user may directly adjust the firmness of the bed.

Figure 64:
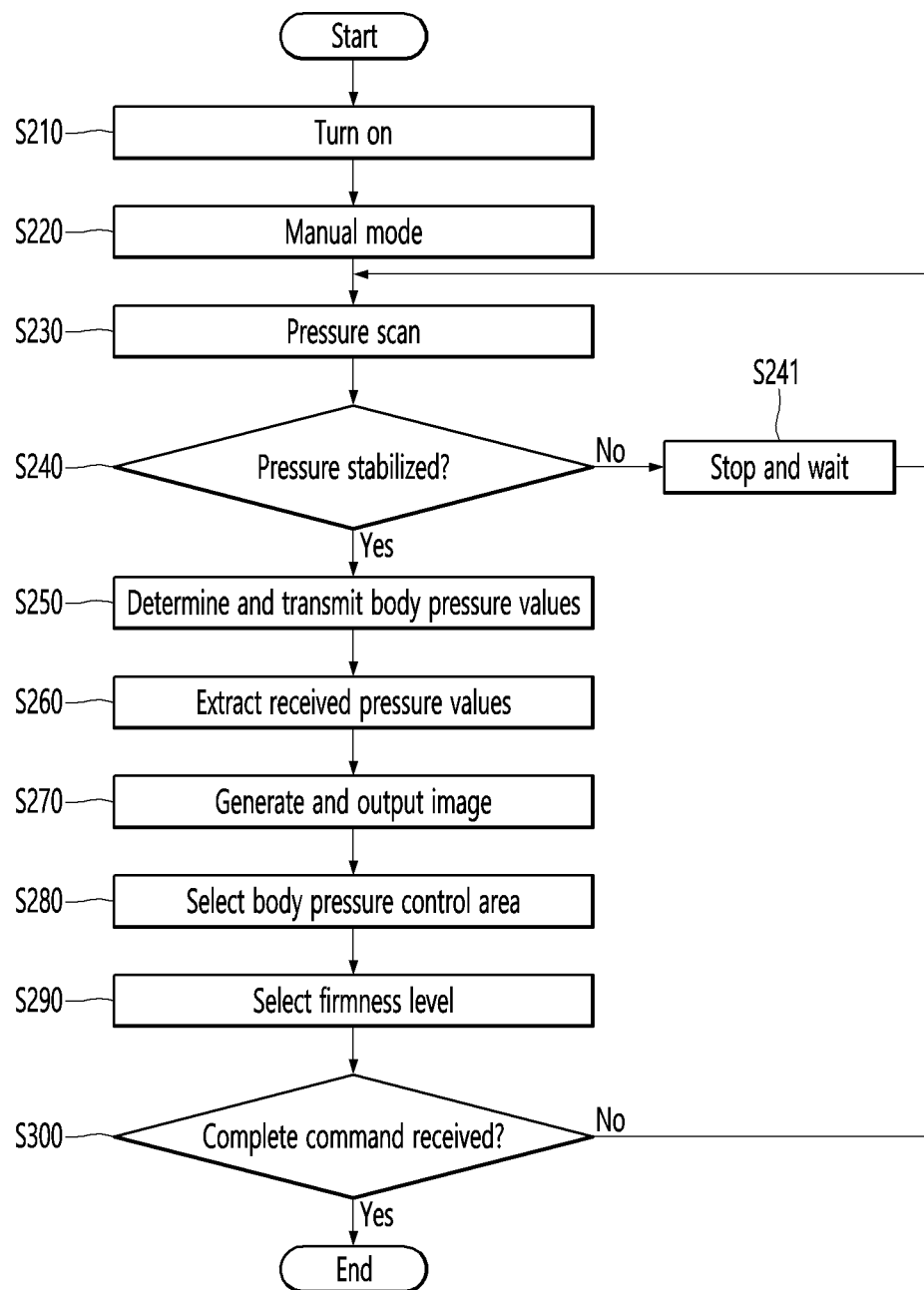
FIG. 64 is a flowchart showing a method of controlling the firmness of a bed according to another embodiment present invention.

Referring to FIG. 64, first, the power of the beds 10, 10a, and 10b may be turned on by the user (S210), and the user may select the manual mode (S220). If the user selects the manual mode right after the automatic mode is completed, the process of turning on the bed may be omitted.

When the manual mode is selected by the user while the bed is powered on (S220), a body pressure detection command may be transmitted from the main controller to the body pressure detection sheet PA. The body pressure detection sheet PA may perform a pressure scan (S230), and, like the previous steps S140 and S141, whether the sensed pressure values may be determined (S240), and if the pressure values have not stabilized, the scan may be paused for a predetermined amount of time (S241) before the pressure scan is resumed or repeated (S230). Once the sensed pressure values have stabilized, the body pressure detection data may be calculated and transmitted to the main controller (S250). The main control may extract the body pressure for each body area through processing (S260) and a body pressure distribution image may be generated and output (S270).

Steps S210 through S270 may be similar to Steps S110-S170 in FIG. 59 and repetitive details may be omitted. However, under the manual mode, there is a difference in that the body pressure distribution image may be output as a part of a body pressure control screen of the display 8300, which may be optionally interactive (see FIG. 65). When the body pressure control screen is output on the display 8300 (S270), the user may select a body pressure control area to be adjusted (S280) and a firmness level at the selected area (S290).

The controller or main controller may periodically sense whether a complete command has been input (S300), and when the command has been input ("Yes" after S300), the manual control mode may end. Otherwise, ("No" after S300), the body pressure detection sheet PA may continue to sense body pressures and update the image output on the display 8300.

Figure 65:
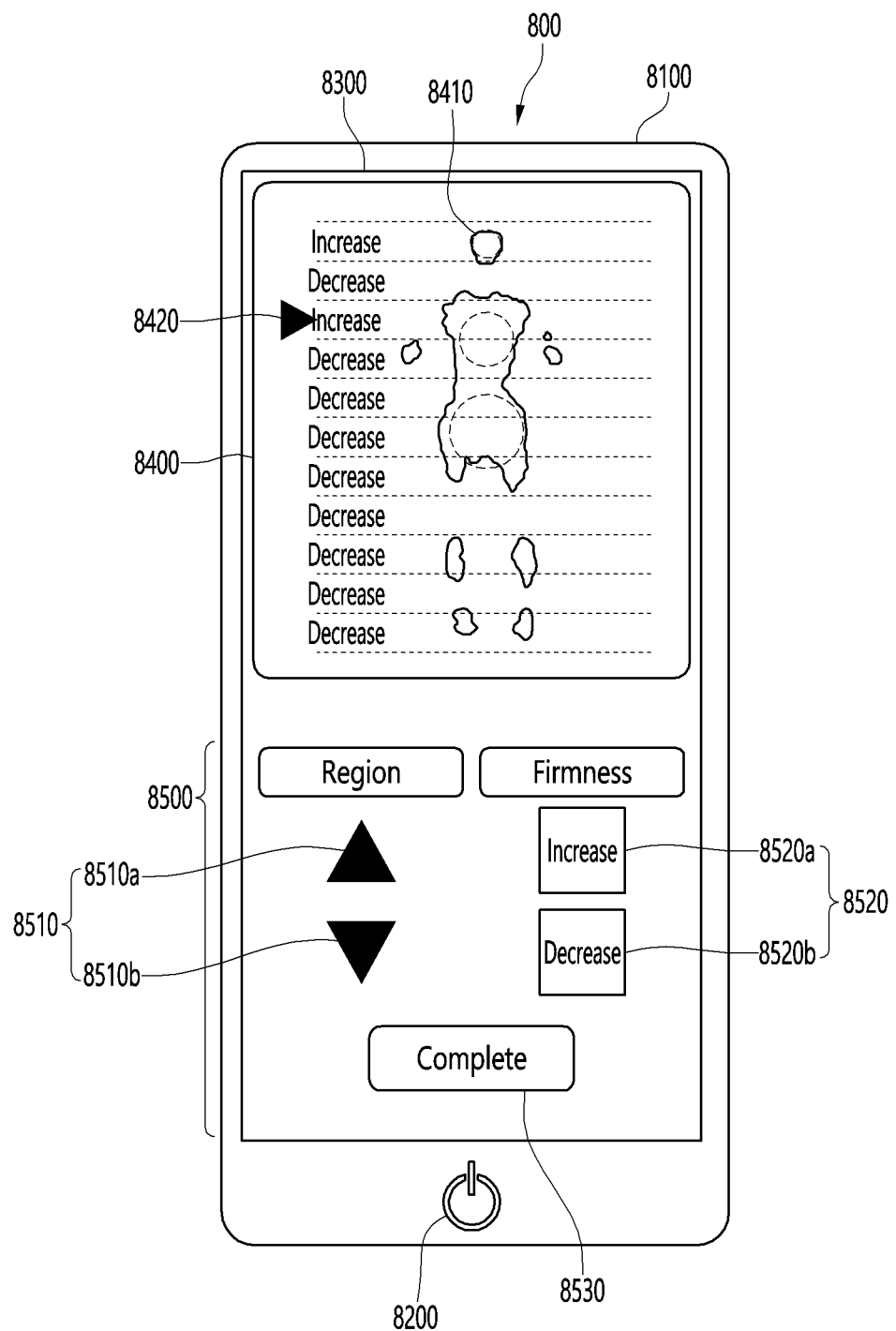
FIGS. 65 and 66 are display screens of a body pressure regulator shown in a process of performing a method for controlling a firmness of a bed according to another embodiment.

Referring to FIG. 65, on the display 8300 of the body pressure controller 800, an adjustment region search screen 8400 and an adjustment region menu screen 8500 may be displayed together. The adjustment region menu screen 8500 may include an adjustment region change button 8510 used for the user to select a firmness level, and a cushion firmness change button 8520 to newly set the firmness in a selected area or region. A completion button 8530 may be used to input a command to complete a manual firmness adjustment process.

The adjustment region change button 8510 may include an upper movement button 8510a and a lower movement button 8510b to raise or lower, respectively, a position of the cursor 8420. The adjustment region search screen 8400 may show a body pressure distribution image 8410 divided into a plurality of areas from head to toe, and a cursor 8420 provided at an edge of the adjustment region search screen 8400

In order to select a point at which the user wants to change the firmness of a firmness adjustor M1 of the cushion module 20, when the user touches or presses the adjustment region change button 8510, the cursor 8420 may appear on the screen and/or move. When the user touches the upper movement button 8510a several times for a short time or continuously for a long time, the cursor 8420 may moves upward in steps or rapidly move upward, respectively. Through this operation, the cursor 8420 may be positioned at a vertical position corresponding to a region to be selected.

When the cursor 8420 is positioned at a point or area where body pressure is selected to be concentrated, the user may increase the firmness at the selected point by operating the cushion firmness change button 8520. For example, when a firmness increasing button 8520a is pressed several times or pressed for a long time, the firmness at the point indicated by the cursor 8420 may be increased, and the firmness adjustor M1 may be controlled accordingly, When a firmness decreasing button 8520b is pressed several times or pressed for a long time, the firmness at the point indicated by the cursor 8420 may be decreased. As an example, the firmness at some areas may be selected to be at a stronger level than other areas by using the cursor 8420 to independently control various firmness adjustors M1 corresponding to the selected areas.

During the manual adjustment process, a pressure scan (S230) may be repeatedly performed, and steps 240 through 270 may be repeatedly performed so as to update the body pressure distribution image on the display 8400. The user may readjust firmness based on the updated body pressure distribution image on the display 8400.

This process may be repeated many times before the user touches the completion button 8530 to complete the body pressure adjustment process. In addition, the firmness adjustment completion command may be transmitted to the main controller.

Figure 66:
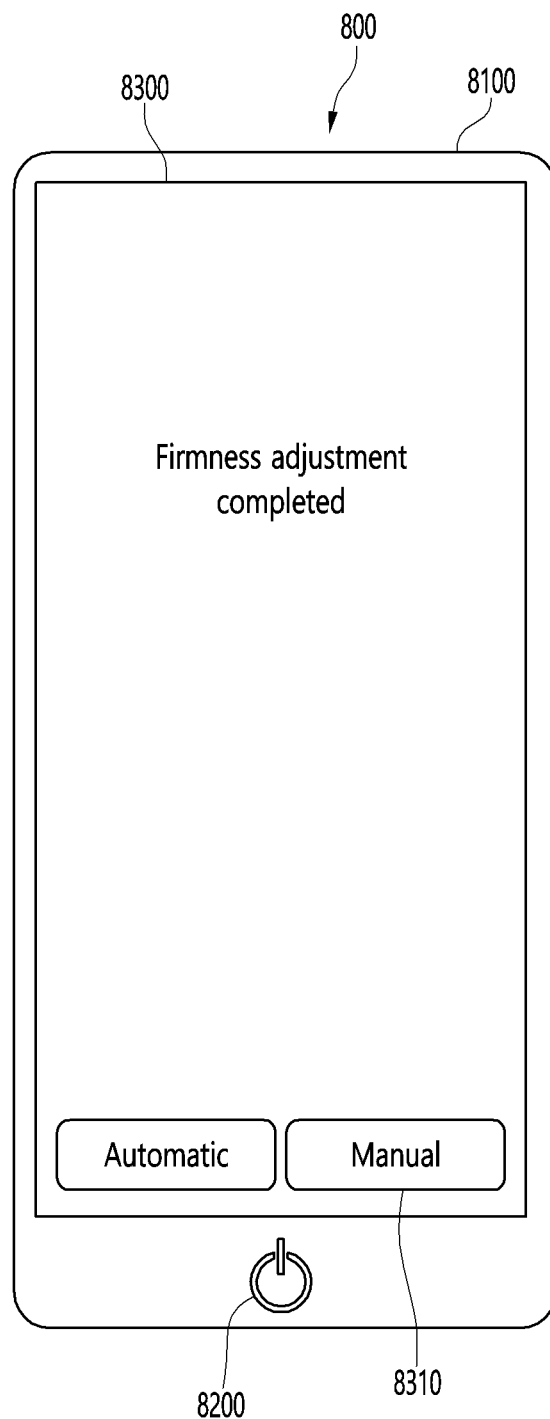

When the firmness or body pressure adjustment process is all completed, a message indicating that the firmness adjustment process has been completed may be displayed on the display 8300, as shown in FIG. 66. Further, when the firmness is automatically or manually re-changed, a message recommending the user to touch a button to select a desired mode may be displayed together. Embodiments disclosed herein may facilitate an improved sleeping condition and posture.

Embodiments disclosed herein may provide a bed including a topper having an upper surface that a user's body touches, at least one firmness controller or adjuster capable of adjusting a cushion strength or firmness, and a motion controller or bedframe supporting the firmness adjuster and capable having at least a portion tilted.

A mattress provided on the bedframe may include a plurality of cushion or firmness adjustment modules fixed to an upper surface of the motion controller. Each of the plurality of cushion modules may include a case, a plurality of cushion members or cushions seated in the case, and a driving means or drive to adjust the firmness of the plurality of cushions by gear coupling with the plurality of cushions.

Embodiments disclosed herein may be implemented as a bed comprising a topper that the user's body touches on an upper surface, a firmness controller supporting the topper and capable of adjusting a cushion strength or firmness, and a motion controller or adjustable bedframe supporting the strength controller and at least partially tiltable together with the strength controller.

The strength controller may include a plurality of strength control modules or firmness adjusters fixed to an upper surface of the motion controller, and the plurality of strength control modules may include a cushion member or cushion provided with at least one elastic body. A power transmission means may adjust the cushion strength of the plurality of cushion members.

Embodiments disclosed herein may be implemented as a bed comprising a topper that the user's body touches, a strength or firmness controller supporting the topper and including a plurality of strength or firmness control modules capable of adjusting cushion strength, a motion controller or bedframe in which a plurality of intensity control modules are coupled to an upper surface, and at least a portion of which is tiltable together with the strength controller, and a drying module or dryer coupled to the motion controller from a lower side of the strength controller to supply indoor or ambient air toward the topper.

Since a height of an inner spring provided inside the cushion member may be adjusted, the user may easily set the desired level of firmness. The firmness may be linearly adjusted through to height adjustment of the inner spring. By connecting the drive to a transmission gear provided at a lower end of the cushion member, the firmness of a plurality of cushions may be simultaneously adjusted by just one drive.

The strength controller may include a plurality of strength control modules or firmness adjusters. One strength control module may include a plurality of cushion members arranged in a width direction of the bed, and in a length of the bed. The user may adjust the cushion strength of the mattress differently for each body part, thereby providing an optimal or advantageous sleep state.

Since a part of the bed may be tilted through an operation of the motion controller, the user may have a better or customizable sleeping posture. Separating and replacing the topper may be easy and convenient, and replacing or repairing the strength control module may be convenient when the topper is separated.

By installing the drying module at the bottom of the bed, mold on the topper may be prevented. In addition, since the topper may be maintained in a dry state above a certain dryness level, comfort may be improved when the user touches the cool or dry bed, thereby helping the user to get a good night's sleep.

By a fiber-type body pressure sensor, embodiments disclosed herein may quickly identify where a user's body pressure is concentrated when the user lies on the bed. Based on body pressure value data detected by the body pressure sensor, a cushion strength in an area where body pressure is concentrated may be appropriately adjusted through an automatic or manual operation of the firmness or intensity control module, thereby improving a quality of life and sleep.

Embodiments disclosed herein may be implemented as a bed comprising a mattress having a prescribed width and a prescribed length, the mattress having a plurality of cases. Each case may include a plurality of cushions provided in the case, a drive coupled to the case, and a plurality of driving gears configured to transmit a force from the drive to the plurality of cushions such that a firmness of the cushions in the case may be adjusted when the drive may be operated. The mattress may include a top pad provided over the plurality of cushions of the plurality of cases, and a cover provided to surround the top pad and the plurality of cases.

The bed may further comprise a main frame having a first frame rotatably coupled to a second frame such that a posture of the main frame may be adjustable, and a guard surrounding sides of the main frame and mattress. The mattress may include a partition provided along a direction of the prescribed width and between a pair of adjacent cases. At least one of the partition, the top pad, or the guard may be made of an elastic foam material.

The main frame may have a first frame configured to support a first section of a user's body, a second frame hinged to the first frame and configured to support a section of a user's upper body and hinged to the first frame, a third frame configured to support a first section of a user's lower body and hinged to the first frame, a fourth frame configured to support a second section of a user's lower body and hinged to the third frame, a first actuator configured to rotate the first frame with respect to the second frame, and a second actuator configured to rotate the third frame with respect to the first frame.

The mattress may include a top pad provided over the plurality of cushions of the plurality of cases. The top pad may include a plurality of sleeves protruding from a bottom surface. The plurality of sleeves may be configured to surround upper ends of the plurality of cushions.

Each cushion may include a first elastic member, a second elastic member surrounding the first elastic member, a screw configured to change a height of the first elastic member with respect to the second elastic member when the screw may be rotated, and a transmission gear configured to rotate the screw and configured to engage with at least one drive gear of the plurality of drive gears.

The drive may include at least one of an actuator or a motor. The plurality of drive gears include a first gear coupled to a rotation shaft of the drive, at least one second gear engaged with the first gear, and a plurality of third gears provided between adjacent transmission gears. The second gear may be engaged with at least one third gear or the transmission gear.

A main frame may be provided under the mattress, and a dryer may be coupled to a bottom of the main frame and configured to blow air toward the mattress. The dryer may include a fan having an inlet to suction air and at least one outlet to discharge air, at least one supply duct coupled to the at least one outlet, at least one discharge duct coupled to the supply duct and having a discharge port through which air suctioned through the fan and guided through the supply duct may be discharged toward the mattress, and a filter configured to filter suctioned air. The fan may be a centrifugal fan having the inlet on a bottom surface and the outlet on a side surface such that air may be suctioned in an axial direction of the fan and discharged in a radial direction of the fan.

A guard may surround sides of the main frame and mattress. The guard may include a suction opening. The dryer may include a suction duct coupled to an inlet of the fan and having a suction port exposed through the suction opening. The filter may be provided at the inlet of the fan, at the suction port, or at the suction opening.

The supply duct may be provided over the suction duct. The supply duct may have at least one section that extends in a direction along the prescribed length. The supply duct and the suction duct may be parallel to each other. Alternatively or in addition thereto, the suction duct may be perpendicular to at least one section of the supply duct. At least one of the suction duct or the supply duct may include a flexible section configured to bend with a movement of the main frame.

The discharge duct may include a bottom surface and side walls defining an upper opening. The discharge port may be formed in the bottom surface. The discharge duct may extend in a direction perpendicular to the supply duct.

Embodiments disclosed herein may be implemented as a bed comprising a main frame configured to bend and straighten and a mattress configured to bend and straighten with a movement of the main frame. The mattress may include a plurality of cases coupled to the main frame. Each case may have a plurality of springs coupled to a plurality of gears and one motor configured to rotate the plurality of gears of the case to adjust a height of the plurality of springs.

Embodiments disclosed herein may be implemented as a bed comprising a main frame configured to bend and straighten, a mattress configured to bend and straighten with a movement of the main frame, and a dryer coupled to a bottom of the main frame. The mattress may include a plurality of cases coupled to a top of the main frame. Each case may have a plurality of cushions and a drive configured to adjust a firmness of the plurality of cushions. The dryer may have an inlet, a fan configured to suction air through the inlet, and an outlet such that air discharged through the outlet may be guided toward the mattress.

Embodiments disclosed herein may be implemented as a bed comprising a main frame and a mattress provided on the main frame. The mattress may include a plurality of cases. Each case may have a plurality of cushions and a motor configured to adjust a firmness of the plurality of cushions. The main frame may include a first frame configured to support an upper body, a second frame configured to support a lower body, and a first drive configured to move the first frame relative to the second frame. The first frame may have a plurality of first slats to support the mattress. At least one case may be coupled to the plurality of first slats. The second frame may have a plurality of second slats to support the mattress. At least one case may be coupled to the plurality of second slats.

The first frame may include a first section, a second section hinged to the first section, and a linkage coupling the first section to the first drive. The first drive may include a motor and a shaft. The shaft may be fixed to the linkage such that, when the motor rotates the shaft, at least a portion of the linkage may be rotated with the shaft. The linkage may be coupled to the first section and the second section. The linkage may include a first link coupled to the first section and a second link coupled to the first link and the shaft.

The first section may include a pair of first side frames. At least one first slat may extend between the pair of first side frames. The second section may include a pair of second side frames. At least one first slat may extend between the pair of second side frames. The linkage may include a pair of links parallel to each other. Each link in the pair of links may include a pair of first links coupled to the pair of first side frames, respectively, and a pair of second links coupled to the pair of first links, respectively, and the shaft.

A second drive may be configured to move the second frame relative to the first frame. The second drive may include a motor and a shaft. The second frame may include a first section, a second section hinged to the first section, and a linkage coupling the first and second sections to the shaft.

The linkage may include a first link coupled to the shaft, and a second link coupled to the second section and the first link. The second link may be coupled to the first link via a connection link, and at least one of the couplings between the second link and the second section, the connection link and the second link, or the connection link and the first link may be a hinge coupling.

The first link may be coupled to the shaft via a bracket. The bracket may be fixed to the shaft and rotatably coupled to the first link. The linkage may include an arm link fixed to the bracket and configured to rotate with a rotation of the shaft so as to maintain contact with a bottom of the rear section.

The first section may include a pair of first side frames. At least one first slat may extend between the pair of first side frames. The second section may include a pair of second side frames. At least one first slat may extend between the pair of second side frames. The first link may include a pair of first links coupled to the shaft, and the second link may include a pair of second links coupled to the pair of second side frames and the pair of first links.

An elastic foam layer may be seated on top of the mattress to be detachable. A guard may be configured to support the main frame and surround an outer side of the main frame. A plurality of legs may support the guard and may space the main frame apart from a floor surface.

A first blocking sheet may be coupled to a front of the guard and a front of the main frame. A second blocking sheet may be coupled to a rear of the guard and a rear of the main frame. The first and second blocking sheets may cover gaps formed during a movement of the main frame. A dryer may be coupled to a bottom of the main frame. The dryer may have a fan to suction air and discharge air toward the mattress.

Embodiments disclosed herein may be implemented as a bed comprising a main frame, a mattress provided on the main frame, and a dryer coupled to a bottom of the main frame. The main frame may have a plurality of slats extending in a first direction, a first frame, and a second frame adjacent to the first frame in a second direction perpendicular to the first direction. The first and second frames may be rotatable relative to each other. The mattress may include a plurality of cases. Each case may have a plurality of cushions and a drive configured to adjust a firmness of the plurality of cushions. The plurality of cases may be coupled to the plurality of slats. The dryer may have a fan configured to suction air, a supply duct extending in the second direction and coupled to an outlet of the fan, and a plurality of discharge ducts extending in the second direction. Each discharge duct may have an outlet through which air may be discharged through the plurality of slats and toward the mattress.

A plurality of legs may support the main frame and may space the dryer apart from a floor surface. A partition may be provided between adjacent cases and the first and second frames to prevent collision of the cushions during a movement of the first or second frames. The partition may be made of an elastic material and have a plurality of holes through which air discharged from the dryer flows. The fan may be configured to suction air in an axial direction and discharge air in a radial direction.

Embodiments disclosed herein may be implemented as a bed comprising a main frame having a plurality of frames hinged to each other so as to be rotatable relative to each other, a plurality of cases coupled to the plurality of frames, each case having a plurality of cushions, and at least one partition provided between adjacent of cases at a position aligned with a rotation axis of the plurality of frames so as to prevent collision between cushions during rotations of the plurality of frames. Each case may have a drive configured to adjust a firmness of the plurality of cushions. The partition may be made of an elastic material and including a plurality of fins formed in an upper section.

Embodiments disclosed herein may be implemented as a bed comprising a mattress, a main frame configured to support the mattress, the main frame having a plurality of frames adjacent in a first direction that may be rotatable relative to each other, a plurality of plates adjacent in the first direction, the plurality of plates seated on the plurality of frames, respectively, and at least one joint provided between and hinged to adjacent plates so that the plurality of plates may be rotatable relative to each other. The joint may align with a rotation axis between adjacent frames of the main frame. The at least one joint may include three joints hinged to each other.

The joint may include a plurality of teeth. The plates may include a plurality of teeth configured to engage with the plurality of teeth of the joints. A hinge pin may penetrate the plurality of teeth of the joints and the plates.

Each frame may include a plurality of cases coupled to the frame. Each case may include a plurality of cushions, and a drive configured to adjust a firmness of the plurality of cushions.

Each case may include a bottom case coupled to the frame and an upper case in which the cushions may be provided. The drive may include a motor housed between the bottom case and the upper case.

Each cushion may include an outer case, an outer spring provided inside of the outer case, an inner case provided inside of the outer case and the outer spring, an inner spring provided in the inner case, a screw configured to change a height of the inner spring relative to the outer spring when the screw may be rotated, and a transmission gear configured to rotate the screw. The drive may include a motor and a gear assembly configured to engage with the transmission gear to rotate the transmission gear. When the transmission gear is rotated, a height of the inner spring may change with respect to a height of the outer spring, and a firmness of the cushion may change.

At least one partition may be provided above the joint to be between the adjacent plates and adjacent cases. The partitions may include a plurality of slits to allow air to flow therebetween and a plurality of fins at an upper portion.

A guard may surround the main frame, the plurality of plates, and the mattress. An inner surface of the guard may include a ledge to which the main frame may be coupled. The guard may include legs provided at corners of the guard to space the main frame apart from an installation surface.

A dryer may be coupled to a bottom of the main frame. The dryer may include a fan configured to suction air in an axial direction and discharge air in a radial direction, a supply duct coupled to an outlet of the fan and extending in the first direction, the supply duct having a plurality of extensions that branch off toward a second direction perpendicular to the first direction, and a discharge port provided at ends of the extensions and configured to discharge air upward toward the mattress. Portions of the supply duct below the rotation axes of the frames may be configured to be flexible so that the supply duct moves with a rotation of the frames.

A cover sheet may surround the mattress and the seat plate. The cover sheet may have a plurality of holes through which air discharged from the dryer flows.

Embodiments disclosed herein may be implemented as a bed comprising a mattress having a plurality of independently controlled regions, each region having a drive to control a firmness of the region, a main frame configured to support the mattress, the main frame configured to have a plurality of frames that may be rotatable relative to each other to adjust a posture of the main frame, a plurality of legs to space the mattress apart from a floor surface, and a dryer coupled to a bottom of the main frame and configured to discharge air toward the mattress to dry the mattress. The dryer may include a fan configured to suction air through an inlet of the fan, a duct coupled to an outlet of the fan to guide discharged air through the duct, the duct having at least one flexible section provided under a rotation axis between adjacent frames of the main frame, and a plurality of extensions branched off from the duct. The plurality of extensions may have discharge ports through which air may be discharged upward toward the mattress.

A sheet may be woven with a plurality of electrodes to sense a pressure in the regions. The firmness of the region may be adjusted based on the sensed pressure.

The fan may be provided under a foot of the main frame. The duct may extend from the fan in a longitudinal direction of the main frame toward a head of the main frame. The extensions may extend in a direction perpendicular to the duct.

Discharge ducts may be provided on top of the extensions. The discharge ducts may have discharge slots that extend in a direction parallel to a longitudinal direction of the main frame to discharge air upward.

The mattress may include a first layer and a second layer provided over the first layer. The first layer may have a plurality of first springs and a plurality of second springs. The drive may include at least one motor configured to change a height of the plurality of first springs relative to the plurality of second springs to adjust the firmness of the mattress. A second layer may be provided over the first layer. The second layer may be made of an elastic foam material to provide padding over the first and second springs.

Embodiments disclosed herein may be implemented as a bed comprising a main frame having a plurality of frames adjacent in a first direction that may be rotatable relative to each other a seat plate having a plurality of plates adjacent in the first direction that may be rotatable relative to each other, wherein the plurality of plates may be provided over the plurality of frames, respectively, a plurality of cases provided over the seat plate, the plurality of cases having a plurality of cushions, an elastic foam pad provided over the plurality of spring cushions, at least one partition provided between adjacent cases at a position corresponding to a rotation axis between two adjacent frames, a fan provided under a first end of the main frame to suction air, a duct coupled to the fan to receive air discharged from the fan, the duct extending in the first direction toward a second end of the main frame opposite the first end, and a plurality of discharge ports configured to discharge air upward toward the cushions and elastic foam pad.

Embodiments disclosed herein may be implemented as a method of controlling mattress firmness comprising sensing a pressure at a plurality of points on a mattress, determining a plurality of average pressure values for a plurality of regions of the mattress based on the sensed pressure at the plurality of points, and independently operating a plurality of motors based on the determined average pressure values. A corresponding motor may be provided in a corresponding region.

Each motor may rotate a gear among a plurality of gears engaged with each other. Some of the plurality of gears may be coupled to a plurality of cushions corresponding to a region among the plurality of regions such that, when the motor in the region is powered to rotate the gear, a firmness of the cushions in the region may be adjusted.

Each cushion may include an outer spring, an inner spring provided in a case, and a screw provided between the case and a gear of the plurality of gears such that, when the motor is powered to rotate the gear, a height of the inner spring may change with respect to the outer spring to adjust the firmness of the cushion.

A pressure sensing sheet may be provided on the mattress to sense the pressure at the plurality of points. The pressure sensing sheet may have a plurality of first electrode lines that intersect with a plurality of second electrode lines. Intersections between the plurality of first and second electrode lines may correspond to the plurality of points.

The method may further comprise processing the average pressure values, generating a pressure distribution image based on the processed average pressure values, and outputting the pressure distribution image on a display. Generating the pressure distribution image may include generating a color coded image, wherein a spectrum of colors corresponds to a range of the average pressure values. A user interface may be provided on a remote controller having a display.

Upon receiving an automatic command based on a user input into a user interface, the step of independently operating the plurality of motors based on the determined average pressure value may include determining a range value of the determined average pressure values, the range value being a difference between the highest average pressure and the lowest average pressure, comparing the determined range value to a predetermined range value, and when the determined range exceeds the predetermined range, operating the motor to change the firmness in the region having the highest pressure or operating the motor to change the firmness in the region having the lowest pressure. After independently operating the plurality of motors based on the determined average pressure value, the method may include repeating the sensing the pressure, determining the average pressure, and independently operating until the determined range does not exceed the predetermined range.

Upon receiving an automatic command based on a user input into a user interface, the step of independently operating the plurality of motors based on the determined average pressure value may include comparing the determined average pressure value for a region to a predetermined maximum pressure value for the region, and when the determined average pressure value for the region exceeds the predetermined maximum pressure value for the region, operating the motor in the region to change the firmness. After independently operating the plurality of motors based on the determined average pressure value, the method may include repeating the sensing the pressure, determining the average pressure, and independently operating until the determined average pressure values for the regions do not exceed the predetermined maximum pressure values for the regions.

Upon receiving an automatic command based on a user input into a user interface, the step of independently operating the plurality of motors based on the determined average pressure value may include comparing the determined average pressure value for a region to a predetermined minimum pressure value for the region, and when the determined average pressure value for the region is less than the predetermined minimum pressure value for the region, operating the motor in the region to change the firmness. After independently operating the plurality of motors based on the determined average pressure value, the method may include repeating the sensing the pressure, determining the average pressure, and independently operating until the determined average pressure values for the regions are not below the predetermined minimum pressure values for the regions.

Upon receiving a manual command based on a user input into a user interface and receiving a selected pressure value for a region via the user interface, the step of independently operating the plurality of motors based on the determined average pressure value may include comparing the determined average pressure value for a region to the desired pressure value, and operating the motor for the region to change the firmness to the selected pressure value. After independently operating the plurality of motors based on the determined average pressure value, the method may include repeating the sensing the pressure, determining the average pressure, and independently operating until the determined average pressure values for the regions are within a predetermined error range of the selected pressure value.

Sensing the pressure at the plurality of points on the mattress may include repeatedly sensing the pressure, determining a difference between a current sensed pressure and a previous sensed pressure, comparing the determined difference to a predetermined error range, when the determined difference is within the predetermined error range for a predetermined time period, proceeding to the step of determining the average pressure value, and when the determined difference is not within the predetermined error range for the predetermined time period, stopping sensing for a predetermined waiting period, and repeating the step of repeatedly sensing the pressure after the predetermined waiting period.

Embodiments disclosed herein may be implemented as a method of controlling a mattress firmness comprising receiving a command to adjust a firmness of the mattress, performing a pressure scan of the mattress, storing data from the pressure scan, processing the stored data, determining, using the stored data, pressure values corresponding a plurality of regions of the mattress, each region having a plurality of elastic members, generating, via the processed data, a pressure distribution image, outputting the pressure distribution image on a display, comparing the determined pressure values to predetermined pressure values, and independently controlling a corresponding motor for a corresponding region based on the comparison between the determined pressure values and the predetermined pressure values, each motor being configured to change a height of some of the elastic members in a region compared to the other elastic members in the region. The pressure scan may include sensing a plurality of pressures using a pressure sensor sheet provided on a mattress.

The predetermined pressure values may be selected based on a user selection via a user interface provided on a remote controller, the remote controller having the display. The predetermined pressure values may be determined based on at least one of past user selections provided via a user interface, a weight of a user entered via a user interface, or a comparison of all of the determined pressure values to each other.

Embodiments disclosed herein may be implemented as a bed comprising a mattress having a first layer and a second layer provided over the first layer, the first layer having a plurality of adjustable cushions. Each adjustable cushion may include a case, a plurality of elastic cushions provided on the case, a drive coupled to the case, and a plurality of driving gears configured to transmit a force from the drive to the plurality of elastic cushions such that a firmness of the adjustable cushion is adjusted when the drive is operated.

A cover sheet may be configured to surround at least the first and second layers. The second layer may be made of an elastic foam. A bottom of the elastic foam may be formed with a plurality of cushion sleeves in which upper ends of the plurality of elastic cushions are inserted.

Each elastic cushion may include a first elastic member, a second elastic member, a first case coupled to the first elastic member, a transmission gear configured to be engaged with the plurality of driving gears, and a screw penetrating the first case such that, when the transmission gear rotates, the first case may rise or descend along the screw such that a height difference between the first and second elastic members changes.

The second elastic member may surround the first elastic member and is provided on a second case. The first case is provided inside of the second case. A buffer may be provided over the first elastic member. An upper cover may cover the buffer and the second elastic member. A first cover may be provided around the first elastic member. A second cover may be provided around the second elastic member.

A bottom of the second layer may be formed with a plurality of recesses. Tops of the plurality of elastic cushions may be configured to be inserted into the plurality of recesses. The recesses may be formed inside of cushion sleeves which extend downward from the bottom of the second layer.

A main frame may support the mattress. The main frame may have a first frame and a second frame rotatably coupled to the first frame, and a plurality of partitions provided between adjacent cases at a rotation axis of the first and second frames. A bottom of the second layer may be formed with a plurality of recesses, and tops of the plurality of partitions may be configured to be inserted into the plurality of recesses.

The second layer may include a plurality of buffer plates provided on top of a plurality of elastic cushions of at least one adjustable cushion. A bottom of the buffer plate may be formed with recesses in which the plurality of elastic cushions are inserted.

A pad may be provided on top of the buffer plate. A length of the buffer plate may correspond to a width of the top pad. A width of the buffer plate may correspond to a width equal to a width of the case. Two adjacent cases may fit in a width direction of the pad. The buffer plate may be configured to cover the two adjacent cases without covering a rotation axis between the first and second frames.

Embodiments disclosed herein may be implemented as a mattress for a bed comprising a first layer and a second layer provided over the first layer. The first layer may have a plurality of regions in which firmness is independently adjusted by a plurality of motors, each region having at least one case corresponding to a motor among the plurality of motors and a plurality of cushions provided in the case to be controlled by the motor. The first layer may be flexible at at least one position between adjacent cases provided in adjacent regions, and each cushion may include at least one spring. The second layer may be made of an elastic foam material. A cover sheet may be configured to surround the first layer and the second layer.

A bottom of the second layer may be formed with a plurality of recesses in which top ends of the plurality of cushions are inserted. A plurality of plates may correspond to the plurality of regions and be configured to cover the plurality of cushions in each region. A bottom of each plate may be formed with recesses in which top ends of the plurality of cushions are inserted. A sheet may be provided over the second layer, the sheet being woven with a plurality of electrode lines configured to sense a pressure.

A base may be provided below the first layer. The base may include a plurality of frames corresponding to the plurality of regions, the plurality of frames being hinged to each other. The first and second layers may move with a movement of the base.

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A bed, comprising
a mattress having a prescribed width and a prescribed length, the mattress having a plurality of cushion cases,
wherein each cushion case of the plurality of cushion cases includes:
a plurality of cushions provided in the cushion case,
a drive coupled to the cushion case, and
a plurality of drive gears configured to transmit a force from the drive to the plurality of cushions such that a firmness of the cushions in the cushion case are adjusted when the drive is operated,
wherein each cushion includes:
a first elastic member,
a second elastic member surrounding the first elastic member,
a screw configured to change a height of the first elastic member with respect to the second elastic member when the screw is rotated, and
a transmission gear configured to rotate the screw and configured to engage with at least one drive gear of the plurality of drive wars,
wherein the drive includes at least one of an actuator or a motor, and the plurality of drive gears include:
a first gear coupled to a rotation shaft of the drive,
at least one second gear engaged with the first gear, and
a plurality of third gears provided between adjacent transmission gears,
wherein the second gear is engaged with at least one third gear or the transmission gear.

2. The bed of claim 1, wherein the mattress further includes:
a top pad provided over the plurality of cushions of the plurality of cushion cases, and
a cover provided to surround the top pad and the plurality of cushion cases.

3. The bed of claim 2, further comprising
a main frame having a first frame rotatably coupled to a second frame such that a posture of the main frame is adjustable; and
a guard surrounding sides of the main frame and mattress.

4. The bed of claim 3, wherein the mattress includes a partition provided along a direction of the prescribed width and between a pair of adjacent cushion cases.

5. The bed of claim 4, wherein at least one of the partition, the top pad, or the guard is made of an elastic foam material.

6. The bed of claim 1, further comprising a main frame, having:
a first frame configured to support a first section of a user's body;
a second frame hinged to the first frame and configured to support a section of a user's upper body and hinged to the first frame,
a third frame configured to support a first section of a user's lower body and hinged to the first frame,
a fourth frame configured to support a second section of a user's lower body and hinged to the third frame,
a first actuator configured to rotate the first frame with respect to the second frame, and
a second actuator configured to rotate the third frame with respect to the first frame.

7. The bed of claim 1, wherein the mattress includes a top pad provided over the plurality of cushions of the plurality of cushion cases, and the top pad includes a plurality of sleeves protruding from a bottom surface, the plurality of sleeves configured to surround upper ends of the plurality of cushions.

8. The bed of claim 1, further comprising
a main frame provided under the mattress; and
a dryer coupled to a bottom of the main frame and configured to blow air toward the mattress.

9. The bed of claim 8, wherein the dryer includes:
a fan having an inlet to suction air and at least one outlet to discharge air,
at least one supply duct coupled to the at least one outlet,
at least one discharge duct coupled to the supply duct and having a discharge port through which air suctioned through the fan and guided through the supply duct is discharged toward the mattress, and
a filter configured to filter suctioned air.

10. The bed of claim 9, wherein the fan is a centrifugal fan having the inlet on a bottom surface and the outlet on a side surface such that air is suctioned in an axial direction of the fan and discharged in a radial direction of the fan.

11. The bed of claim 9, further comprising a guard surrounding sides of the main frame and mattress, the guard including a suction opening, wherein the dryer further includes a suction duct coupled to an inlet of the fan and having a suction port exposed through the suction opening, and the filter is provided at the inlet of the fan, at the suction port, or at the suction opening.

12. The bed of claim 11, wherein the supply duct is provided over the suction duct, and the supply duct has at least one section that extends in a direction along the prescribed length.

13. The bed of claim 11, wherein the supply duct and the suction duct are parallel to each other.

14. The bed of claim 11, wherein the suction duct is perpendicular to at least one section of the supply duct.

15. The bed of claim 11, wherein at least one of the suction duct or the supply duct includes a flexible section configured to bend with a movement of the main frame.

16. The bed of claim 10, wherein the discharge duct includes a bottom surface and side walls defining an upper opening, the discharge port is formed in the bottom surface, and the discharge duct extends in a direction perpendicular to the supply duct.

17. A bed, comprising
a mattress having a prescribed width and a prescribed length, the mattress having a plurality of cushion cases,
wherein each cushion case of the plurality of cushion cases includes:
a plurality of cushions provided in the cushion case,
a drive coupled to the cushion case, and
a plurality of driving gears configured to transmit a force from the drive to the plurality of cushions such that a firmness of the cushions in the cushion case are adjusted when the drive is operated;
a main frame provided under the mattress;
a guard surrounding sides of the main frame and mattress and having a suction opening; and
a dryer coupled to a bottom of the main frame and configured to blow air toward the mattress,
wherein the dryer includes:
a fan having an inlet to suction air and at least one outlet to discharge air;
at least one supply duct coupled to the at least one outlet;
at least one discharge duct coupled to the supply duct and having a discharge port through which air suctioned through the fan and guided through the supply duct is discharged toward the mattress;

a filter configured to filter suctioned air; and a suction duct coupled to an inlet of the fan and having a suction port exposed through the suction opening, wherein the filter is provided at the inlet of the fan, at the suction port, or at the suction opening.

18. The bed according to claim 17, wherein the fan is a centrifugal fan having the inlet on a bottom surface and the outlet on a side surface such that air is suctioned in an axial direction of the fan and discharged in a radial direction of the fan.

19. The bed of claim 17, wherein the supply duct is provided over the suction duct, and the supply duct has at least one section that extends in a direction along the prescribed length.

20. The bed of claim 1, wherein the supply duct and the suction duct are parallel to each other.

21. The bed of claim 17, wherein the suction duct is perpendicular to at least one section of the supply duct.

22. The bed of claim 17, wherein at least one of the suction duct or the supply duct includes a flexible section configured to bend with a movement of the main frame.

23. The bed of claim 17, wherein the discharge duct includes a bottom surface and side walls defining an upper opening, the discharge port is formed in the bottom surface, and the discharge duct extends in a direction perpendicular to the supply duct.

\* \* \* \* \*